US011842456B2

(12) United States Patent
Gluhovsky et al.

(10) Patent No.: US 11,842,456 B2
(45) Date of Patent: Dec. 12, 2023

(54) FLATTENED VIEW FOR INTRA-LUMENAL NAVIGATION

(71) Applicant: Navix International Limited, Road Town (VG)

(72) Inventors: Leonid Gluhovsky, Gilon (IL); Yitzhack Schwartz, Haifa (IL); Eli Dichterman, Haifa (IL); Shlomo Ben-Haim, Milan (IT); Yaara Yarden, Jerusalem (IL)

(73) Assignee: Navix International Limited, Road Town (VG)

( * ) Notice: Subject to any disclaimer, the term of this patent is extended or adjusted under 35 U.S.C. 154(b) by 385 days.

(21) Appl. No.: 16/476,893

(22) PCT Filed: Jan. 12, 2018

(86) PCT No.: PCT/IB2018/050201
§ 371 (c)(1),
(2) Date: Jul. 10, 2019

(87) PCT Pub. No.: WO2018/130981
PCT Pub. Date: Jul. 19, 2018

(65) Prior Publication Data
US 2019/0340838 A1    Nov. 7, 2019

Related U.S. Application Data

(60) Provisional application No. 62/564,479, filed on Sep. 28, 2017, provisional application No. 62/445,368, filed on Jan. 12, 2017.

(51) Int. Cl.
*G06T 19/20* (2011.01)
*A61B 5/00* (2006.01)
(Continued)

(52) U.S. Cl.
CPC ............ *G06T 19/20* (2013.01); *A61B 5/0044* (2013.01); *A61B 5/0536* (2013.01);
(Continued)

(58) Field of Classification Search
None
See application file for complete search history.

(56) References Cited

U.S. PATENT DOCUMENTS

| 10,231,784 B2 | 3/2019 | Hettrick et al. |
| 2005/0058328 A1 | 3/2005 | Moreau-Gobard |

(Continued)

FOREIGN PATENT DOCUMENTS

| EP | 1726268 | 11/2006 |
| EP | 2075763 | 7/2009 |

(Continued)

OTHER PUBLICATIONS

Pascale Beliveau, Randolph Setser, Farida Cheriet, Thomas O'Donnell, "Patient-Specific Coronary Territory Maps", Mar. 29, 2007, SPIE, Proc. SPIE 6511, Medical Imaging 2007: Physiology, Function, and Structure from Medical Images.*

(Continued)

*Primary Examiner* — Robert Bader

(57) ABSTRACT

Methods for creation and use (e.g., for navigation) of displays of flattened (e.g., curvature-straightened) 3-D reconstructions of tissue surfaces, optionally including reconstructions of the interior surfaces of hollow organs. In some embodiments, data comprising a 3-D representation of a tissue surface (for example an interior heart chamber surface) are subject to a geometrical transformation allowing the tissue surface to be presented substantially within a single view of a flattened reconstruction. In some embodiments, a catheter probe in use near the tissue surface is shown in positions that correspond to positions in 3-D space (Continued)

sufficiently to permit navigation; e.g., the probe is shown in flattened reconstruction views nearby view regions corresponding to regions it actually approaches. In some embodiments, automatic and/or easily triggered manual view switching between flattened reconstruction and source reconstruction views is implemented.

23 Claims, 22 Drawing Sheets

(51) Int. Cl.
    *A61B 5/0536*     (2021.01)
    *A61B 5/0538*     (2021.01)
    *A61B 5/06*     (2006.01)

(52) U.S. Cl.
    CPC ............ *A61B 5/0538* (2013.01); *A61B 5/068* (2013.01); *A61B 2576/023* (2013.01); *G06T 2210/41* (2013.01); *G06T 2219/2021* (2013.01)

(56) References Cited

U.S. PATENT DOCUMENTS

| | | | |
|---|---|---|---|
| 2005/0105786 A1* | 5/2005 | Moreau-Gobard | ... G06T 7/0012 382/128 |
| 2005/0222554 A1 | 10/2005 | Wallace et al. | |
| 2009/0225077 A1 | 9/2009 | Sudarsky et al. | |
| 2011/0142306 A1† | 6/2011 | Nair | |
| 2011/0274326 A1† | 11/2011 | Allain | |
| 2014/0330111 A1 | 11/2014 | Lichtenstein et al. | |
| 2016/0055681 A1* | 2/2016 | Koyrakh | ................. G06T 19/00 345/427 |
| 2017/0319172 A1 | 11/2017 | Harlev et al. | |
| 2018/0200018 A1 | 7/2018 | Silva et al. | |
| 2019/0200886 A1 | 7/2019 | Welsh et al. | |
| 2019/0336035 A1 | 11/2019 | Dichterman et al. | |

FOREIGN PATENT DOCUMENTS

| | | |
|---|---|---|
| EP | 2712543 | 4/2014 |
| WO | WO 98/01069 | 1/1998 |
| WO | 2014172524 | † 10/2014 |
| WO | WO 2018/130981 | 7/2018 |
| WO | WO 2019/063161 | 4/2019 |
| WO | WO 2019/215574 | 11/2019 |

OTHER PUBLICATIONS

HamidReza Houshiar, Jan Elseberg, Dorit Borrmann, Andreas Nuchter, "A Study of Projections for Key Point Based Registration of Panoramic Terrestrial 3D Laser Scans", Mar. 16, 2015, Taylor & Francis, Geo-spatial Information Science, vol. 18, 2015, issue 1.*
R. C. Chan, Z. Malchano, R. Vijaykumar, R. Manzke, L. Zagorchev, V. Y. Reddy, "Intraprocedural fusion of electroanatomical maps (EAM) with imaging data based on rapidly-sampled volumetric point clouds from continuous EAM catheter tracking", Mar. 21, 2007, SPIE, Proc. SPIE 6509, Medical Imaging 2007, 65090R.*
Ajay Limaye, "Drishti, A Volume Exploration and Presentation Tool", Oct. 17, 2012, SPIE, Proc. SPIE 8506, Developments in X-Ray Tomography VIII, 85060X.*
Maurice Termeer, Javier Olivan Bescos, Marcel Breeuwer, Anna Vilanova, Frans Gerritsen, M. Eduard Groller, "CoViCAD: Comprehensive Visualization of Coronary Artery Disease", Dec. 2007, IEEE, IEEE Transactions on Visualization and Computer Graphics, vol. 13, No. 6, pp. 1632-1639.*

International Preliminary Report on Patentability dated Nov. 21, 2019 From the International Bureau of WIPO Re. Application No. PCT/IB2018/053258. (8 Pages).
International Preliminary Report on Patentability dated Aug. 22, 2019 From the International Bureau of WIPO Re. Application No. PCT/TB2018/050784. (11 Pages).
International Preliminary Report on Patentability dated Jul. 25, 2019 From the International Bureau of WIPO Re. Application No. PCT/IB2018/050192. (8 Pages).
International Preliminary Report on Patentability dated May 31, 2019 From the International Burau of WIPO Re. Application No. PCT/IB2017/057185. (11 Pages).
International Preliminary Report on Patentability dated Jul. 25, 2019 From the International Bureau of WIPO Re. Application No. PCT/IB2018/050201. (15 Pages).
International Search Report and the Written Opinion dated Jun. 6, 2018 From the International Searching Authority Re. Application No. PCT/IB2018/050201. (24 Pages).
Invitation to Pay Additional Fees, Communication Relating to the Results of the Partial International Search and the Provisional Opinion dated Apr. 25, 2018 From the International Searching Authority Re. Application No. PCT/IB2018/050201. (14 Pages).
Ahn et al. "Height-Based Deformation and Ray Supersampling for Colon Unfolding", ICAT'06 Proceedings of the 16th International Conference on Advances in Artificial Reality and Tele-Existence, Lecture Notes in Computer Science, XP047402101, Hangzhou, China, Nov. 29-Dec. 1, 2006, p. 1098-1107, Nov. 29, 2006. Sections 3.1, 3.3, 5, Figs.2, 4, 5.
Bartroli et al. "Nonlinear Virtual Colon Unfolding", Proceedings of the IEEE Conference on Visualization '01, VIS '01, XP031385694, San Diego, CA, USA, Oct. 21-26, 2001, p. 411-420, Oct. 21, 2001. Sections 4, 4.1, 4.2, 5.1, 7, Figs.1, 7a, 7b, 10.
General Electric "CardEP: Streamlined Post-Processing for Enhanced Electrophysiology Procedures", General Electric Company, GE Healthcare, Product Description, 2 P., 2016.
Karim et al. "Surface Flattening of the Human Left Atrium and Proof-of-Concept Clinical Applications", Computerized Medical Imaging and Graphics, 38(4): 251-266, Jun. 2014.
Perazzi et al. "Panoramic Video From Unstructured Camera Arrays", Computer Graphics Forum, 34(2): 57-68, May 2015.
Wang et al. "Colon Unraveling Based on Electrical Field: Recent Progress and Further Work", Proceedings of the SPIE 3660 Medical Imaging '99: Physiology and Function From Multidimensional Images, San Diego, CA, USA, Feb. 1999, XP055479173, 3660: 125-133, May 20, 1999. Abstract, Sections 1, 2.2, 2.3, Figs.2, 3.
Zhong et al. "On the Accuracy of CartoMerge for Guiding Posterior Left Atrial Ablation in Man", Heart Rhythm, 4(5): 595-602, Published Online Feb. 9, 2007.
International Search Report and the Written Opinion dated Mar. 7, 2019 From the International Searching Authority Re. Application No. PCT/EP2018/069569. (25 Pages).
AridOcean "Iran, High Resolution 3D Relief Maps", Turbosquid, XP055528216, Retrieved From the Internet, Aug. 11, 2010.
Guldenring et al. "Estimation Accuracy of a Reduced Lead System During Simulated Ischemia", 2011 Computing in Cardiology, CINC 2011, XP032167248, Hangzhou, China, Sep. 18-21, 2011, p. 237-240, Sep. 18, 2011.
Ma et al. "Cardiac Unfold: A Novel Technique for Image-Guided Cardiac Catheterization Procedures", IPCAI'12, Proceedings of the Third International Conference on Information Processing in Computer-Assisted Interventions, XP047006734, p. 104-114, Jun. 27, 2012.
Official Action dated Jun. 8, 2021 From the U.S. Patent and Trademark Office Re. U.S. Appl. No. 16/650,973. (27 Pages).
Notice of Allowance dated Nov. 9, 2021 From the U.S. Patent and Trademark Office Re. U.S. Appl. No. 16/650,973. (5 Pages).
Bartroli et al, "Nonlinear Virtual Colon Unfolding", IEEE Visualization 2001, Oct. 2001, pp. 411-579.†

\* cited by examiner
† cited by third party

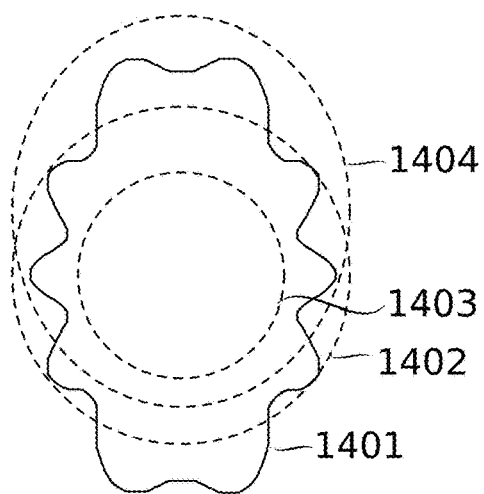
FIG. 14A
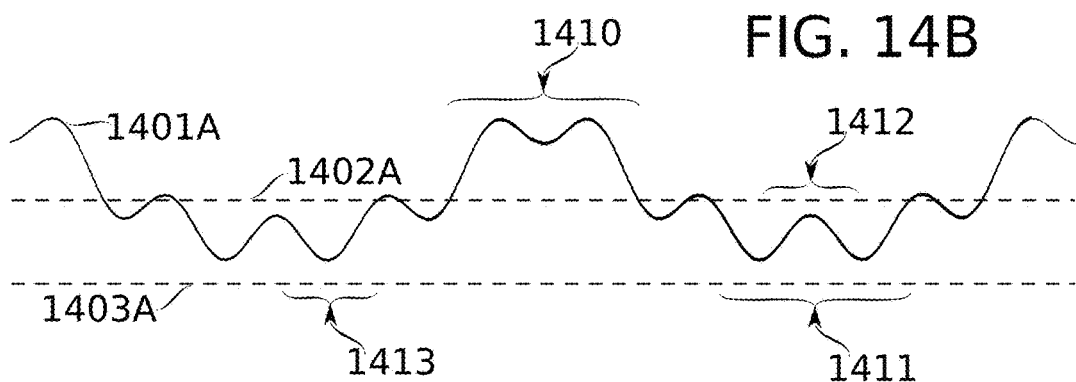
FIG. 14B
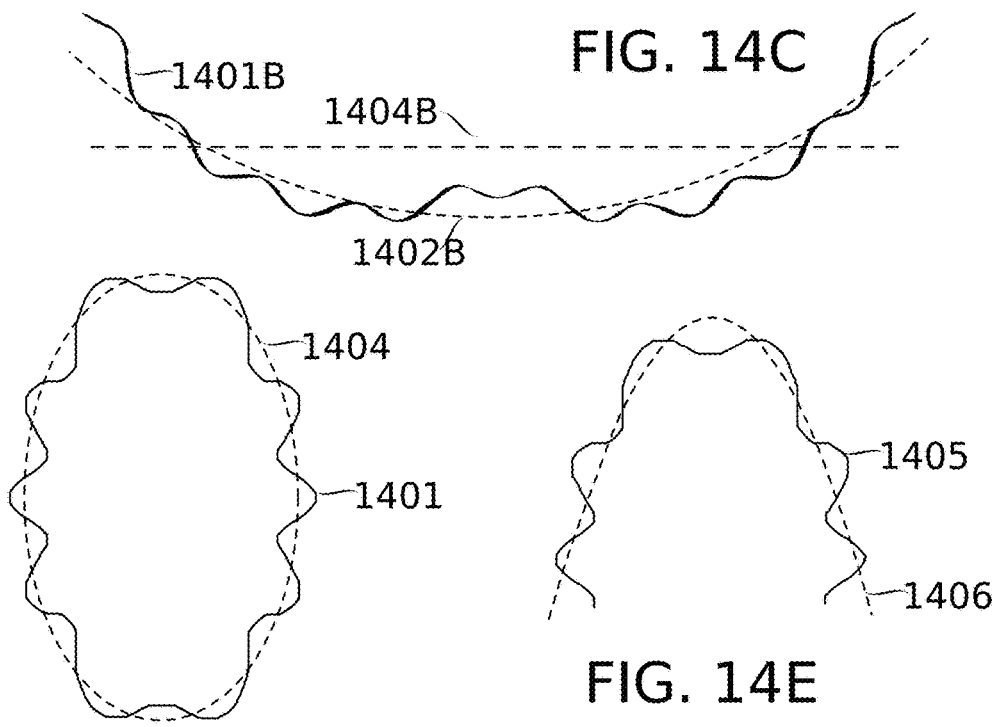
FIG. 14C
FIG. 14D
FIG. 14E

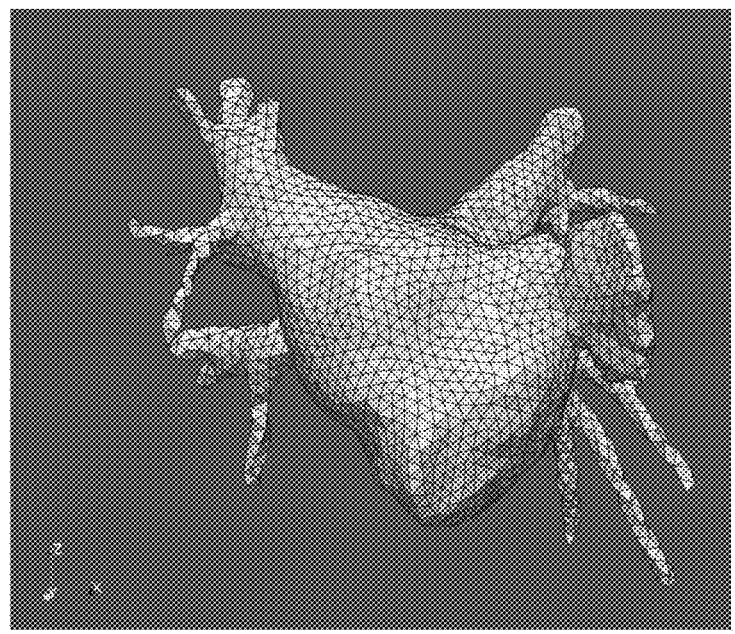
FIG. 16A
FIG. 16B
FIG. 16C
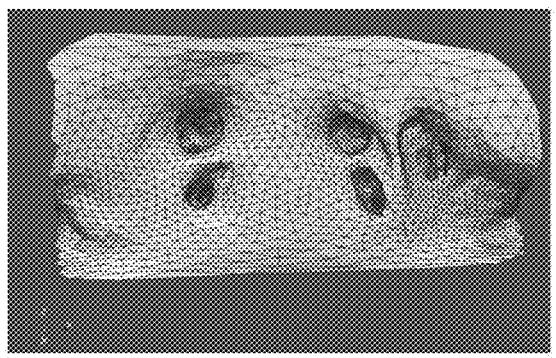 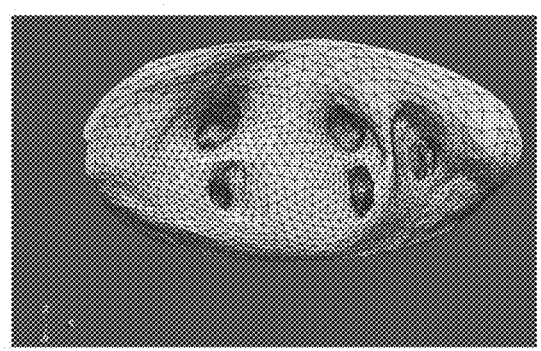
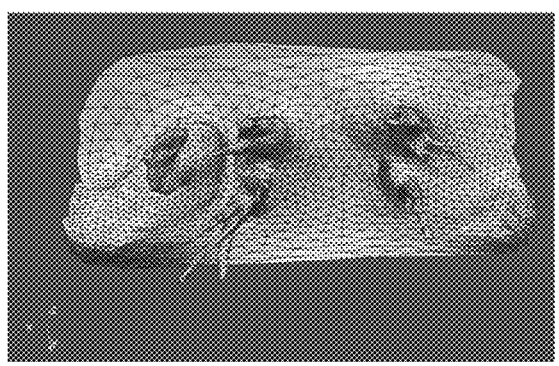 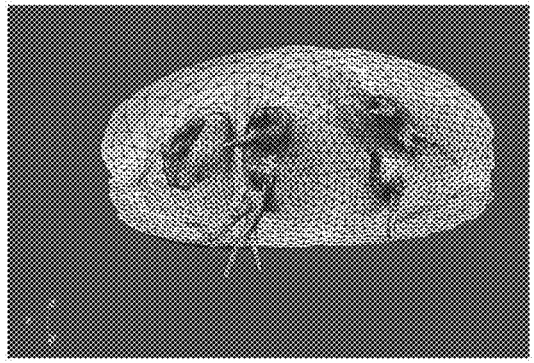
FIG. 16D
FIG. 16E

FLATTENED VIEW FOR INTRA-LUMENAL NAVIGATION

RELATED APPLICATIONS

This application is a National Phase of PCT Patent Application No. PCT/IB2018/050201 having International filing date of Jan. 12, 2017, which claims the benefit of priority under 35 USC § 119(e) of U.S. Provisional Patent Application No. 62/445,368 filed on Jan. 12, 2017, and U.S. Provisional Patent Application No. 62/564,479 filed on Sep. 28, 2017.

PCT Patent Application No. PCT/IB2018/050201 is also related to U.S. Provisional Patent Application No. 62/445,433 filed on Jan. 12, 2017.

The contents of the above applications are all incorporated by reference as if fully set forth herein in their entirety.

FIELD AND BACKGROUND OF THE INVENTION

The present invention, in some embodiments thereof, relates to the field of medical procedures using intrabody probes navigable within intrabody spaces, and more particularly, to presentation of data acquired during the course of a catheter procedure.

Several medical procedures in cardiology and other medical fields comprise the use of catheters to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field-guided position sensing systems. Refinements to techniques for registration of previously imaged (for example, by CT and/or MRI) anatomical features of a patient to electromagnetic field-sensed catheter position are a subject of ongoing research and development, for example as described in International Patent Application No. IB2016/052687 to Schwartz et al. filed May 11, 2016; and International Patent Application No. IB2016/052692 to Schwartz et al. filed May 11, 2016. Intrabody sensing from catheter probes to determine information about, for example, tissue contact and/or lesion assessment, has also been described (e.g., International Patent Application No. PCT IB2016/052690 to Schwartz et al. filed May 11, 2016; and International Patent Application No. IB2016/052686 to Schwartz et al. filed May 11, 2016).

SUMMARY OF THE INVENTION

There is provided, in accordance with some embodiments of the present disclosure, a method of producing an image of a curved body tissue surface, the method comprising: transforming a source 3-D model of the curved body tissue surface into a flattened 3-D model comprising relief details of the body tissue surface represented as relative differences in depth over an unwrapped and flattened surface extent; and producing an image from the flattened 3-D model.

In some embodiments, the transforming produces a flattened 3-D model having width, length, and depth.

In some embodiments, the relief details are represented in depth, and the width and length correspond to spherical angle positions in the source 3-D model.

In some embodiments, the flattened 3-D model also represents transformed positions from the volume of the source 3-D model away from the curved body tissue surface.

In some embodiments, the body tissue surface comprises an inner lumen surface of a body cavity.

In some embodiments, the source 3-D model represents the inner lumen surface through a solid angle of at least $3\pi$ steradians.

In some embodiments, the produced image represents at least 80% of the interior lumen surface.

In some embodiments, the body cavity comprises a heart left atrium.

In some embodiments, at least one feature from among a group of features consisting of: a heart left atrial appendage ridge, trans-septal, and mitral valve leaflet is distinguishably and identifiably represented in the flattened 3-D model.

In some embodiments, the body cavity comprises a heart right atrium.

In some embodiments, at least one feature from among a group of features consisting of: a Thebesian valve, Eustachian valve, tricuspid valve leaflet, and a coronary sinus is distinguishably and identifiably represented in the flattened 3-D model.

In some embodiments, the transforming introduces a discontinuity between two portions of the flattened 3-D model which correspond to two different and adjacent portions of the curved body tissue surface.

In some embodiments, the transforming comprises converting a representation of the source 3-D model in spherical coordinates into 3-D Cartesian coordinates to produce the flattened 3-D model.

In some embodiments, the body tissue surface comprises at least one of a group consisting of a heart chamber, blood vessel, lymph vessel, bone, membrane, cyst, gastrointestinal tract portion, kidney/urinary tract portion, respiratory tract portion, reproductive tract portion, eye, ear, CNS ventricle, and peritoneum.

In some embodiments, the source 3-D model is updated during the repeating a plurality of performances of the transforming and producing, wherein the source 3-D model is updated during the repeating by new data indicating positions of the surface.

In some embodiments, the source 3-D model is iteratively updated with position measurements of the surface measured from an intrabody probe, as the intrabody probe is moved within a lumen defined by the surface.

In some embodiments, the position measurements measured from the intrabody probe are measured using measurements of one or more electrical fields established within the body cavity.

In some embodiments, the position measurements measured from the intrabody probe are measured using remote electrical field imaging.

In some embodiments, the method further comprises: receiving an indication of a position inside a lumen defined by the curved body tissue surface and located away from the curved body surface; and transforming the position into 3-D coordinates of the flattened 3-D model; wherein the image produced includes an indication located at the transformed position.

In some embodiments, a plurality of images are produced from the flattened 3-D model, wherein a first image is a view of the flattened 3-D model from a first direction, a second image is a view of the flattened 3-D model from a second direction, and the first and second images show different sides of a same surface portion.

In some embodiments, the method comprises producing an image from the flattened 3-D model showing both a portion of an internal side and a portion of an external side of a surface represented in the flattened 3-D model.

In some embodiments, a straight linear region extending from one edge of the flattened 3-D model to another edge of the flattened 3-D model distorts distances relative to the source 3-D model by substantially the same amount through the linear region.

In some embodiments, the amount of distortion along the linear region is adjustable by user selection.

There is provided, in accordance with some embodiments of the present disclosure, a system for displaying a curved body tissue surface, the system comprising: computer circuitry configured to transform a computer memory-stored source 3-D model of the curved body tissue surface into computer memory-stored flattened 3-D model comprising relief details of the body tissue surface represented as relative differences in depth over an unwrapped and flattened surface extent; and a display, configured to receive and display an image of the flattened 3-D model, produced by the computer circuitry from the flattened 3-D model.

In some embodiments, the flattened 3-D model is transformed to have width, length, and depth.

In some embodiments, the relief details are represented in depth; and the width and length correspond to spherical angle positions in the source 3-D model.

In some embodiments, the flattened 3-D model also represents transformed positions from the volume of the source 3-D model away from the curved body tissue surface.

In some embodiments, the flattened 3-D model introduces a discontinuity between two portions which correspond to two different and adjacent portions of curved body tissue surface.

In some embodiments, the computer circuitry is further comprised to repeatedly produce an image from updated flattened 3-D models transformed from the source 3-D model, while the source 3-D model is repeatedly updated by new data indicating positions of the surface.

In some embodiments, the system includes an intrabody probe configured to provide position indicating measurement to the computer circuitry, wherein the source 3-D model is repeatedly updated using position-indicating measurements measured by the intrabody probe.

In some embodiments, the computer circuitry is further configured to: receive an indication of a position inside a lumen defined by the curved body tissue surface and located away from the curved body surface; and transform the position into 3-D coordinates of the flattened 3-D model; and wherein the image produced includes an indication located at the transformed position.

In some embodiments, a straight linear region extends from one edge of the flattened 3-D model to another edge of the flattened 3-D model which distorts distances relative to the source 3-D model by substantially the same amount through the linear region.

There is provided, in accordance with some embodiments of the present disclosure, a method comprising: receiving data indicative of electrical measurements inside a body cavity; mapping the electrical measurements to locations inside the body cavity; reconstructing from the locations inside the body cavity a shape of an inner surface of the body cavity; and presenting substantially the entire shape of the inner surface of the body cavity for viewing within a single view.

In some embodiments, the method comprises repeating the reconstructing and presenting during the mapping, wherein the single view is updated during the repeating by new data from the mapping indicating locations of the inner surface.

In some embodiments, the new data from the mapping is measured from an intrabody probe, as the intrabody probe is moved within the body cavity.

In some embodiments, the method further comprises: receiving an indication of a position located away from the inner surface; and transforming the position into a transformed position within the single view; wherein the single view includes an indication located at the transformed position.

In some embodiments, the indication is an indication of a probe position within the body cavity.

In some embodiments, the single view shows both a portion of an internal side and a portion of an external side of the inner surface.

In some embodiments, a straight linear region extending from one edge of the single view to another edge of the single view distorts distances relative to the shape of the inner surface by substantially the same amount through the linear region.

There is provided, in accordance with some embodiments of the present disclosure, a system comprising computer circuitry configured to: receive data indicative of electrical measurements inside a body cavity; map the electrical measurements to locations inside the body cavity; reconstruct from the locations inside the body cavity a shape of an inner surface of the body cavity; and present, using a display, substantially the entire shape of the inner surface of the body cavity for viewing within a single view.

There is provided, in accordance with some embodiments of the present disclosure, a method of representing a curved body tissue surface by a data structure stored in computer memory, the method comprising: receiving a source 3-D model comprising a data structure stored in computer memory representing in three dimensions a surface shape isomorphic with: relief details superimposed upon a reference surface shape curving around a point interior to the 3-D surface, wherein the relief details superimpose relative differences in radial offset from the interior point; isolating the relief details of the source 3-D model from the reference surface shape; and using the isolated relief details to produce a three dimensional surface comprising a flattened 3-D model transformed from the source 3-D model.

In some embodiments, the method comprises producing an image from the flattened 3-D model.

In some embodiments, shapes of the relief details represented in the flattened 3-D model are distorted compared to their representation in the source 3-D model.

In some embodiments, the reference surface shape, from which the relief details are isolated, is also stored in computer memory.

In some embodiments, the method comprises repeating a plurality of performances of the receiving and isolating, wherein the source 3-D model is updated during the repeating by new data indicating positions of the surface.

In some embodiments, the source 3-D model is updated with position measurements measured from an intrabody probe moving near the curved body tissue surface.

In some embodiments, the position measurements measured from the intrabody probe are measured using measurements of one or more electrical fields established where the intrabody probe is moving.

In some embodiments, the position measurements measured from the intrabody probe are measured using remote electrical field imaging.

There is provided, in accordance with some embodiments of the present disclosure, a method of indicating the position of a probe within a lumenal space of a body, comprising: transforming a source 3-D representation of the lumenal space into a flattened representation, wherein the flattened representation comprises representation of at least 80% of total spherical angular extent relative to an origin within the source 3-D representation; and displaying the flattened representation together with an indication of a position of the probe with respect to the flattened representation, to indicate a position of the probe within the lumenal space.

In some embodiments, the flattened representation is defined within a 3-D space having width, length, and depth, and the indicated probe position is defined within the width, length, and depth of the 3-D space.

In some embodiments, the indicated position of the probe includes an indication of the distance of the probe from a surface of the lumenal space indicated in the flattened representation.

In some embodiments, the indication of distance comprises a marker displayed on the surface of the flattened representation.

In some embodiments, the indication of distance comprises a position of a simulated intersection of a line continuing from the probe at the indicated position and at an indicated orientation with the surface of the flattened representation.

In some embodiments, the method comprises: receiving from a user an indication of a portion of a wall of the lumenal space; and transforming the 3-D representation of the lumenal space into a flattened display representation selectively preserving representation of 3-D distances along the selected portion of the wall of the lumenal space, compared to another portion of the wall.

There is provided, in accordance with some embodiments of the present disclosure, a flattened visual representation of surfaces surrounding a lumenal space of a body, suitable for simultaneous display of all its parts on a flat surface; wherein the flattened visual representation represents at least 80% of the angular extent subtended by the surrounding surfaces; and comprising a target region of at least 15% of the flattened visual representation; wherein average distance distortion per unit area measured relative to a reference size located within the target region is larger outside the target region than inside the target region, by a ratio of at least 4:1.

There is provided, in accordance with some embodiments of the present disclosure, a method of using the flattened visual representation described above, comprising showing a representation of an intra-body probe over a surface represented by the flattened visual representation to which the intra-body probe is currently closest.

In some embodiments, the target region comprises a plurality of regions unconnected by any contiguous path extending only through the target region.

In some embodiments, the lumenal space comprises a left atrium.

In some embodiments, the target region comprises at least one region surrounding a root of a pulmonary vein.

In some embodiments, the target region comprises a region entirely surrounding roots of all the pulmonary veins of the left atrium.

There is provided, in accordance with some embodiments of the present disclosure, a method of finding an orientation of a surface reconstruction, comprising: receiving the surface reconstruction, including relief details of the surface at a range of depths; assigning weightings to positions on the surface reconstruction, based on the depths of the relief details; and determining an orientation of the surface reconstruction, using at least one criterion for a distribution of weightings applied to the assigned weightings.

In some embodiments, the surface reconstruction comprises relief details for production of a flattened 3-D model according to the method of claim 1.

In some embodiments, the surface reconstruction comprises relief details for production of a flattened 3-D model according to the method of claim 7.

In some embodiments, at least one discontinuity is introduced into the flattened 3-D model based on the determined orientation.

In some embodiments, the surface reconstruction comprises relief details of a flattened 3-D model produced according to the method.

In some embodiments, the method comprises producing a view of the flattened 3-D model, wherein at least one discontinuity is introduced into the view based on the determined orientation.

There is provided, in accordance with some embodiments of the present disclosure, a system for producing a display of a curved body tissue surface, the system comprising a computer processor configured to carry out processor instructions to: receive a source reconstruction representing in three dimensions a surface comprising relief details distributed around a global curvature; flatten the source reconstruction to produce a flattened 3-D model representing the in three dimensions the relief details along a surface with reduced global curvature; and produce an image from the flattened 3-D model.

There is provided, in accordance with some embodiments of the present disclosure, a method of indicating the position of a probe within a lumenal space of a body, comprising: transforming a 3-D representation of view of the lumenal space into a flattened display representation, wherein the flattened display representation comprises representation of at least 80% of total 3-D angular extent relative to a 3-D origin within the lumenal space; and indicating a position of the probe within the flattened representation.

According to some embodiments of the present disclosure, the indicated position of the probe includes an indication of the distance of the probe from a surface of the lumenal space indicated in the flattened representation.

According to some embodiments of the present disclosure, the indication of distance comprises a marker displayed on the surface of the lumenal space.

According to some embodiments of the present disclosure, the indication of distance comprises a position of a simulated intersection of a line continuing the probe with the surface of the lumenal space.

According to some embodiments of the present disclosure, the transformation selectively preserves representation of 3-D distances along a selected portion of a wall of the lumenal space, compared to another portion of the wall; and wherein the selected portion of the wall is pre-defined based on targeting of the portion for treatment, and the flattened display representation is fixed while the indicated position of the probe changes.

According to some embodiments of the present disclosure, the flattened display representation comprises a geometrical transformation by projection of a 3-D object onto a curved 2-D surface, wherein the 2-D surface is shown flattened in the flattened display representation.

There is provided, in accordance with some embodiments of the present disclosure, a method of providing a navigational display indicating the position of a probe within a lumenal space of a body, comprising switching between a display comprising a flattened projection of a 3-D space to a curved surface, and a projection of a 3-D space to a planar surface.

There is provided, in accordance with some embodiments of the present disclosure, a flattened visual representation of surfaces surrounding a lumenal space of a body, suitable for simultaneous display of all its parts on a flat surface; wherein the flattened visual representation represents at least 80% of the angular extent subtended by the surrounding surfaces; and comprising a target region of at least 15% of the flattened visual representation; wherein average distance distortion per unit area measured relative to a reference size located within the target region is larger outside the target region than inside the target region, by a ratio of at least 4:1.

There is provided, in accordance with some embodiments of the present disclosure, a method of using the flattened visual representation described above, comprising showing a representation of an intra-body probe over a surface represented by the flattened visual representation to which the intra-body probe is currently closest.

According to some embodiments of the present disclosure, the target region comprises a plurality of regions unconnected by any contiguous path extending only through the target region.

According to some embodiments of the present disclosure, the lumenal space comprises a left atrium.

According to some embodiments of the present disclosure, the target region comprises at least one region surrounding a root of a pulmonary vein.

According to some embodiments of the present disclosure, the target region comprises a region entirely surrounding roots of all the pulmonary veins of the left atrium.

There is provided, in accordance with some embodiments of the present disclosure, a method of displaying a curved body tissue surface, the method comprising: receiving a source reconstruction representing in three dimensions a surface comprising relief details distributed around a global curvature; flattening the source reconstruction to produce a flattened reconstruction representing the relief details along a surface with reduced global curvature; and producing an image from the flattened reconstruction.

In some embodiments, the flattening produces a flattened reconstruction having width, length, and depth, wherein the relief details are represented in depth, and the width and length correspond to spherical angle positions in the source reconstruction.

In some embodiments, the body tissue surface comprises an inner lumen surface of a body cavity.

In some embodiments, the source reconstruction represents at least 270° of the inner lumen surface.

In some embodiments, the body cavity comprises a heart left atrium.

In some embodiments, at least one of the features from the group consisting of a heart left atrial appendage ridge, trans-septal, and mitral valve leaflet is represented in the flattened reconstruction.

In some embodiments, the body cavity comprises a heart right atrium.

In some embodiments, at least one of the features from the group consisting of a Thebesian valve, Eustachian valve, tricuspid valve leaflet, and a coronary sinus is represented in the flattened reconstruction.

In some embodiments, the body tissue surface comprises an interior surface of a body lumen.

In some embodiments, the produced image represents at least 80% of the interior surface of the body lumen.

In some embodiments, the flattening comprises introducing a discontinuity to the flattened reconstruction.

In some embodiments, the flattening comprises converting a representation of the source reconstruction in spherical coordinates into Cartesian coordinates to produce the flattened reconstruction.

In some embodiments, the body tissue surface comprises at least one of the group consisting of a heart chamber, blood vessel, lymph vessel, bone, membrane, cyst, gastrointestinal tract portion, kidney/urinary tract portion, respiratory tract portion, reproductive tract portion, eye, ear, CNS ventricle, and peritoneum.

In some embodiments, the method comprises iterating over a plurality of performances of the receiving, flattening, and producing, using a source reconstruction which is updated during the iterating by new data indicating positions of the surface.

In some embodiments, the source construction is interactively updated with position measurements of the surface measured from an intrabody probe, as the intrabody probe is moved within a lumen defined by the surface.

In some embodiments, the position measurements measured from the intrabody probe are measured using remote electrical field imaging.

There is provided, in accordance with some embodiments of the present disclosure, a method of representing a curved body tissue surface by a data structure stored in computer memory, the method comprising: receiving a source reconstruction comprising a data structure stored in computer memory representing in three dimensions a global curvature of the curved body tissue surface, together with relief details distributed along the global curvature; isolating relief details of the source reconstruction from a global curvature of the source reconstruction; and producing a flattened reconstruction comprising a data structure stored in computer memory representing in three dimensions the isolated relief details.

In some embodiments, the method comprises producing an image from the flattened reconstruction.

In some embodiments, data structure of the flattened reconstruction stored in computer memory is one of a plurality of partial representations in three dimensions of the isolated relief details, produced separately and intermediately as part of the producing an image.

In some embodiments, shapes of the relief details represented in the flattened reconstruction are altered compared to their representation in the source reconstruction.

In some embodiments, the global curvature from which the relief details are isolated is also stored in computer memory.

In some embodiments, the method comprises iterating over a plurality of performances of the receiving, flattening, and producing, using a source reconstruction which is updated during the iterating by new data indicating positions of the surface.

In some embodiments, the source construction is updated with position measurements measured from an intrabody probe.

In some embodiments, the position measurements measured from the intrabody probe are measured using remote electrical field imaging.

There is provided, in accordance with some embodiments of the present disclosure, a method of indicating the position of a probe within a lumenal space of a body, comprising: transforming a source 3-D representation of the lumenal space into a flattened representation, wherein the flattened representation comprises representation of at least 80% of total spherical angular extent relative to an origin within the source representation; and displaying the flattened representation together with an indication of a position of the probe with respect to the flattened representation, to indicate a position of the probe within the lumenal space.

In some embodiments, the flattened representation is defined within a 3-D space having width, length, and depth, and the indicated probe position is defined within the width, length, and depth of the 3-D space.

In some embodiments, the indicated position of the probe includes an indication of the distance of the probe from a surface of the lumenal space indicated in the flattened representation.

In some embodiments, the indication of distance comprises a marker displayed on the surface of the flattened representation.

In some embodiments, the indication of distance comprises a position of a simulated intersection of a line continuing from the probe at the indicated position and at an indicated orientation with the surface of the flattened representation.

In some embodiments, the method comprises: receiving from a user an selection indicating a portion of a wall of the lumenal space; and transforming the 3-D representation of view of the lumenal space into a flattened display representation selectively preserving representation of 3-D distances along the selected portion of the wall of the lumenal space, compared to another portion of the wall.

There is provided, in accordance with some embodiments of the present disclosure, a flattened visual representation of surfaces surrounding a lumenal space of a body, suitable for simultaneous display of all its parts on a flat surface; wherein the flattened visual representation represents at least 80% of the angular extent subtended by the surrounding surfaces; and comprising a target region of at least 15% of the flattened visual representation; wherein average distance distortion per unit area measured relative to a reference size located within the target region is larger outside the target region than inside the target region, by a ratio of at least 4:1.

There is provided, in accordance with some embodiments of the present disclosure, a method of using the flattened visual representation described above, comprising showing a representation of an intra-body probe over a surface represented by the flattened visual representation to which the intra-body probe is currently closest.

In some embodiments, the target region comprises a plurality of regions unconnected by any contiguous path extending only through the target region.

In some embodiments, the lumenal space comprises a left atrium.

In some embodiments, the target region comprises at least one region surrounding a root of a pulmonary vein.

In some embodiments, the target region comprises a region entirely surrounding roots of all the pulmonary veins of the left atrium.

There is provided, in accordance with some embodiments of the present disclosure, a method of finding an orientation of a reconstruction of a surface, comprising: receiving the surface reconstruction, including relief details of the surface at a range of depths; assigning weightings to positions on the surface reconstruction, based on the depths of the relief details; and determining an orientation of the surface reconstruction, using at least one criterion for a distribution of weightings applied to the assigned weightings.

In some embodiments, the surface reconstruction comprises relief details for production of a flattened reconstruction according to the method of claim 1.

In some embodiments, the surface reconstruction comprises relief details for production of a flattened reconstruction according to the method of claim 7.

In some embodiments, at least one discontinuity is introduced into the flattened reconstruction based on the determined orientation.

In some embodiments, the surface reconstruction comprises relief details of a flattened reconstruction produced according to the method of claim 1.

In some embodiments, at least one discontinuity is introduced into the view based on the determined orientation.

There is provided, in accordance with some embodiments of the present disclosure, a system for producing a display of a curved body tissue surface, the system comprising a computer processor configured to carry out processor instructions to: receive a source reconstruction representing in three dimensions a surface comprising relief details distributed around a global curvature; flatten the source reconstruction to produce a flattened reconstruction representing the relief details along a surface with reduced global curvature; and produce an image from the flattened reconstruction.

There is provided, in accordance with some embodiments of the present disclosure, a method of indicating the position of a probe within a lumenal space of a body, comprising: transforming a 3-D representation of view of the lumenal space into a flattened display representation, wherein the flattened display representation comprises representation of at least 80% of total 3-D angular extent relative to a 3-D origin within the lumenal space; and indicating a position of the probe within the flattened representation.

According to some embodiments of the present disclosure, the indicated position of the probe includes an indication of the distance of the probe from a surface of the lumenal space indicated in the flattened representation.

According to some embodiments of the present disclosure, the indication of distance comprises a marker displayed on the surface of the lumenal space.

According to some embodiments of the present disclosure, the indication of distance comprises a position of a simulated intersection of a line continuing the probe with the surface of the lumenal space.

According to some embodiments of the present disclosure, the transformation selectively preserves representation of 3-D distances along a selected portion of a wall of the lumenal space, compared to another portion of the wall; and wherein the selected portion of the wall is pre-defined based on targeting of the portion for treatment, and the flattened display representation is fixed while the indicated position of the probe changes.

According to some embodiments of the present disclosure, the flattened display representation comprises a geometrical transformation by projection of a 3-D object onto a curved 2-D surface, wherein the 2-D surface is shown flattened in the flattened display representation.

There is provided, in accordance with some embodiments of the present disclosure, a method of providing a navigational display indicating the position of a probe within a lumenal space of a body, comprising switching between a display comprising a flattened projection of a 3-D space to a curved surface, and a projection of a 3-D space to a planar surface.

There is provided, in accordance with some embodiments of the present disclosure, a flattened visual representation of surfaces surrounding a lumenal space of a body, suitable for simultaneous display of all its parts on a flat surface; wherein the flattened visual representation represents at least 80% of the angular extent subtended by the surrounding surfaces; and comprising a target region of at least 15% of the flattened visual representation; wherein average distance distortion per unit area measured relative to a reference size located within the target region is larger outside the target region than inside the target region, by a ratio of at least 4:1.

There is provided, in accordance with some embodiments of the present disclosure, a method of using the flattened visual representation described above, comprising showing a representation of an intra-body probe over a surface represented by the flattened visual representation to which the intra-body probe is currently closest.

According to some embodiments of the present disclosure, the target region comprises a plurality of regions unconnected by any contiguous path extending only through the target region.

According to some embodiments of the present disclosure, the lumenal space comprises a left atrium.

According to some embodiments of the present disclosure, the target region comprises at least one region surrounding a root of a pulmonary vein.

According to some embodiments of the present disclosure, the target region comprises a region entirely surrounding roots of all the pulmonary veins of the left atrium.

There is provided, in accordance with some embodiments of the present disclosure, a system for displaying an image of a heart chamber, the system comprising: field generating electrodes configured to generate electrical fields in the heart chamber; field measuring electrodes configured to measure at least one parameter of the electrical fields in the heart chamber; an interface configured to allow a user to indicate a region of interest; computer circuitry configured to: generate the image of the heart chamber based on input received from the field measuring electrodes; and a display configured to display the image; wherein the computer circuitry is configured to generate the image showing the inner surface of the heart chamber as if it is viewed from a virtual camera viewpoint positioned inside the heart chamber, having a field of view covering at least 80% of the inner surface of the heart chamber, and looking towards the region of interest.

There is provided, in accordance with some embodiments of the present disclosure, a system for displaying an image of a heart chamber as viewed from a virtual camera viewpoint, the system comprising: field generating electrodes configured to generate electrical fields in the heart chamber; field measuring electrodes configured to measure at least one parameter of the electrical fields in the heart chamber; an interface configured to allow a user to indicate for the virtual camera viewpoint a position, a looking direction, or both a position and a looking direction; computer circuitry configured to: generate the image of the heart chamber based on input received from the field measuring electrodes; and a display configured to display the image; wherein the computer circuitry is configured to generate the image showing the inner surface of the heart chamber as if it is viewed from a virtual camera viewpoint having a field of view that covers at least 80% of the inner wall of the heart chamber, positioned in the position indicated via the interface, and looking at the looking direction indicated via the interface.

There is provided, in accordance with some embodiments of the present disclosure, a system for displaying an image of a heart chamber as viewed by a virtual camera viewpoint, the system comprising: field generating electrodes configured to generate electrical fields in the heart chamber; field measuring electrodes configured to measure at least one parameter of the electrical fields in the heart chamber; an interface configured to allow a user to indicate at least one of the members of the group consisting of a cutting line, a position of the virtual camera viewpoint, and a looking direction of the virtual camera viewpoint; computer circuitry configured to: generate the image of the heart chamber based on input received from the field measuring electrodes; and a display configured to display the image; wherein the computer circuitry is configured to generate the image showing the inner surface of the heart chamber as if the heart chamber is cut along the cutting line, unrolled to fit to a 2-dimensional frame, and viewed from a virtual camera viewpoint positioned in the position indicated via the interface, and looking at the looking direction indicated via the interface, and having a field of view that covers, when looking from the position at the direction, at least 80% of the unrolled wall of the heart chamber.

There is provided, in accordance with some embodiments of the present disclosure, a system for displaying an image of a heart chamber, the system comprising: a plurality of electrodes configured to generate electrical field in the heart chamber; a plurality of electrodes configured to measure at least one parameter of the electrical fields inside the heart chamber; an interface configured to allow a user to indicate a region of interest; computer circuitry configured to: generate the image of the heart chamber based on input received from at least a plurality of the electrodes; and a display configured to display the image; wherein the image shows the inner surface of the heart chamber as if it is viewed by a viewer positioned inside the heart chamber, having a field of view that covers the entire inner surface of the heart chamber, and looking towards the region of interest.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system" (e.g., a method may be implemented using "computer circuitry"). Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 14A-14E schematically illustrate different 3-D examples of pre-flattening and post-flattening global curvatures and relief details, according to some embodiments of the present disclosure.

FIG. 16A illustrates a triangular meshing of the shape of a left atrium, according to some embodiments of the present disclosure;

FIGS. 16B-16E illustrate different flattenings of the triangular meshing of FIG. 16A, according to some embodiments of the present disclosure.

Figure 1A:
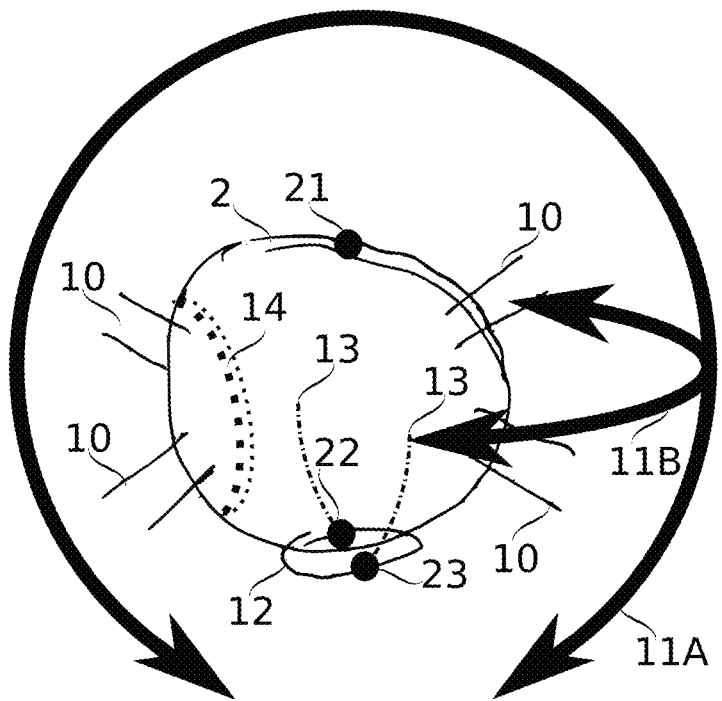
FIG. 1A schematically represents anatomical features of a left atrium represented in its usual 3-D shape, according to some embodiments of the present disclosure.

DESCRIPTION OF SPECIFIC EMBODIMENTS
OF THE INVENTION

The present invention, in some embodiments thereof, relates to the field of medical procedures using intrabody probes navigable within intrabody spaces, and more particularly, to presentation of data acquired during the course of a catheter procedure.

Overview

An aspect of some embodiments of the present invention relates to methods and system for the displaying of flattened representations of tissue surfaces; and in particular embodiments, displays of flattened representations of the interior surfaces of hollow organs (body cavities). Surfaces are optionally presented from one or both of their two sides: e.g., a represented interior surface of a hollow organ may be presented for viewing from an external side or an internal side of the surface (also referred to herein as "epicardial" and "endocardial" views, respectively). From some viewing angles, a portion of an external view of the internal surface may be viewed along with a portion of an internal view of the internal surface. In some embodiments, exterior tissue surfaces are represented.

In some embodiments, data comprising a 3-D representation (that is, a representation having width, length, and depth) of a curved body tissue surface (e.g., a surface of a body organ or portion thereof) are subject to a geometrical transformation which results in a different representation, which is also 3-D (having width, length and depth), but is potentially better suited to display of the organ surface and optionally a volume defined thereby, substantially within a single view. Herein, the result obtained by such a transformation is referred to as a "flattened reconstruction". A "reconstruction," "3-D representation" or "3-D model" of a shape, as the terms are used interchangeably herein, comprises a data structure stored in computer memory specifying 3-D coordinates of positions defining a surface of the shape.

Moreover, the reconstruction (3-D representation, 3-D model) may be "flattened". This is also referred to herein as "curvature-straightened", "relatively straightened", and "unrolled". Also herein, "reduction" of curvature refers to making a curvature relatively straighter and/or more gradual. In the case of flattened 3-D models, the flattening is in the sense that a surface of the first (or "source") 3-D representation which curves to extend around some reference point and/or path is converted (in the second/modified or "flattened" 3-D representation) to a relatively straightened surface. The transformation is performed so that while a global curvature is relatively straightened (reduced) by the flattening, relief details distributed along the curved surface are retained. Moreover, in some embodiments, the flattening is done so that other positions in the volume of the source 3-D model away from the surface are also transformed, and have corresponding positions within the flattened 3-D representation. In some embodiments, the transformation is 1:1, so that positions in the flattened 3-D model uniquely correspond to positions in the source 3-D model. This may be contrasted, for example, with a 2-D image projected from a source 3-D model, which collapses representation through a range of positions in depth to a single pixel or other 2-D image region. The flattened 3-D model may, however, be converted in turn to an image, such as a 2-D image for viewing. A potential advantage of the intermediate flattened 3-D model, over direct projection of a source 3-D model to an image, is in allowing the surface to be presented in substantially its entirety, while its features retain properties under changes in viewing perspective (e.g., changes of a virtual camera's vantage point) that correspond to how objects normally behave in the visual field of an observer. This may assist a person viewing the changing image to maintain a sense of feature persistence. For example, changes in foreshortening, size, and/or mutual masking behave much as any normal object in the ordinary visual field behaves, so that the relationship among various parts of the flattened 3-D model remains visually clear. In contrast, changing the viewing perspective of a fisheye lens type view (e.g., a view that projects $2\pi$ steradians or more of solid angle view onto a 2-D image) results in patterns of changing distortion (radial compression as features come near the image rim, in particular) which are potentially more disorienting. This may interfere with recognition of features, and/or recognition of features as being the same feature, as the viewing perspective changes. In some embodiments, images generated from the flattened 3-D model are used in real-time applications, e.g., visualization of the navigation of a probe within the modeled space by the placing of an indication at a position within the flattened 3-D model which converts, when an image is made from the flattened 3-D mode, to an indication of the probe position relative to other features in the flattened 3-D model. In better matching the normal behavior of visual objects, the images may potentially help a user to maintain a sense of orientation in the space being navigated.

Optionally, the global curvature targeted for straightening by the flattening is defined by a function such as a sphere, ellipsoid, parametric curve (e.g., Bézier curve), combination of spherical harmonics, and/or long wavelength frequency domain components of a Fourier transform of the surface transformed back into the spatial domain. A surface defined by such a function is also referred to herein as a "surface of global curvature". In some embodiment, the global curvature is at least partially implicit in the choices of coordinate systems used during flattening; for example, in some embodiments, a spherical global curvature is implicit in the choice of a transform that comprises conversion of coordinate values in a spherical coordinate system directly into coordinate values of a Cartesian coordinate system. Herein, the flattening transformation is also referred to as "unwrapping". The term arises in the sense that a surface which curves around some central region in a source 3-D model "wraps around" that central region; and when the flattened 3-D model is created, the same surface is effectively flattened so that the central region is no longer enclosed by it. It should be understood, however, that other regions in the volume of the source 3-D model away from the unwrapped surface are also transformed by the "unwrapping" in some embodiments of the invention.

The relief details comprise, e.g., details having distances from the reference point which vary separately from the surface of global curvature. For example, depths of the relief details may add linearly to depths of the global curvature in spherical coordinates or in another coordinate system. The selection of a global curvature for production of the flattened reconstruction (and/or selection of a method of modeling global curvature) is optionally influenced by the structure of reconstruction details (the relief details) which are to be preserved or suppressed: for example, scale and/or shape. Insofar as the global curvature follows the shape of some detail in the source reconstruction, that detail will tend to be suppressed in the flattened reconstruction.

The relief details which are represented by their depth in the flattened reconstruction and/or a view thereof are optionally distorted (at least in some places) by some amount in the dimensions of width, length, and/or depth; for example as a by-product of the transformation used to produce the flattened reconstruction. In some embodiments, width and length in the flattened reconstruction correspond to spherical angle positions in the source reconstruction.

Optionally (e.g., when the source reconstruction substantially surrounds the reference point), the flattening comprises introducing one or more discontinuities, for example "cuts" in the flattened reconstruction compared to the source reconstruction. Optionally, discontinuities are suppressed in the flattened reconstruction and/or a view thereof by duplication, for example, by concatenation of data from another portion of the reconstruction (optionally with reflection or another manipulation) at the edges of discontinuities. Additionally or alternatively, insofar as the flattened reconstruction itself per se is (and/or is part of) a data structure in computer memory, it is not necessarily bound by the limitations of 3-D space. In particular, there is no necessarily inherent contradiction in the flattened reconstruction being represented in memory as both flattened and circumferentially continuous in all directions (e.g., structured as one or more circular linked lists, giving the data structure spherical, toroidal, infinite planar, or another type of logically continuous topology). However, at some stage during preparation of a viewable image, at least one discontinuity will generally be introduced so that the image itself can be flat, or at least contained within a limited viewing angle (in contrast, for example, to an immersive and 360-degree, $4\pi$ steradians surrounding image such as may be obtained using some virtual reality display devices). For convenience of discussion, the examples herein assume that cuts are introduced during the procedure of producing the flattened reconstruction. In some embodiments, the discontinuity is introduced such that it separates (by being introduced between) two portions of the flattened 3-D model which correspond to two different and adjacent portions of the curved body tissue surface before the transformation.

The resulting flattened reconstruction, and/or a view thereof may be considered as "quasi 2-D"; with the understanding that "quasi" indicates that a 3-D representation of relative feature depth (e.g., distance from a reference point) is retained.

In some embodiments, a "view" of a flattened reconstruction comprises a 2-D or 3-D image showing the flattened reconstruction. The view is optionally considered as either of the image as such (e.g., a digital image in computer memory), and a display and/or other representation (e.g., a printout and/or 3-D printed object) of the image.

It is noted that the flattened reconstruction may, in some embodiments, be produced piecewise as a set of intermediate results by applying a function iteratively to portions (e.g., individual data points) of the source reconstruction, e.g., in the course of producing an image or another view showing the flattened reconstruction. In such embodiments, the flattened reconstruction is not necessarily stored in computer memory all at once. For purposes of the descriptions and claims herein, the aggregate of intermediate results in such embodiments also should be considered as comprising a "flattened reconstruction", and also equivalent to a storage in computer memory of a flattened reconstruction (wherein the scope of the term "computer memory" includes on-board processor registers), albeit optionally serially. Any given intermediate result of producing the flattened reconstruction should also be considered as comprising a "flattened reconstruction" and a storage in computer memory of a flattened reconstruction, albeit a partial one.

The relative flattening, in some embodiments, creates a substantially flat surface (that is, of practically zero curvature, or curvature much smaller than the source reconstruction had). In some embodiments, the flattening retains some global curvature. Optionally, a measure of the flattening may be expressed as an increase in the radius of a sphere which best fits (e.g., minimizes average distance to) the flattened reconstruction, compared to the best-fit sphere for the source 3-D representation of the surface. The radius increase is determined for substantially unchanged sizes of surface features (e.g., the same on average). In some embodiments this radius increase is at least a factor of 2, and preferably at least a factor of 5. Optionally, the best-fit sphere for the source 3-D representation is considered to define the global curvature which is relatively flattened.

The curved body tissue surface extends, in some embodiments, at least 135°, 180°, 270°, and preferably 360° around the reference point. The reference point should be understood near the middle of (e.g., within the central 50% of) a volume around which the curved body tissue extends. For example, for purposes of determining angular extent of the curved surface: the curved surface, in some embodiments, is best-fit by a sphere having a radius smaller than about twice the minimum distance between the surface and the reference point. Additionally or alternatively, the reference point around which the curved surface extends is located within the best-fit sphere having a radius r, at a distance less than r/2 from the center of the best-fit sphere.

In some embodiments of the invention, a flattened reconstruction is flattened over a large region of a complete source reconstruction (e.g., at least 70%, 80%, 90%, 95%, or another fraction of the surface in the source reconstruction—that is, the shape of the surface—optionally covering at least 2π, 2.5π, 3π, 3.5π or 4π steradians of solid angle from a reference location within the source reconstruction). Modeling in the flattened 3-D model may comprise substantially all of the shape of the surface of a body cavity represented in the source 3-D model. The flattened reconstruction view is optionally of the whole flattened reconstruction, and/or of any suitable portion of the flattened reconstruction (e.g., less than 70%, less than 50%, or another fraction). Optionally, the view zooms up to a particular feature such as a pulmonary vein ostium, or even is adjusted to viewpoints from within the relief details (e.g., blood vessels) themselves. In some embodiments, a region within the flattened reconstruction which is particularly targeted for display with low angular and/or distance distortion comprises a plurality of regions (optionally contiguous or separate) spaced from each other (in a corresponding source reconstruction, and with respect to a reference point) by at least 90°, at least 120°, at least 135°, at least 150°, or at least another angle.

In some embodiments, distortion of distances within the targeted region (e.g., in the flattened reconstruction itself, and/or comparing two features of identical size in corresponding views of curved and flattened reconstructions) comprises relative distance distortions of less than about 1%, less than about 3%, less than about 5%, less than about 10%, less than about 8%, or less than another larger, smaller, and/or intermediate number. In some embodiments, distortion of angles within the targeted region (e.g., differences of represented angle for lines running parallel to each other in a corresponding 3-D field of view) comprises angular distortions of less than about 1°, less than about 3°, less than about 5° less than about 8°, less than about 10°, or less than another larger, smaller, and/or intermediate angle. In some embodiments, at least 70%, 80%, 90%, 95%, 98%, or another amount of total angular and/or distance distortion (e.g., relative to a reference size and/or angle chosen from within the target region) is concentrated outside of the target region. In some embodiments, the relative concentration of total angular and/or distance distortion (average distortion per unit area with respect to a reference size and/or angle chosen from within the target region) is in a ratio of at least 4:1, 5:1, 10:1, 20:1, or at least another ratio, with the target area having the smaller relative concentration of distortion compared to regions outside the target area. In some embodiments, the targeted regions themselves subtend (in total area, whether or not contiguous) at least 15%, 25%, 33%, 40%, 50%, or another fraction of the total represented area in the flattened reconstruction view.

In some embodiments, distortion amounts on surfaces in the flattened 3-D model (e.g., amounts of distortion in terms of percent change in size compared to the source 3-D model) are substantially the same (e.g., in terms of percent difference in size) across straight linear regions of the flattened 3-D model, e.g., moving from one side of the model to the other. In some embodiments, a user is given means to manage distortions during flattening; for example, choosing where key positions such as cuts are to be made, and/or A reconstructed curved body tissue surface comprises, for example, an inner surface of a body lumen (e.g., a heart chamber, blood vessel, lymph vessel, bone, membrane, cyst, gastrointestinal tract portion, kidney/urinary tract portion, respiratory tract portion, reproductive tract portion, eye, ear, CNS ventricle, peritoneum, and/or another natural and/or artificial space such as implant surroundings) and the reference point is located near the middle of the reconstructed body lumen. In embodiments disclosed herein, the left atrium is used as an example of a particular hollow organ (body cavity) to which such a visualization method is optionally applied. However, it should be understood that the technique optionally applies, changed as necessary, to the interior of any hollow organ or portion thereof. In some embodiments, a representation of an organ exterior surface (e.g., of a heart, liver, kidney, brain, and/or portion(s) thereof such as a right atrium) is flattened.

In some embodiments, atrial fibrillation is to be treated with ablations in the left atrium (LA), by formation of one or more closed lines of lesions which substantially isolate one or more pulmonary veins (PV) from surrounding cardiac tissue to which they are connected. In a typical procedure, a goal is to isolate all PVs this way. An individual ablation line may encircle one PV, or a plurality of PVs.

Simultaneous viewing of a large portion of a curved surface of a body portion has potential advantages for presenting a unified impression of a region targeted, e.g., for treatment delivery. However, without transformation of a source representation to a flattened representation, gaining such a simultaneous view raises different potential problems.

For example, with respect to ablation treatments of PVs in the LA: when the LA is viewed in 3-D through a typical field-of-view angle (e.g., subtending 60°, 50°, 40°, 30° or less), some variable part of the regions to be isolated may be persistently hidden and/or variably distorted, no matter what view direction is chosen. From vantage points close to the LA wall, target details are potentially out of the field of view. From vantage points far from a target side of the LA wall, but still "within the lumen", some target details may still be out of the field of view, and/or distorted due to curvature of the lumenal wall. With a larger angular field of view, more target details may become apparent, but with increasing distortion near the edges of the field of view—distortion that would potentially change significantly if the center of the field of view was moved. From a vantage point outside the LA (e.g., making a proximal wall transparent so that interior target details of a more distal wall can be seen), some target details may be hidden by the transparency, and/or foreshortened so as to make them difficult to distinguish.

Moreover, simulated lighting used in defining (e.g., rendering to a 2-D image) a view of a reconstruction may include shading (shadow) effects to provide a sense of depth. But shading of a curved surface simulating a fixed light source position may result in some features being relatively over-lit or under-lit, depending on their general position, making comparisons difficult. Changing the light source, on the other hand, can result in dramatic (and potentially disorienting) changes to the appearance of the features.

Practically, in order to ablate around the PVs while maintaining a view of the working area, views from an simulated internal camera vantage point are commonly kept near to a "natural" field of view angle (e.g., 30°-60°, and/or similar to the angular size of the display). The vantage point is rotated to look at new portions of the targeted region as necessary. The number of rotations used under such conditions is typically about 8 times for closing a circle around one PV. In practice, this is commonly carried out by an assistant physician or technologist, who moves the view according to the request of the operating physician. A potential drawback of this method is that it may require extra personnel in the room, with attendant potential extra expense, training requirements, scheduling requirements (e.g., to make sure personnel are available simultaneously), and/or procedure complexity.

An aspect of some embodiments of the present invention relates to the use of displays of flattened representations of body tissue surfaces. The use optionally comprises updating of the flattened representation during mapping using data collected from an intrabody probe, and/or guidance of navigation of the intrabody probe itself, shown moving within a scene (space) comprising the flattened reconstruction.

In some embodiments, a position of an intrabody probe is transformed from source coordinates into a new set of coordinates which are used to indicate a position of the intrabody probe together with a view of the flattened reconstruction.

In some embodiments, a flattened reconstruction and/or one or more views thereof is created and iteratively updated during an interactive procedure that repeats the transformation and image production/display from data acquired while a measurement-making catheter probe is navigated (moved) in the vicinity of the body surface represented, e.g., within a lumen bounded by the body surface.

In some embodiments, the updating comprises changing the flattened reconstruction to include new surface position data, e.g., position data determined using measurements (e.g., electrical, magnetic, and/or ultrasound measurements) made from the catheter probe itself. This inclusion may be implemented by updating the source reconstruction and transforming it to provide an updated flattened representation, and/or by transforming the new data and adding the new data transformed directly to the existing flattened reconstruction. Optionally, updating is automatic and optionally continuous as new position data is acquired. Optionally, updating is manually instigated and/or can be manually paused, e.g., for stability of display during a critical phase of a procedure.

Optionally, indications of events (such as ablation points) and/or measurements other than surface positions (such as functional data) are shown together with the flattened reconstruction, optionally shown updating as new events occur and/or measurements are collected.

In some embodiments, updating is performed using only a portion of available position data. For example, by omitting earlier data, there may optionally be obtained a flattened reconstruction view which indicates a current state of a surface which may have changed over time—such as different blood vessel diameters, changes in heart chamber size due to an arrhythmia, or another changing feature. Optionally, available data is selected for inclusion in the flattened reconstruction using gating, e.g., to a particular phase of respiration and/or heartbeat.

Additionally or alternatively, in some embodiments, the updating comprises changing a view created from the flattened reconstruction, e.g., by changing a view angle, distance, or other viewing parameter. Optionally, view changes occur automatically, for example, in response to events of a catheter procedures such as approaching and/or contacting represented tissue surfaces. Additionally or alternatively, in some embodiments, view changes are manually controlled by an operator.

In some embodiments, showing the surface to be treated in a single, suitably flattened reconstruction view provides a potential advantage by permitting operability of the system by a single operator engaged in navigation of an intrabody probe (e.g., a catheter probe).

Optionally, a view of the flattened reconstruction is defined initially for a procedure, e.g., a procedure performed within a certain body cavity, and after this the whole body cavity surface can be seen at once as navigation within the body cavity is performed using an intrabody probe, without a need for further viewing parameter adjustments (though optionally the flattened reconstruction and view are interactively updated with new data describing the body cavity surface as it becomes available).

Optionally, flattened reconstruction and source reconstruction views are displayed simultaneously during intrabody probe navigation (optionally, just the flattened reconstruction is shown in a view). In some embodiments, shifting between flattened and source views is easily controlled by a single user (e.g., using a foot-pedal, and/or triggered by a position of a catheter probe). The transition is optionally smooth, e.g., comprising "unrolling" from the source reconstruction to the flattened reconstruction, and optionally "rolling" back again. Additionally or alternatively, this may be described as producing views of a series of reconstructions flattened over an range of increasing average radii of curvature. The smooth transition potentially helps to preserve a sense of object constancy.

In some embodiments, triggering of the transition and/or another aspect of the current view is controlled automatically by an algorithm based on current conditions. In some embodiments, a 3-D view is from the viewpoint of the catheter (e.g., so that no part which is about to be treated is hidden from view). In some embodiments, a 3-D view is from a viewpoint facing a site to be treated, does not follow movements of the catheter. The catheter movement, however, may be symbolically represented on the 3-D view. In some embodiments, the site to be treated is marked by the physician on the flattened reconstruction view, and the flattened reconstruction view is switched automatically to a 3-D view facing the marked site, e.g., when the catheter approaches the marked site or when the physician requests such a switch, e.g., by pressing a pedal. Parameters considered in automatically switching between views optionally include, for example, distance from a tissue wall, heading direction, phase of procedure (e.g., between two different sub-lesion ablations within a single ablation line, and/or switching between two different ablation lines).

In some embodiments, for example, a switching algorithm is configured to present the overview of a flattened reconstruction view when a catheter probe is navigated by the user far from a tissue wall, and a 3-D view when the user is near the tissue wall, and/or actively engaged in treatment such as ablation.

In some embodiments, the use of manual view switching by one or more users is monitored, and used as input to train a machine-learning algorithm what view is preferred under different circumstances. Optionally, machine-learning is performed using input from users of different stages of experience, and/or exhibiting different clusters (e.g., statistical clusters based on differences in selected view as a function of probe position and/or other procedure parameters) of use style, so that an operator may be presented with choices of automatic view switching which best suit their own mode of use.

An aspect of some embodiments of the present invention relates to the determination of an orientation of a source reconstruction, optionally in preparation for the production of a flattened reconstruction.

In some embodiments, an anatomical orientation of a reconstruction (e.g., a source reconstruction) is determined, for example as part of the process of producing a flattened reconstruction. This may be useful, for example, when the general anatomical origin of data represented in a source reconstruction is initially known (e.g., the data describe an inner lumen of a left atrium); but there remains unknown, unclear, and/or approximate certain specifics of how the reconstruction is oriented; e.g., with respect to landmark features of the anatomy. Moreover, even when orientation is well-known with respect to some reference coordinate system, variations in individual anatomy can affect what orientation framework is preferable for generating a flattened reconstruction, and/or a display of a reconstruction.

In some embodiments, orientation is determined based on one or more metrics of surface regions, determined from a 3-D representation the surface (optionally either a flattened or un-flattened representation). In some embodiments, the metrics are based on depth and/or distance information. For example, positions more distant from some reference point are given a different (e.g., larger) weight than positions closer to the reference point. The weights are then used in combination with one or more rules in order to determine an orientation. For example, where relatively deep (more distant, and, e.g., receiving more weight) features of interest (and/or clusters thereof) are expected to fall along a common line, a rule may specify that this common line provides an orienting reference. In another example, a rule may specify that a line at a position where weight on two sides is balanced provides another orienting reference. Further rules may apply, for example, to resolving potential ambiguities (e.g., where two or more positions satisfy some criterion). Once the orienting references are determined, they are optionally used for purposes of orienting display of reconstruction views. In some embodiments, positions at which discontinuities (cuts) are to be introduced during the flattening of a source reconstruction are determined based on the orienting references.

The rules defined and used optionally vary according to the characteristic anatomy of different anatomical locations. For example, rules applicable to the left atrium optionally take into account the typical positions and/or clusterings of the pulmonary veins, left atrial appendage, and/or mitral valve. Rules applicable to the right atrium optionally take into account the typical positions and/or clusterings of the superior and inferior vena cava, the coronary sinus, and/or the tricuspid valve.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Flattening of a Reconstruction of a 3-D Lumenal Shape

Reference is now made to FIG. 1A, which schematically represents anatomical features of a left atrium 2 represented in its usual 3-D shape, according to some embodiments of the present disclosure. In FIG. 1A, Left atrium 2 is represented as a globular shape.

Locations of the roots of pulmonary veins 10 and mitral valve 12 are shown. Also represented is ablation line 14, the two halves of which together encircle the roots of the left-most two pulmonary veins 10. The nearer half and further half of ablation line 14 are represented with differently dotted lines.

Figure 1B:
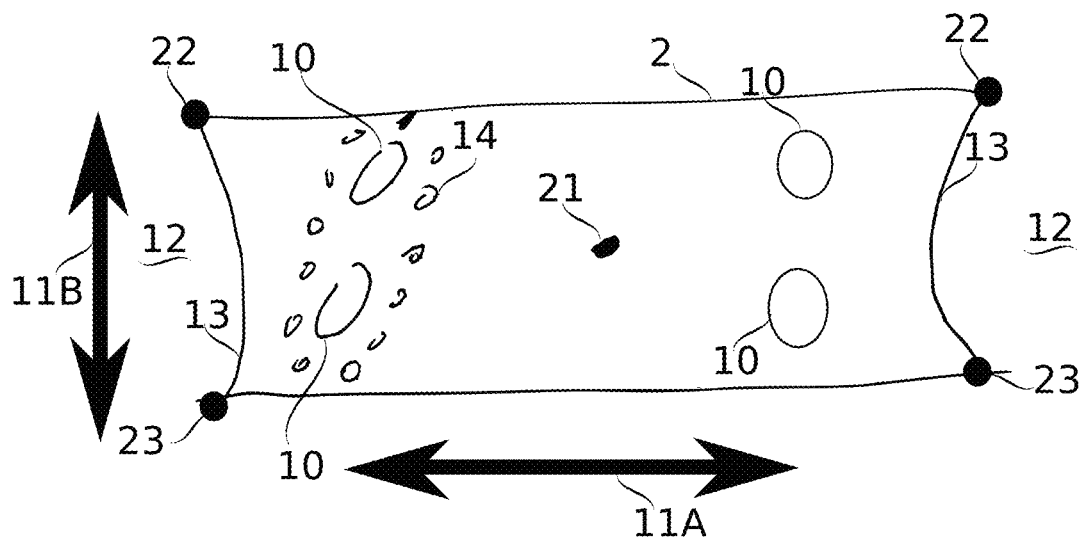
FIG. 1B schematically represents anatomical features of a left atrium spread out into a flattened shape, according to some embodiments of the present disclosure.

Also shown are arrows 11A, 11B and reference points 21, 22 23, further referred to in the descriptions of FIG. 1B.

Figure 1C:
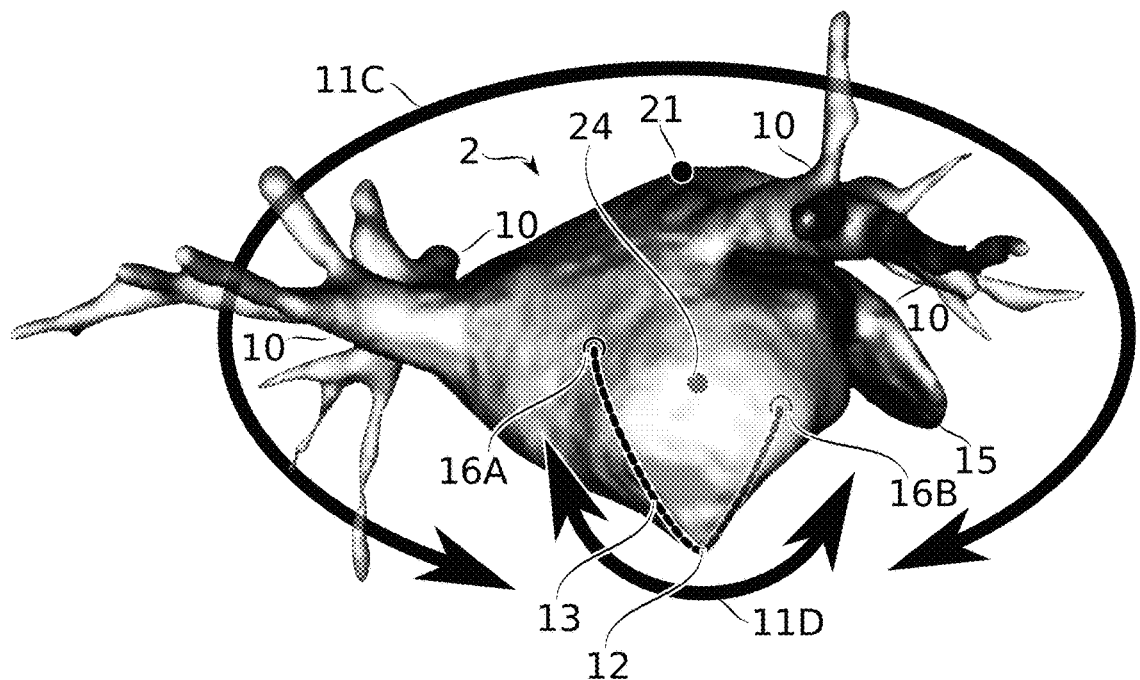
FIG. 1C shows a reconstruction of a left atrium inner lumenal surface represented in its usual (un-flattened) 3-D representation, according to some embodiments of the present disclosure.

Further reference is now made to FIG. 1C, which shows a reconstruction of a left atrium 2 represented in its usual (un-flattened) 3-D shape, according to some embodiments of the present disclosure.

Mitral valve 12 and roots of pulmonary veins 10 are also shown in FIG. 1C, along with left atrial appendage (LAA) 15. Also shown are arrows 11C, 11D, 11E, and reference point 21, which are further referred to in the descriptions of FIG. 1D.

Figure 1D:
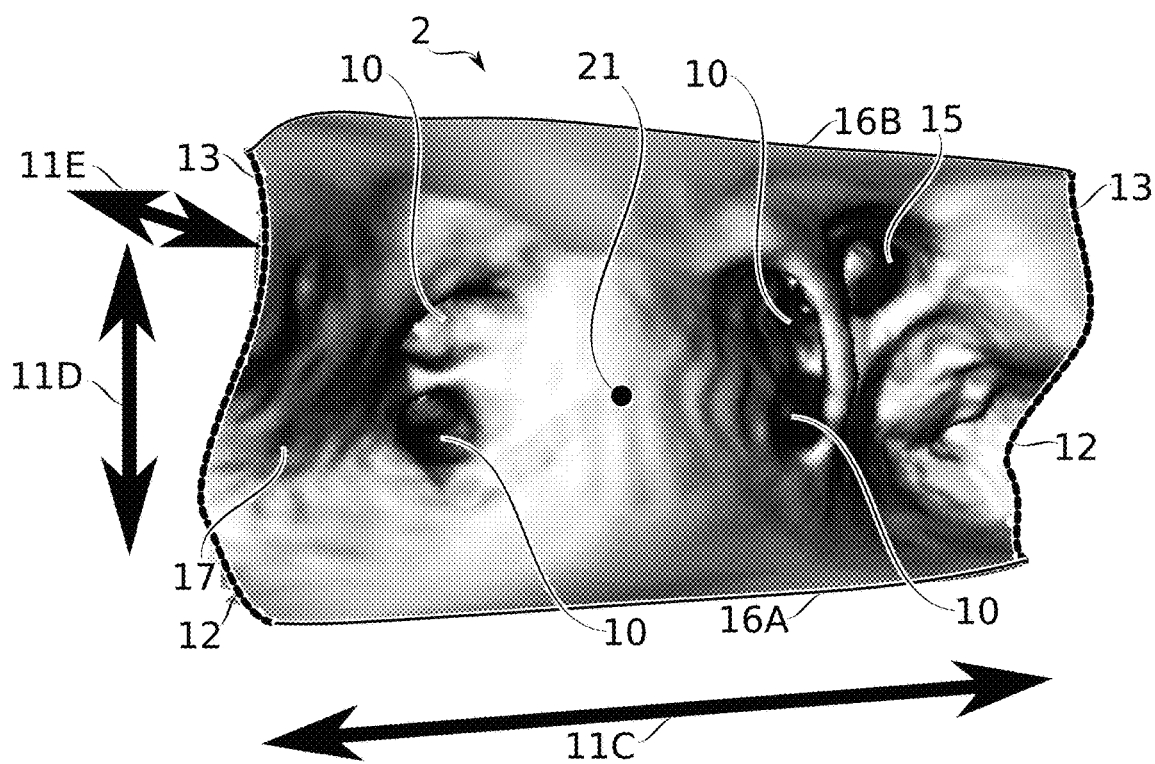
FIG. 1D is a view of a flattened representation of the source reconstruction of FIG. 1C, according to some embodiments of the present disclosure.

FIGS. 1A and 1C indicate lines 13A and 13, respectively, along which the 3-D lumenal shape of left atrium 2 is opened (that is, virtually cut, introducing a discontinuity) to produce the flattened reconstruction views of FIGS. 1B and 1D. It should be noted that Lines 13A and 13 are represented somewhat differently upon flattening, as explained in relation to FIGS. 1B and 1D.

For orientation, reference points 21 of FIG. 1A and FIG. 1C are shown in FIG. 1B and FIG. 1D at the respective center of each flattened reconstruction view.

Reference is now made to FIG. 1B, which schematically represents anatomical features of a left atrium 2 spread out into a flattened shape, according to some embodiments of the present disclosure. FIG. 1B represents a flattened reconstruction view of the atrium 2 of FIG. 1A.

In the flattening transformation used in producing the reconstruction schematically indicated in FIG. 1B, it is approximately as though the left atrium wall was slit partially up the center of the view of FIG. 1A on two sides (e.g., along the lines extending upward from reference points 22 and 23), and unwrapped for viewing. Arrows 11A-11B of FIGS. 1A-1B represent spherical angle coordinates of FIG. 1A mapped to Cartesian axes of FIG. 1B. It should be noted that reference points 22, 23 become the corners of the flattened reconstruction view. The position of the mitral valve 12 is located off the edges of the view, so that the two lateral boundaries of FIG. 1B (extending between points 22 and 23) correspond to the circumference of mitral valve 12. Cut lines 13A are oriented across the top and bottom of the view of FIG. 1B.

In the flattened reconstruction view of FIG. 1B, the entirety of ablation line 14 is now visible at once, and from the same side. This illustrates a potential advantage of the flattened reconstruction view, insofar as more of the interior surface of the left atrium 2 can be seen in a single flattened reconstruction view. Another potential advantage, in some embodiments, is that a catheter probe remains in the image as it moves in the vicinity of any portion of the ablation line, since there is optionally also represented in a view a volume above the flattened reconstruction, into which a representation of the catheter probe may be placed.

Further reference is now made to FIG. 1D, which is a view of a flattened reconstruction flattened from the source reconstruction of FIG. 1C, according to some embodiments of the present disclosure. In FIG. 1D, a slightly different transformation from that of FIG. 1C is used. In this flattened reconstruction, the small regions 16A, 16B of FIG. 1C are stretched along the lower and upper boundaries of the view, while the edges produced by cut 13 extend along the lateral sides of this flattened reconstruction view. Additionally to features such as the mitral valve 12, the pulmonary veins 10, and the left atrial appendage 15, the trans-septal 17 (at the position of the fossa ovalis) is also shown.

It is noted that despite the transformation that "flattens" the reconstruction of FIG. 1C, relative positions in depth of surface positions are retained in the flattened reconstruction. The reconstruction is re-encoding of co-ordinates defining the source 3-D shape, (e.g., the shape displayed in FIG. 1C) to a transformed and flattened 3-D shape (e.g., the shape displayed in FIG. 1D).

Transformation from Source Reconstruction to Flattened Reconstruction

Figure 1E:
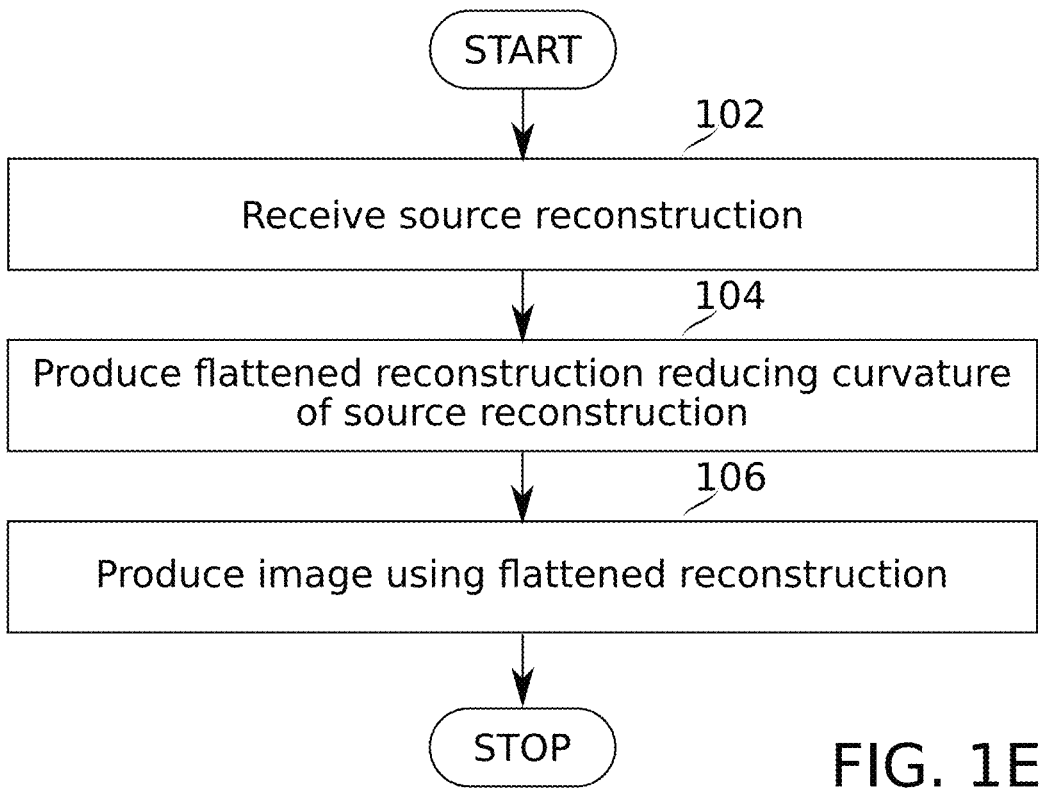
FIG. 1E is a flowchart outlining a method of producing an image of a flattened representation, according to some embodiments of the present disclosure.

Reference is now made to FIG. 1E, which is a flowchart outlining a method of producing an image of a flattened reconstruction, according to some embodiments of the present disclosure.

At block 102, in some embodiments, a source reconstruction comprising a 3-D representation of a curved body tissue surface is received.

At block 104, in some embodiments, a flattened reconstruction is produced from the source reconstruction. The flattened reconstruction is produced so that a global curvature (that is, a curve defined over the area of the curved surface, but not following all its details) is reduced. The global curvature is the curvature of a curve defined over the area of the curved surface, but not following all its details. For example, it may be the curvature of a sphere or of an ellipsoid, best-fitting the curved surface. Optionally, the global curvature is implicit, e.g., in the choice of coordinate systems used in a flattening transformation.

At block 106, in some embodiments, an image is produced using the flattened reconstruction.

Figure 1F:
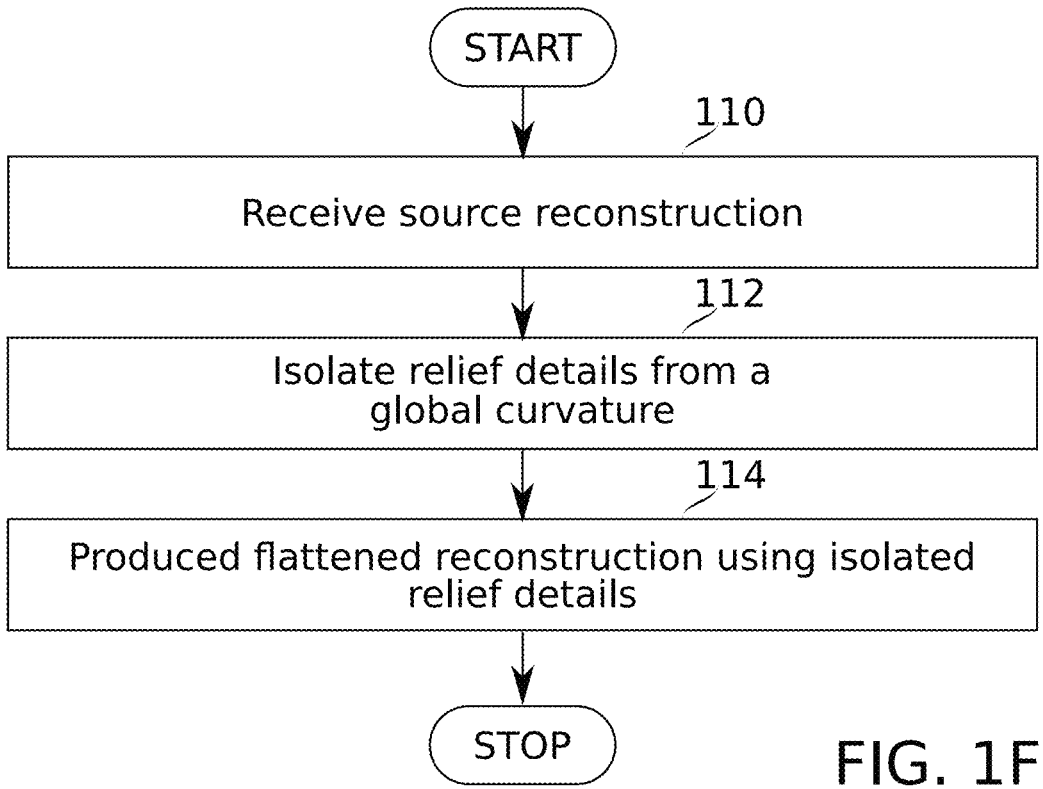
FIG. 1F is a flowchart outlining a method of producing a flattened representation, according to some embodiments of the present disclosure.

Further reference is now made to FIG. 1F, which is a flowchart outlining a method of producing a flattened reconstruction, according to some embodiments of the present disclosure.

At block 110, in some embodiments, a source reconstruction comprising a 3-D representation of a curved body organ surface is received. The source reconstruction may be conceptualized as including a surface (which may be smooth or not) of a global curvature and relief details distributed along the surface of global curvature (e.g., details represented by 3-D positions on the curved body organ surface which are at some distance from a surface representing the surface of global curvature).

At block 112, in some embodiments, the relief details are isolated from the surface of global curvature.

At block 114, in some embodiments, a flattened reconstruction is produced for storage in computer memory, using the isolated relief details. In some embodiments, the computer memory stores the flattened reconstruction as new copies of coordinates of points composing the relief details directly. The coordinates of the points composing the relief details may compose flattened relief details obtainable, in some embodiments, by the flattening transformation described above, e.g., in the context of block 104 of FIG. 1E. Optionally, the global curvature which was flattened out of the source reconstruction to produce the flattened reconstruction is also stored. In some embodiments, what is stored comprises an indication of the transform used to produce the flattened surface of reduced global curvature from the source reconstruction, associated by processor instructions to the source reconstruction. For example, a rendering program is configured to interpret source reconstruction stored as coordinates of $(r, \theta, \varphi)$ as coordinates of $(z, x, y)$.

In some embodiments, FIGS. 1E and 1F comprise alternative descriptions of the same method of producing a flattened reconstruction of a curved body tissue surface.

Input data for producing the source reconstruction optionally comprise data expressed in Cartesian coordinates obtained from 3-D imaging of the patient, for example, CT imaging. Optionally, the data come from another method, for example, using intrabody mapping of positions of a catheter probe (e.g., an electrode probe, magnetic probe, and/or ultrasound probe). In some embodiments, data representing a lumenal wall of a body cavity are obtained using a remote electrical field imaging method, for example a method described in U.S. Provisional Patent Application No. 62/546,775 entitled FIELD GRADIENT-BASED REMOTE IMAGING, and filed Aug. 17, 2017; the contents of which are incorporated herein in their entirety.

In some embodiments, data representing a lumenal wall of a body cavity are obtained using a reconstruction method described in U.S. Provisional Patent Application No. 62/445,433 entitled SYSTEMS AND METHODS FOR RECONSTRUCTION OF INTRA-BODY ELECTRICAL READINGS TO ANATOMICAL STRUCTURE, and filed Jan. 12, 2017; the contents of which are incorporated herein in their entirety. Use of mapping by intra-body probe, e.g., as disclosed in the above two provisional patent applications, provides a potential advantage by allowing data for a flattened reconstruction of a body surface to be collected on the fly (e.g., in real time) as a catheter probe (optionally a standard ablation catheter probe) enters a body region bounded by the body surface. The above cited provisional applications may even provide the ability to collect on the fly data pertaining to structure of regions which have not necessarily been visited by the probe. Optionally, reconstruction is performed using field gradient-based remote imaging, without the use of auxiliary image data.

Use of this surface imaging method provides a potential advantage by allowing data for a flattened reconstruction of a body surface to be collected on the fly (e.g., in real time) as a catheter probe (optionally a standard electrode catheter probe) enters a body region bounded by the body surface, including collection from regions which have not necessarily been visited by the probe. Optionally, reconstruction is performed using field gradient-based remote imaging, without the use of auxiliary image data.

In a first example embodiment of producing a flattened reconstruction, the 3-D representation of the source reconstruction is first encoded (e.g., from Cartesian coordinates) into spherical coordinates; e.g., (x,y,z) coordinates are transformed using a spherical coordinate transform to coordinates expressed as $(r,\theta,\varphi)$, where r is a radius, and $\theta$ and $\varphi$ are spherical angles. This intermediate result comprises a change in coordinate system, without yet introducing a change in the shape of the source reconstruction. Optionally there is a rigid transform applied as part of the conversion, e.g., to set an origin near the center of a lumen defined by the reconstructed surface, and/or to set an orientation along which a discontinuity (cut) will be introduced as part of the flattening.

In some embodiments, to next create the flattened transformation (in overview): the x (horizontal) dimension of the flattened representation is mapped to one of the two angular coordinates (e.g., $\theta$, representing azimuthal angles, in a range, e.g., from 0° to 360°). The y (vertical) dimension is mapped to the other (e.g., $\varphi$, representing inclination angle, in a range, e.g., from 0° to 180°, or −90° to +90°, depending on the 0-angle convention adopted). The z (depth) dimension is optionally directly substituted with r. In some embodiments, this mapping may be understood as analogous to projection of angular coordinates onto a curved surface, for example a cylinder, cone, or other surface—except that local relative distance information is retained so that the resulting projection does not smoothly follow the cylinder, cone, or other surface.

In this flattening method, the sizes of r depend on the chosen origin (e.g., at the stage of conversion to spherical coordinates). The origin is chosen, in some embodiments, so that distances to points on the coronary wall which are about equidistant along the wall to the midpoints of each pair of pulmonary veins are also shown about equidistant to this reference in the flattened image (practically, this tends to locate the origin near the geometrical center of the left atrium). In some embodiments, the origin is dynamically changed, according to a current focus of work (e.g., set by the position of probe 31). For example, the origin optionally shifts to give the least distorted available view of a region which is closest in position to a current position of the catheter probe.

It is noted that if r is directly mapped to z, this is similar to setting $a(\theta,\varphi)=0$ in the framework of the following alternative embodiment of a transform from source reconstruction to flattened reconstruction. There is still a global curvature, however, implicit in the choice of coordinate system. This will be discussed after the following indirect transformation method of converting r to z is explained.

In some embodiments of the flattening (block 104) and/or isolating and producing (blocks 112, 114), the source reconstruction is optionally modeled as $r(\theta,\varphi)$; comprising the sum of two terms, each of which describes distances to the surface from some reference point as a function of spherical angle coordinates, e.g.:

$$r(\theta,\varphi)=a(\theta,\varphi)+b(\theta,\varphi)$$

Here and in the following descriptions, $\theta$ may be considered as the azimuth angle, and $\varphi$ as the polar (inclination) angle.

The first term $a(\theta,\varphi)$ describes the global curvature as any suitable smooth geometrical object (e.g., a sphere, ellipsoid, parametric curve, combination of spherical harmonics, and/or long wavelength frequency domain components of a Fourier transform of the surface transformed back into the spatial domain). The object and/or its degree of smoothness is optionally determined by structure (e.g., the angular size) of details which are to be preserved or suppressed. For example, insofar as the first term follows the curvature of a detail in the source reconstruction, that detail will tend to be suppressed in the flattened reconstruction. The parameters of the smooth geometrical object may be chosen, for example, as those that best fit (e.g., minimize differences in distance, minimizes variance, minimize some weighted combination of the two, or best satisfy according to another criterion) the source reconstruction $r(\theta,\varphi)$.

The first term $a(\theta,\varphi)$ gives the distance of the smooth object's surface from the reference point as a function of spherical angle. The second term $b(\theta,\varphi)$ describes the relief details. The second term may be derived as the mathematical difference (by subtraction) of a representation of the source reconstruction in spherical coordinates and the first term, for example:

$$b(\theta,\varphi)=r(\theta,\varphi)-a(\theta,\varphi)$$

So-defined, the second term $b(\theta,\varphi)$ provides, at each spherical angle defined by the source reconstruction, the extra/reduced distance from the reference point to the surface of the source reconstruction, compared to the distance from the reference point to the surface of the smooth geometrical object provided as a definition of the global curvature.

In some embodiments, producing the flattened reconstruction ("flattening the source reconstruction") comprises a lookup operation that re-plots the second term $b(\theta,\varphi)$ into Cartesian coordinates. For example, $z(x,y)=b(\theta_x,\Phi_y)$; wherein x and y are used as lookup variables transformed by the functions $\Theta_x$ and $\Phi_y$ to the defined ranges of $\theta$ and $\varphi$. The assignment effectively determines where "cuts" will be made to allow unrolling the source representation into the flattened representation.

This operation produces a flattened reconstruction which preserves (albeit typically with some kind of distortion, e.g., stretching, size change, and/or local angle change), the relief features of $b(\theta,\varphi)$, and is planar with respect to the global curvature (e.g., if $r(\theta,\varphi)=a(\theta,\varphi)$, to then $b(\theta,\varphi)=0$, and $z(x,y)=0$).

This particular method introduces some distortion in the flattened reconstruction. For example, the path in the source reconstruction of the equatorial circumference (when $\theta=0$) is much longer than the length of its parallel paths as $$\theta \to \frac{\pi}{2},$$

but the two paths are represented as having equal length in the flattened reconstruction just explained. Some level of distortion and/or discontinuity is generally unavoidable when converting curved 3-D surfaces to flat (in 3-D space) representations, but the nature of the distortions/discontinuities can be controlled, e.g., to preserve relative areas, directions, and/or distances. For example, the relative scale of the x and y axes comprises a parameter that may be set. In some embodiments, the ratio is set so that it most closely approaches 1:1 in the regions of the pulmonary veins.

Optionally, one or more cartographic techniques used to control distortions, e.g., of land masses in flat maps of a globe, are used to control distortions of representation in the (x,y) plane relative to a (optionally spherical) global curvature. With the framework just described, this could be generally implemented by making the lookup functions dependent in any suitable fashion on both x and y (e.g., $\Theta_{x,y}$ and $\Phi_{x,y}$), or by another method producing equivalent results. In some embodiments, distortion is controlled so that targeted portions of the body tissue surface are presented with relative reduced distortion; e.g., portions targeted for treatment.

Other methods and/or results of flattening are possible. For example a bowl-shaped or other non-planar flattened reconstruction can be obtained by choosing a global curvature term $a(\theta,\varphi)$ which is suitably different from a best-fitting smooth shape, and/or by using an offset term when producing the flattened reconstruction, e.g., as $z(x,y)=b(\Theta_x, \Phi_y)+c(x,y)$. Non-planar flattened reconstructions provide a potential advantage for allowing reduction of flattening-related distortions, while still exposing a larger surface to simultaneous viewing. However, insofar as a view of a flattened reconstruction eventually targets viewing by the human eye—with all its inherent limitations on field-of-view perception—taking full advantage of this potential advantage may require special arrangements for movement of the reconstruction in the view, and/or for immersive display.

In another example of flattening: in some embodiments, a longitudinally extended and convoluted organ (e.g., an intestine or blood vessel) is rendered in straightened form. A smooth geometrical object used to define a global curvature in such embodiments is optionally an extrusion of a planar figure (e.g., a circle or ellipse) along a parametric path (e.g., a Bezier curve) that follows a centerline of the convoluted organ. Optionally, the planar figure is itself variable as a function of distance along the parametric path. The coordinate system used may be other than spherical, for example, a type of cylindrical coordinate system, wherein distance along the parametric path is used as a linear axis, and position around the parametric path is expressed as a polar coordinate combination of angle and distance (radius).

Whether these sorts of transformations are suitable optionally depends on the types of navigation and/or navigation controls available. For example, inside-out inversion of an exterior surface may be suitable for a beam-type treatment system where the beam may be directed from substantially any location, so that the user always feels as though the beam is coming from a central point. Optionally, treatment in an organ where navigation is substantially push-pull (e.g., navigation of an endoscope through an intestine) is aided by rendering of a view as a more straightened version of actual 3-D geometry.

In a special case, if the first term $a(\theta,\varphi)$ is defined as for a sphere centered at the spherical coordinates origin, then $a(\theta,\varphi)=k$, where k is the constant radius of the sphere. However, the final flattened reconstruction is insensitive to the choice of k in this condition. For a spherical global curvature centered on the spherical coordinate's origin, every choice of k produces a substantially equivalent result, except that there is a relative offset of the flattened reconstruction by a distance along the z axis controlled by k.

In the first transform method described in this section (where r is directly mapped to z), it was noted that the result is similar to setting $a(\theta,\varphi)=0$, and so, accordingly, k=0. This 0-radius sphere is not an indication of "no global curvature", but rather, is possible because of the particular (spherical) model of global curvature inherent in the choice of coordinate system. The global curvature is defined as spherical, albeit implicitly, and is still being removed (even with k=0, since all values of k lead to flattening in this special case, making it unnecessary to specify one in particular).

In converting a flattened reconstruction to a 2-D image (e.g., 2-D in display coordinates), providing a flattened reconstruction view, depth information can be indicated, for example, by orientation-dependent shading of surfaces, and/or by changing the parallax of viewed features depending on the relative positions of the viewpoint and the flattened reconstruction.

For example, distances in FIG. 1C from a reference point 24 internal to left atrium 2 (e.g., a point half-way between reference point 21 and the apex representing valve 12) are transformed in the flattened reconstruction shown in FIG. 1D to a Cartesian axis of image depth. This axis is indicated by arrow 11E.

It should be noted that the flattened reconstruction of FIG. 1D is displayed as though viewed from an offset angle, which potentially serves to highlight certain features (e.g., allow viewing into apertures). Slight changes to the offset angle potentially serve to emphasize differences in depth (e.g., due to parallax changes). Angular positions in FIG. 1C relative to reference point 24 are transformed in the reconstruction of FIG. 1D into the two remaining Cartesian axes, e.g., Cartesian axes extending along arrows 11D and 11C.

It is emphasized that while the flattened reconstruction, in some embodiments (e.g., FIG. 1D) is reminiscent of certain types of cylindrical map projections, the retaining of transformed depth information allows the result to optionally be viewed from any display angle, with resulting shifts in parallax and/or angles affecting feature presentation (e.g., angles interacting with simulated lighting conditions). A traditional 2-D projection of a 3-D surface does not retain such information (this is discussed further, e.g., in relation to FIGS. 7A-7B, herein).

The flattening (curve-straightening, unrolling) type of transformation presented by examples in FIGS. 1A-1D has potential advantages for use in intracardial navigation of a catheter probe (for example, an ablation probe). First, the transformed reconstruction is suitable to lay out in one view an extended surface area which may be a target of measurement and/or treatment procedures. Second, at the same time, the flattened reconstructions optionally preserve a relatively undistorted appearance of surfaces throughout a large target region, for example, in the region of the roots of the pulmonary veins 10. This is particularly of potential benefit for procedures comprising the formation of one or more lines of ablation to electrically isolate the pulmonary veins from surrounding cardiac tissue. In other embodiments, other targets may be selected, for example, other portions of the 3-D object to be represented may be viewed with minimal distortion.

Another potential advantage is that because the flattened representation remains 3-D in character, it defines a volume into which indications related to catheter probe position can be placed, for example, a probe icon or other indication at the probe's current position, including indications that correctly indicate contact with the flattened representation surface.

While a probe position could be placed in a scene together with a source representation before rendering to a typical camera-view type 2-D image, the probe appearance would itself be subject to, e.g., perspective distortions, which could be quite disturbing, e.g., at the edges of a fisheye view. On the other hand, once a 2-D image of the surface is rendered, some 3-D information is lost (e.g., indicated instead by artificial depth cues such as shading and self-masking), so that it is difficult to accurately reintroduce the probe tip position into the scene e.g., so that probe contact with the flattened surface at different depths is correctly shown. Also, 2-D image will tend to suppress detail where there is more than one layer (e.g., blood vessels branching beyond a lumenal surface of a heart chamber).

Setting of the Cut Line

In some embodiments, remaining parameters of the flattening include where to make the "cut" (e.g., represented by the lines 13A extending from reference points 22 and 23 in FIG. 1A, and/or line 13 in FIG. 1C).

Figure 1G:
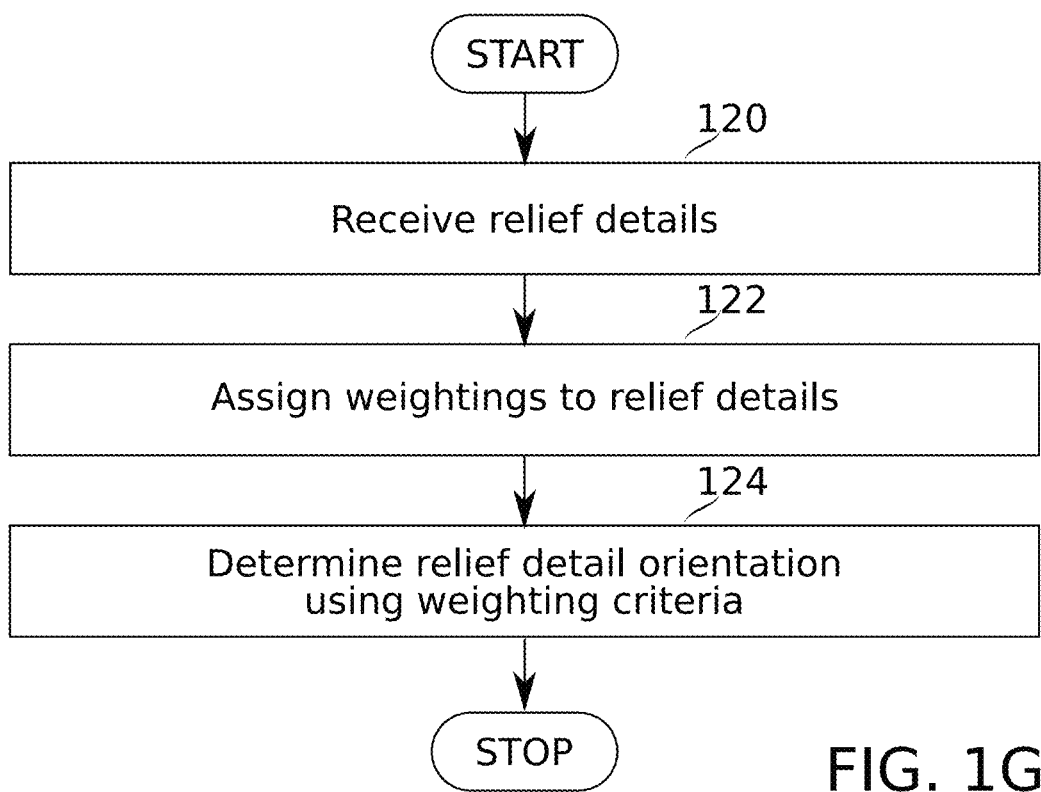
FIG. 1G is a flowchart outlining a method of determining an orientation of a representation of a curved body organ surface, according to some embodiments of the present disclosure.

Reference is now made to FIG. 1G, which is a flowchart outlining a method of determining an orientation of a reconstruction of a curved body tissue surface, according to some embodiments of the present disclosure.

At block 120, in some embodiments, relief details are received. These relief details may be the isolated relief details of block 112. Optionally, relief details are provided together with the global curvature, in which case the operations of block 122 are optionally adjusted to discount effects of global curvature on the weighting of relief details.

At block 122, in some embodiments, weightings are assigned to the relief details. Optionally, the weightings are assigned according to distance and/or depth ("amplitude") of relief details, relative to a reference point, reference offset, and/or reference curvature (e.g., a suitable global curvature definition). Weightings can be directly proportional to relief detail amplitude, linearly related, related as a power function, or provided as some other function of relief detail amplitude.

At block 123, in some embodiments, orientation of the relief details is determined, using criteria applied to the weightings assigned at block 122.

With continued reference to the method of FIG. 1G: it has been noted already that the "cut" applied in the production of FIG. 1D (represented by line 13) is oriented to pass through the center of mitral valve 12. The rotational orientation of the line also affects the flattened reconstruction and/or view thereof; for example, if line 13 was rotated (about a vertical axis) by 90°, then the layout of features in FIG. 1D would also be rotated by 90°, with corresponding shifts in discontinuities and other distortions.

With respect to flattened reconstructions of the left atrium inner surface, the inventors have found that the cut orientation shown results in a flattening which presents surface features in a way that is convenient for navigation of an intracardial catheter probe (at least, for common anatomical variants). The zones of greatest distortion and/or discontinuity near the mitral valve 12 are also zones where catheter navigation is potentially complicated by strong and variable currents of blood flow. Moreover, since the valve is anyway moving all the time, the reconstruction in that region anyway is potentially less accurate and/or interesting for purposes of targeting by the catheter. Moreover, the zones 16A, 16B which have the greatest stretch-distortion are also positioned away from regions where features of particular interest for some treatments, such as the pulmonary veins 10 and the LAA 15, form distinct clusters.

In some embodiments, the orientation of cut 13 can be determined and/or adjusted manually, and/or automatically based on explicit identifications of features and/or selection from a range of options. Optionally, manual controls allow adjustment of the cut position and/or of an origin used as a basis for the flattening operation (e.g., a center of the global curvature), for example to account for individual anatomical differences.

Optionally, operation of the controls is defined over a Cartesian coordinate space defined over the source reconstruction. These controls optionally separately control movement of the origin in the x, y, and z directions (e.g., by 5 mm at a time, or another distance). Optionally, controls for elevation, roll, and azimuth control rotation (e.g., in 5° increments, or in another increment) around the x, y, and z axis, respectively. In some embodiments, changing of a control setting results in an immediate update of one or both of a view of the source reconstruction and the flattened reconstruction. Additionally or alternatively, another control set is defined, for example, controls defined over the Cartesian space of the flattened reconstruction itself. For example, an x axis control has the effect of panning a view of the flattened reconstruction left or right, a y axis control which has the effect of scrolling the view up or down, and/or a z axis control has the effect of translating the view toward or away from a perspective point of the view. A rotational control optionally sets the cardinal directions of the x and y axes with respect to the flattened reconstruction. Controls are additionally or alternatively provided for and/or interpreted as adjustments to suitable parameters in a spherical or other non-Cartesian coordinate system.

In some embodiments, automatic selection of a flattening parameter set comprises a process of scoring a plurality of available flattening parameter sets for properties (with respect to a particular anatomy and/or procedure plan) of angle preservation, distance preservation, and/or contiguity of representation, and choosing and/or making available for choice options which score best. In some embodiments, a flattening parameter set may include indications of how and/or where to introduce discontinuities (e.g., cuts along the edges of the flattened reconstruction and/or view thereof), and/or what angular position should be set at the center of the flattened reconstruction and/or view thereof.

In some embodiments, the orientation is determined automatically and on the fly, based on global characteristics of the reconstruction, and general information about anatomical layout. For example, the cut 13 is positioned, in some embodiments, to where the resulting flattened reconstruction best balances feature depth (treated as a "weight") as a function of distance from the reconstruction's (x,y) center 21. For example, along the left-right direction (arrow 11C of FIG. 1D), there are two clusters of relatively deeper features; so those features are set at roughly equal horizontal distances from the center. In the up-down direction (arrow 11D of FIG. 1D), the weight of each of these clusters falls along a common center, so the features having larger distances are weighted such that they "sink" to the middle. Optionally, the orientation of the axes themselves is set so that one axis passes along this common center. Remaining ambiguity in setting the center point (e.g., whether to cut through the mitral valve, or cut through the atrial wall opposite) is optionally resolved by choosing the alternative with the greatest or least contiguously represented distance between cluster positions.

Optionally, for body surfaces of different organs having different general anatomical arrangements of features of interest and/or for use in different procedures, different rules are set, and the weightings of block 122 used to satisfy those rules. It is noted that the rules described for FIG. 1D have the effect of naturally bringing the image into a left/right and top/bottom balanced distribution of features (which also happens to create a flattened reconstruction view which is effective for displaying left atrium features related to atrial ablation procedures). However there is optionally any suitable offset applied to bring features into suitable relative positions for a particular application (e.g., a valve procedure would optionally center the mitral valve in the view), and/or anatomy (e.g., a reconstruction for use in the right atrium optionally uses the superior and inferior vena cava as landmarks for orientation of a flattened reconstruction view of the right atrium).

Considering the broader case of an arbitrary distribution of anatomical features of interest viewed on a flattened surface, the selection of an optimal flattening may be made differently in different conditions and/or for different purposes; e.g., different chambers and/or organs, and/or different therapy plans. For example:

Ablation inside the left ventricle (LV), e.g., for ventricular tachycardia ablation, is optionally performed against the background of a flattened reconstruction of an LV which has been flattened using chamber-specific parameters.

For a left atrial appendage closure procedure, the LAA ostium is optionally centered in a flattened reconstruction view of the left atrium.

For a transseptal procedure, the fossa ovalis is optionally centered in a flattened reconstruction view of the right atrium.

For an atrial septal defect and/or patent foramen ovale closure, the patent foramen ovale and/or atrial septal defect is optionally centered in a flattened reconstruction view of the right atrium.

For coronary sinus cannulation and/or placement of a pacing electrode, the coronary sinus is optionally centered in a flattened reconstruction view of the right atrium.

For purposes of using a flattened reconstruction for purposes of guiding navigation within a body cavity, it is optionally preferable for target regions to be continuously linked (e.g., navigable between without having to pass over a "cut"), while geometrical distortions of angle and/or size are pushed to regions away from target regions. Optionally, parameters governing flattening of a surface (for example, any of the parameters just described, or other parameters governing a different flattening method) are modified during the procedure, for example, to shift distortions away from current main targets.

Optionally, there is more than one cut. A cut may be considered as a discontinuity-type distortion which, once introduced to a projection, potentially allows greater freedom in reducing distortion somewhere else. This provides a potential advantage where there are areas of little interest that can be more heavily distorted in exchange for improved accuracy of representation elsewhere.

Flattened Reconstruction Views in Comparison to Other View Types

Features of the view of FIG. 1D in particular may be contrasted with other types of views.

Figure 9A:
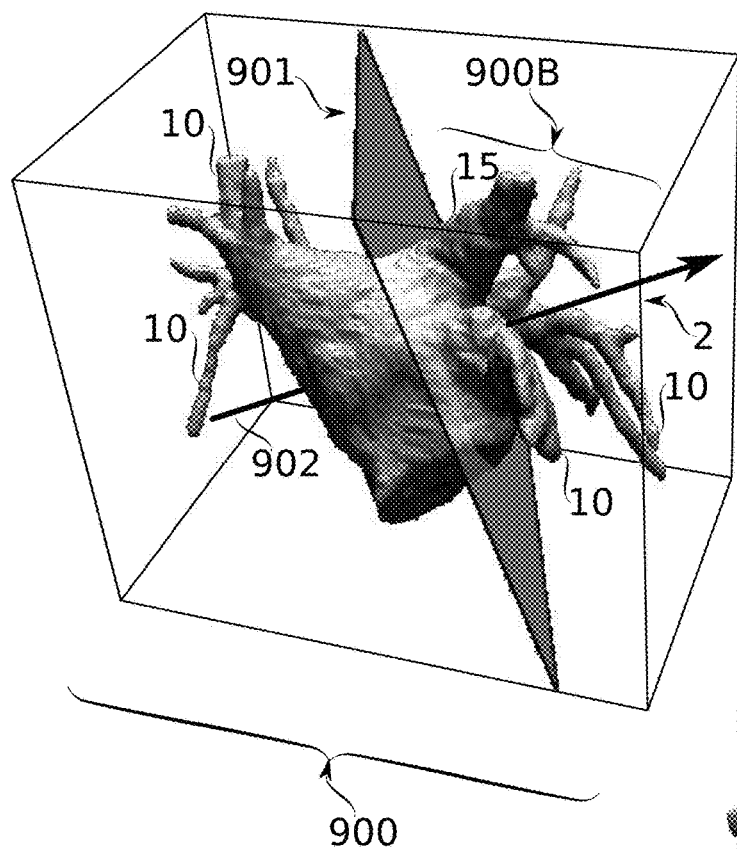
FIG. 9A shows a planar sectioning of a 3-D representation of a body part reconstruction, according to some embodiments of the present disclosure.
Figure 9B:
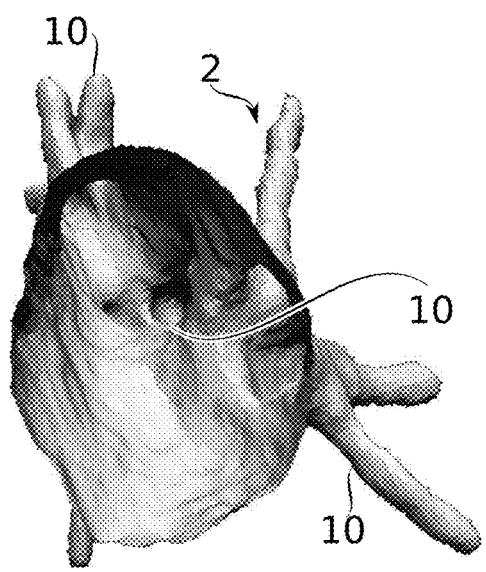
FIGS. 9B-9C show views looking into the two sectioned parts of body part reconstruction, according to some embodiments of the present disclosure.
Figure 9C:
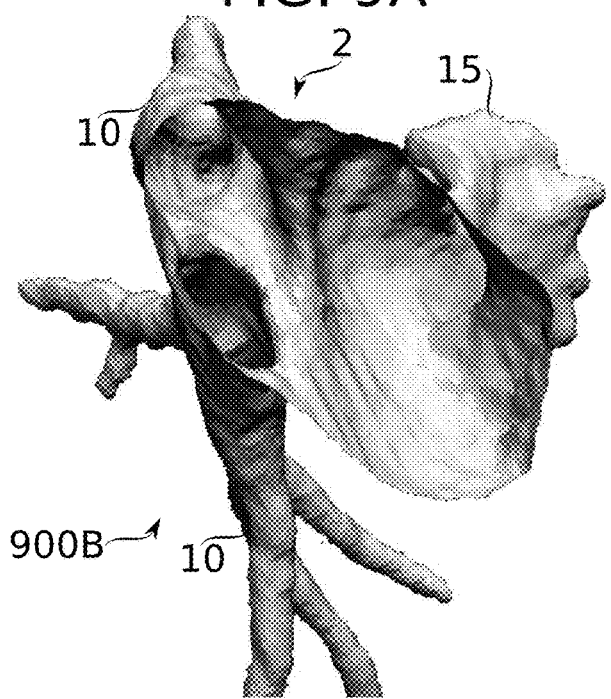

For example, reference is now made to FIG. 9A, which shows a planar sectioning of a 3-D representation of a body part reconstruction 900, according to some embodiments of the present disclosure; and to FIGS. 9B-9C, which show views looking into two sectioned portions of body part reconstruction 900, according to some embodiments of the present disclosure.

FIG. 9C shows a view looking along axis 902 (normal to sectioning plane 901), and towards two of the pulmonary veins 10 and LAA 15 of a left atrium 2. Due to the curvature of the left atrium 2, details along some lumen wall portions (e.g., those oriented substantially along axis 902) are obscured and/or considerably foreshortened. The curvature of the left atrium 2 also makes it difficult to simultaneously get comparable impressions of all the pulmonary veins 10 (even from one side) and LAA 15 in one view: apertures of each present themselves at widely varying angles. This potentially affects the appearance of surface shapes, and/or the lighting conditions affecting how well each feature can be distinguished. As another example of a sectioned view: FIG. 9A shows a view after cutting by a different plane) into another section of body part reconstruction 900 showing different pulmonary veins 10, subject to the same issues of curvature and/or lighting. Moreover, there is apparently no single planar sectioning which produces a sectioned portion that includes all the indicated features of FIGS. 9B and 9C in a single clear view.

Also for example, reference is now made to FIGS. 10A-10D, which show a range of standard camera-type views of the interior of a reconstructed left atrium, according to some embodiments of the present disclosure.

Figure 10A:
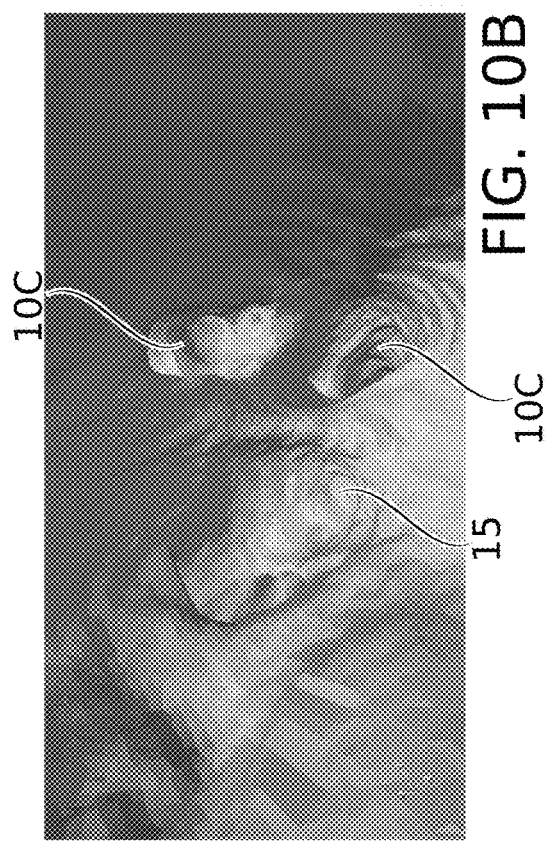
FIGS. 10A-10D show a range of standard camera-type views of the interior of a reconstructed left atrium, according to some embodiments of the present disclosure.
Figure 10B:
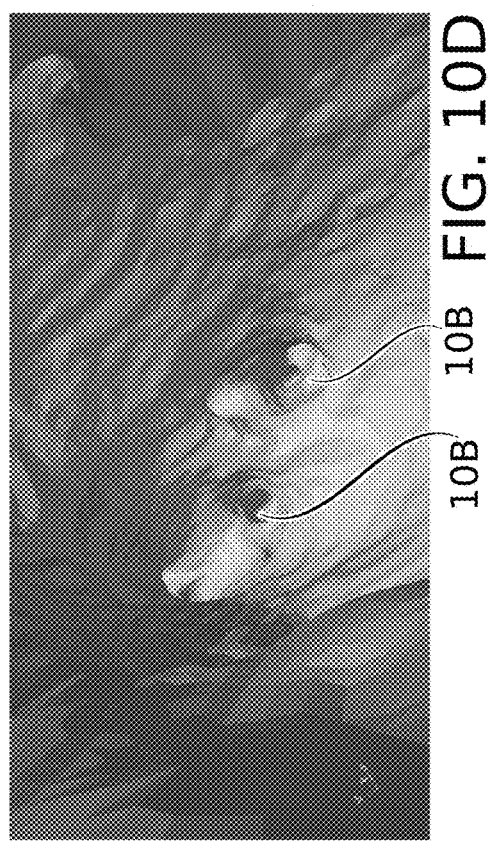

In FIG. 10A, LAA 15 and two left pulmonary veins 10C are shown in a 30° field of view (30° is the angular width of the field-of-view subtended left-to-right) from a perspective internal to the left atrium, and relatively near to the atrial surface. FIG. 10B shows the same features, from the same position, using a 60° field of view. In both cases, angular cropping complicates identifying at a glance exactly what features are shown, and in what the global orientation. This problem is somewhat reduced in the 60° view, however there is an added complication that regions near the edge of the image are compressed in the radial direction, while being relatively spread out in the circumferential direction.

Figure 10C:
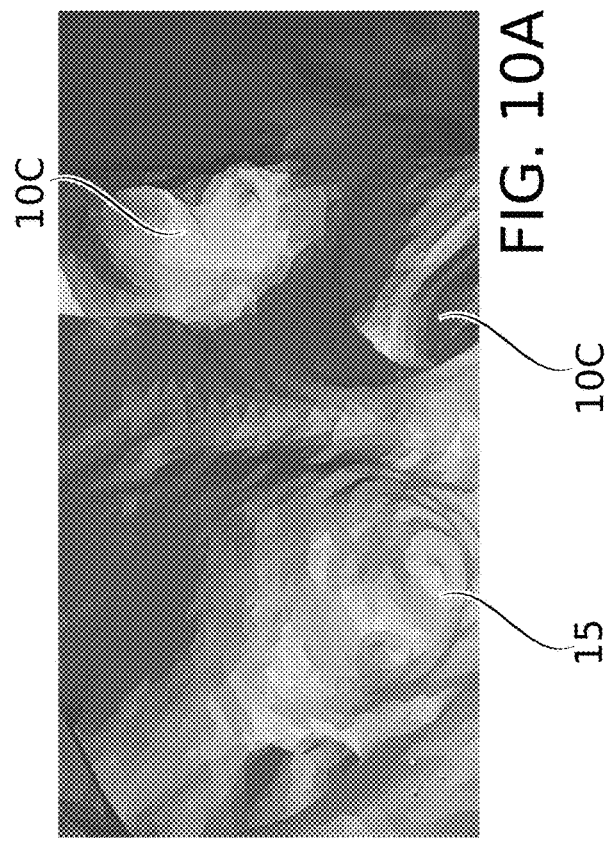
Figure 10D:
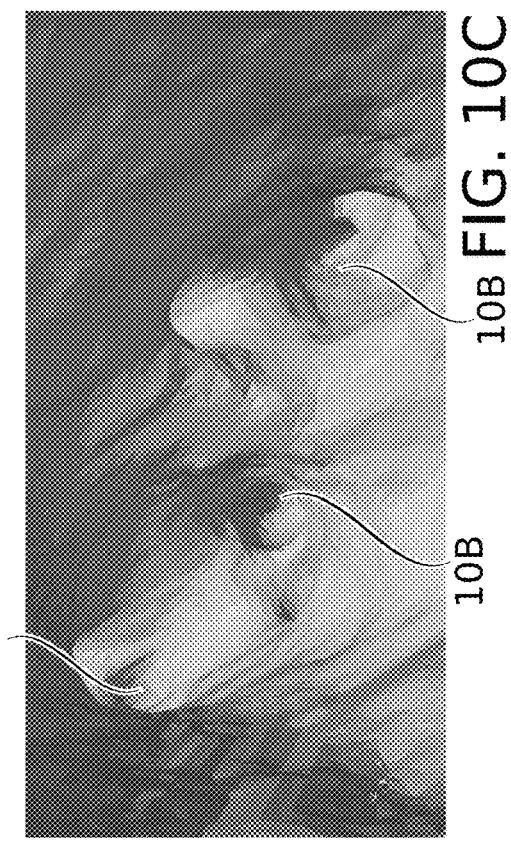

FIG. 10C shows the right pulmonary veins 10B (also in a 30° field of view). The features shown are clearly different from that of FIGS. 10A-10B, but on their own, they are difficult to unambiguously identify. In FIG. 1D, the field of view angle has been broadened to 60°, compared to the 30° field of view of FIG. 1C, but this apparently does not substantially improve the identifiability of the features in the central part of the field of view, while again introducing significant distortions of features near the image edges.

Apart from preservation of depth information in an intermediate flattened reconstruction, it should also be noted that the views of FIG. 1B and/or FIG. 1D are potentially different in character than would potentially be achieved, for example, by using a "fisheye lens" transformation of the source reconstruction, similar to views provided by ultra-wide-angle lenses and/or their simulations. Using computerized image transformation, it is possible to represent on one 2-D screen a 180° view or greater-angled camera view of a surrounding visual field, optionally up to a 360° view. However, this introduces distortions which increase for the edges of the visual field as the field of view angle increases (distortion potentially far beyond what is shown for the 60° views of FIGS. 10B and 10D). Potential disadvantages compared to the flattening just described in relation to FIG. 1B include:

They potentially become highly distorting of shapes and/or angles approaching their edges;

Distortion is potentially not inherently controlled for features of particular interest; and/or Attachment of the view to a viewpoint could cause the distortions change to shape constantly as the central direction of view shifts.

Flattened Representations with Overlays

Figure 2A:
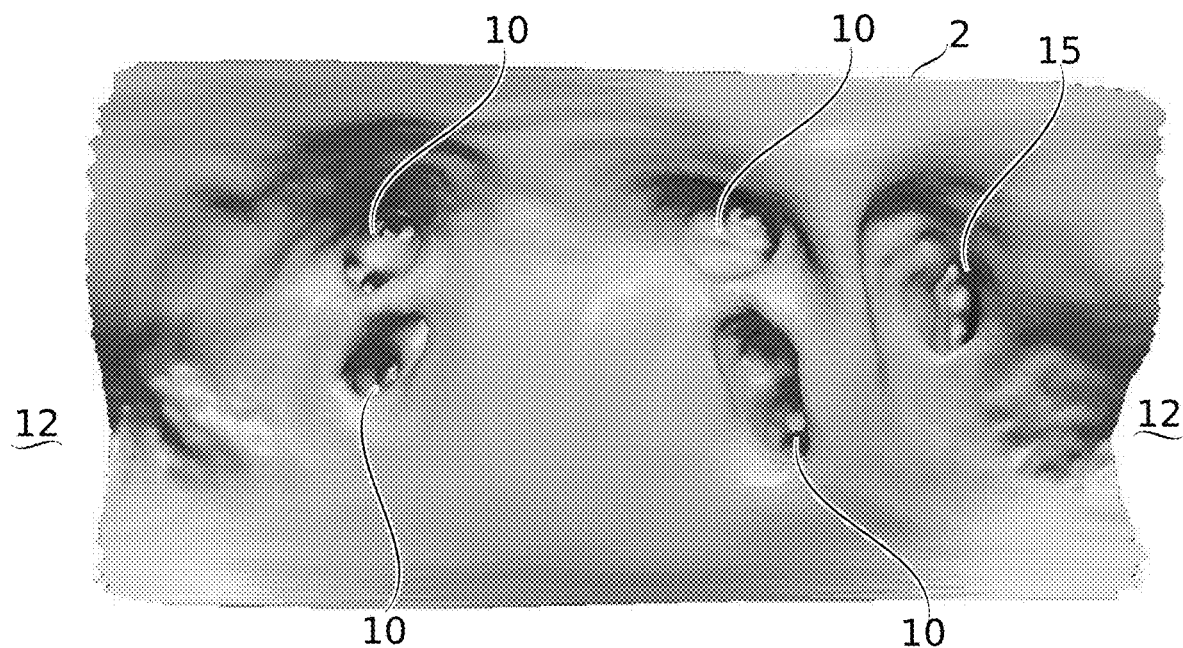
FIG. 2A shows a flattened representation view of left atrium anatomy, according to some embodiments of the present disclosure.

Reference is now made to FIG. 2A, which shows a flattened reconstruction view of left atrium 2 anatomy, according to some embodiments of the present disclosure. Further reference is made to FIG. 2B, which shows the view of FIG. 2A, with additional markers indicating ablation points 14, 14A and catheter probe 31, according to some embodiments of the present disclosure.

Figure 2B:
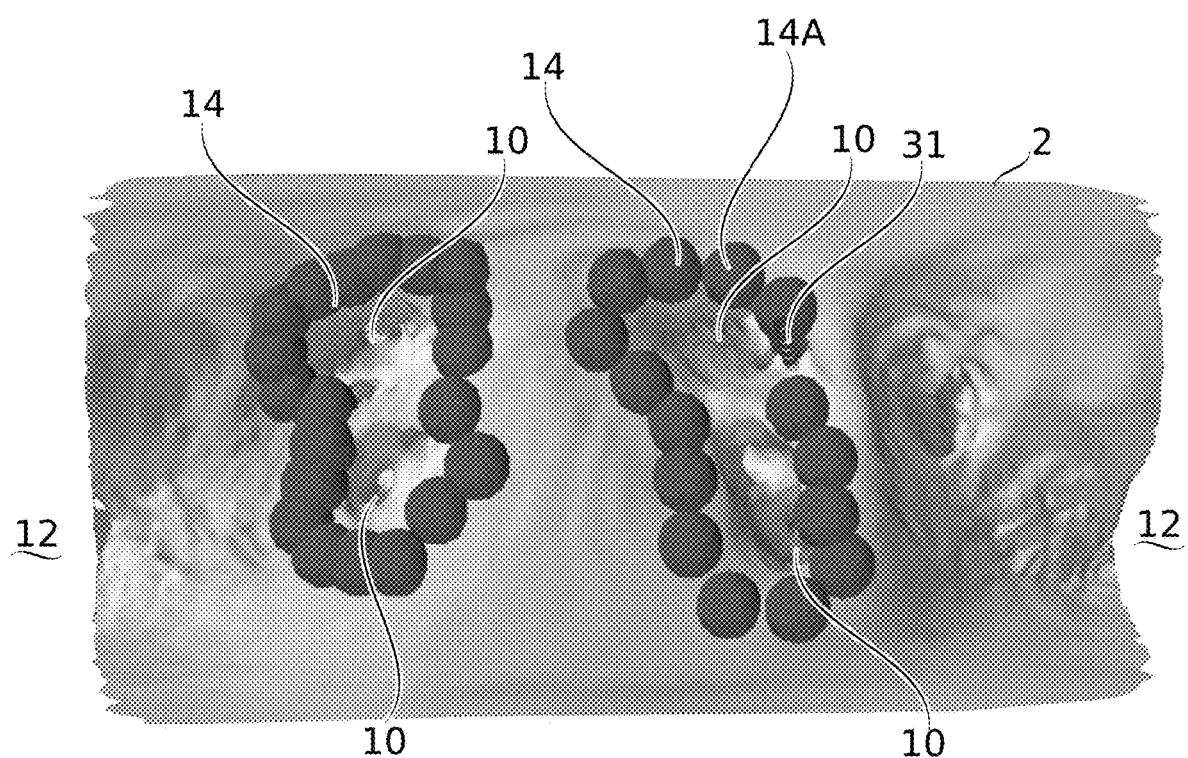
FIG. 2B shows the view of FIG. 2A, with additional markers indicating ablation points and catheter probe, according to some embodiments of the present disclosure.

In FIGS. 2A-2B, the same anatomical features indicated in FIG. 1D and schematically in FIG. 1B are shown again based on a 3-D left atrium model, illustrating the "relief"-type display of features which the flattened reconstruction supports.

Also shown in FIG. 2B is a representation of a catheter probe 31. Ablation line 14 is represented by balls 14A embedded in the tissue around the pulmonary veins 10; each ball 14A optionally represents a sub-lesion of the ablation line. The similarity in size of each ball 14A is an indication of the relatively low relative distortion in the regions where they appear (each ball is rendered to be the same size in 3-D).

Figure 7A:
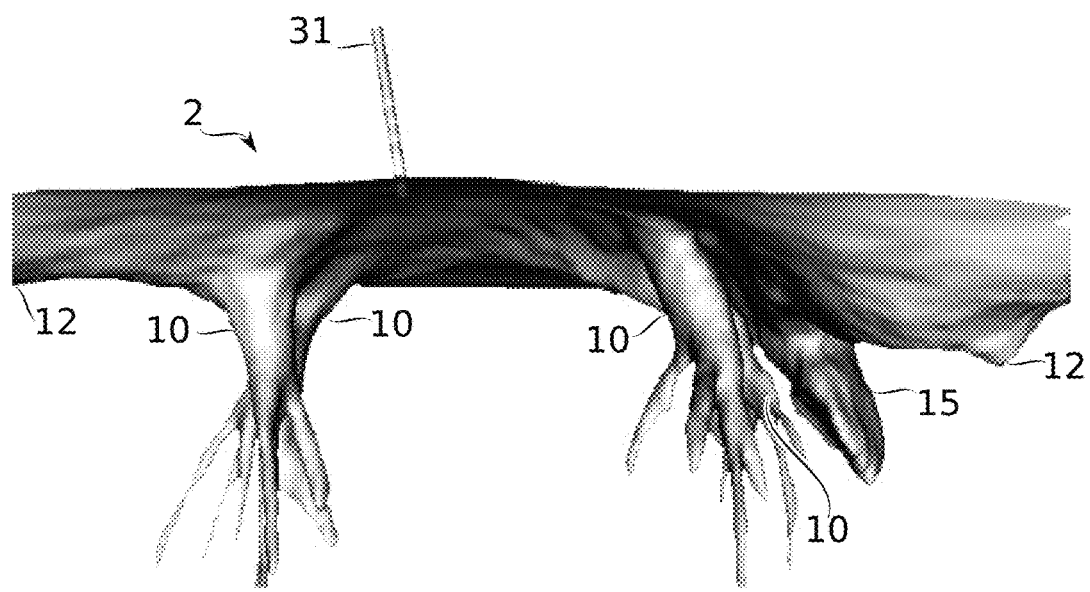
FIGS. 7A-7B show the same flattened representation shown in FIGS. 1D and 6B, viewed at different tilt angles, according to some embodiments of the present disclosure.
Figure 7B:
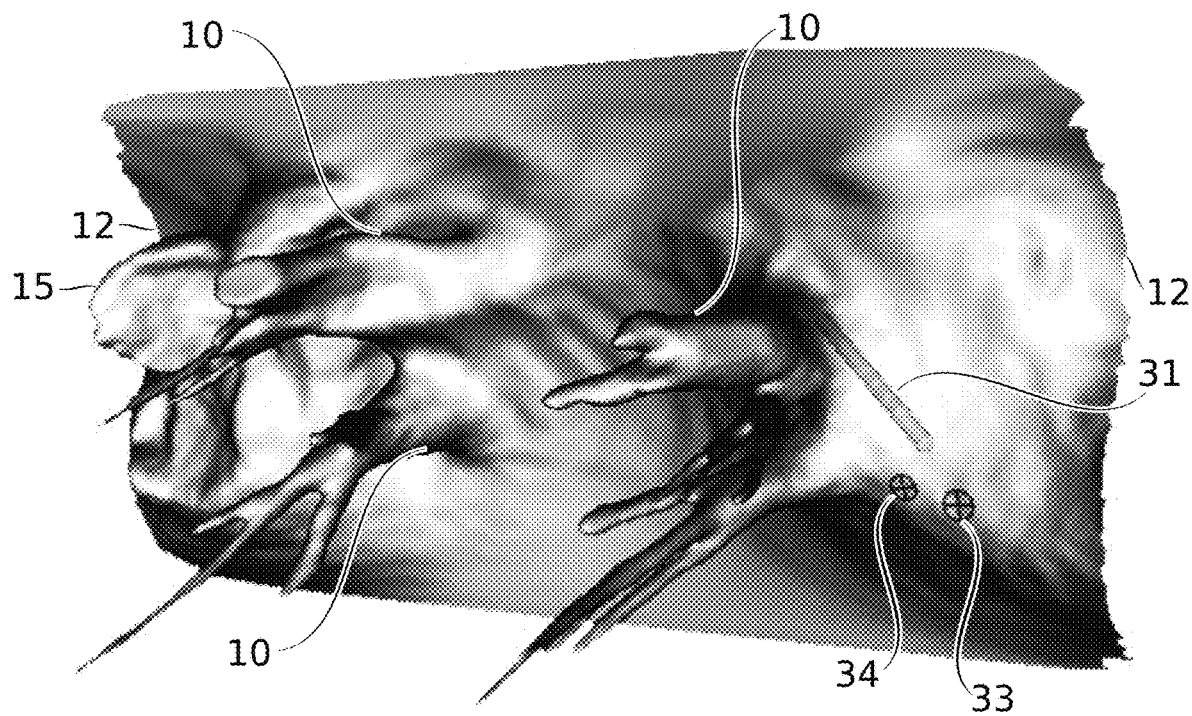

It should be noted again that although the images of FIGS. 2A-2B are flattened compared to the actual geometry of a left atrium, some features (particularly PVs) appear in 3-D relief. Optionally, the simulated illumination is dynamic in the flattened reconstruction view, e.g., by continuous linkage to the flattened reconstruction, which serves as a model of the 3-D scene illustrated in the view. In some embodiments, illumination effects are tied to motion of a catheter probe shown within the view, which can help provide a user with a sense of position of the probe in depth relative to displayed surface features. Optionally, the flattened reconstruction view itself can be re-oriented (tilted), for example as shown in FIGS. 7A-7B.

Figure 3:
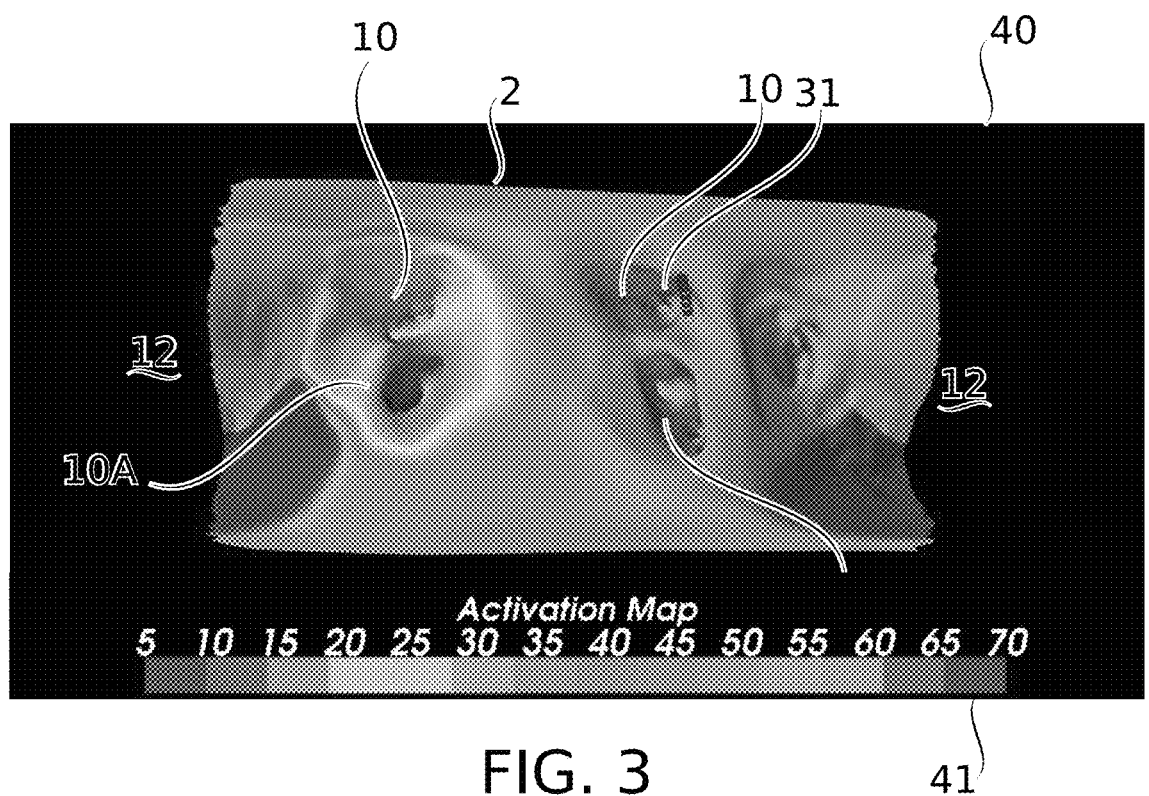
FIG. 3 schematically represents a flattened representation of left atrium anatomy including a superimposed activation map, according to some embodiments of the present disclosure.

Reference is now made to FIG. 3, which schematically represents a flattened image 40 of left atrium 2 anatomy including a superimposed activation map, according to some embodiments of the present disclosure.

In some embodiments, a flattened reconstruction view of a tissue surface allows a user a simultaneous overview of features extending over a broad angular area. In FIG. 3, there is shown mapped to the LA anatomy an activation map, wherein color indicates relative time after an impulse begins that it reaches each particular region of the heart wall. The map clearly identifies at a glance (e.g., with reference to time scale 41 in milliseconds) that activity around pulmonary vein 10A is early enough to be a potential triggering source for impulses (and, accordingly, is potentially a preferred target for isolation by ablation). Moreover, since all PVs are shown simultaneously, it is relatively easy for an operator to assess differences between and/or track changes in map characteristics (e.g., as effects of ablation begin to appear in the map) at a range of widely separate target regions.

In some embodiments, use of superimposed (overlay) indications is used to indicate another parameter, for example, directions of blood flow, which potentially indicates differences between blood vessels, valves, and other apertures in a heart chamber. For example in a left atrium, inward flow is from the pulmonary veins, outward flow from the mitral valve, and flow is variable, low, and/or non-existent for the left atrial appendage. Use of an overlay to indicate wall thickness is also described, for example, in relation to FIG. 11D. In some embodiments, a plurality of different overlay indications are available, (e.g., any of those described herein), and they can be turned on or off in any suitable combination.

Figure 8A:
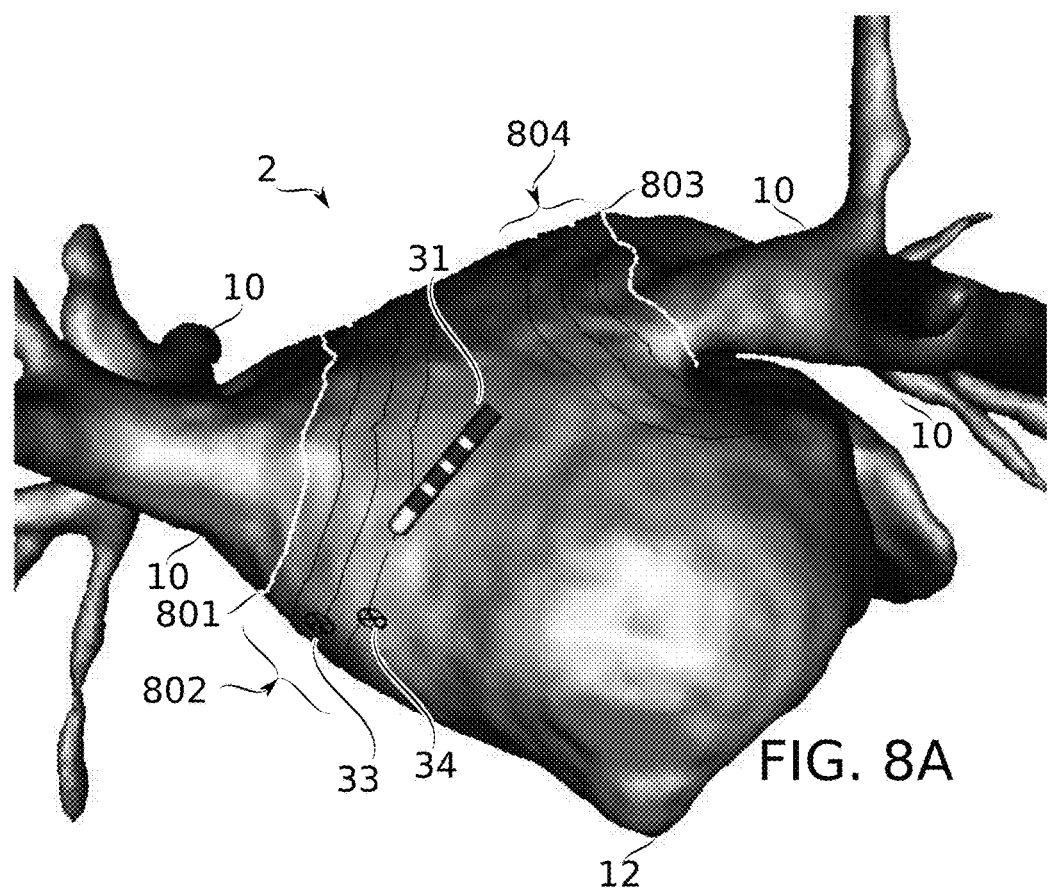
FIGS. 8A-8B illustrate a non-flattened and flattened representations of a left atrium having a contour overlay, according to some embodiments of the present disclosure.
Figure 8B:
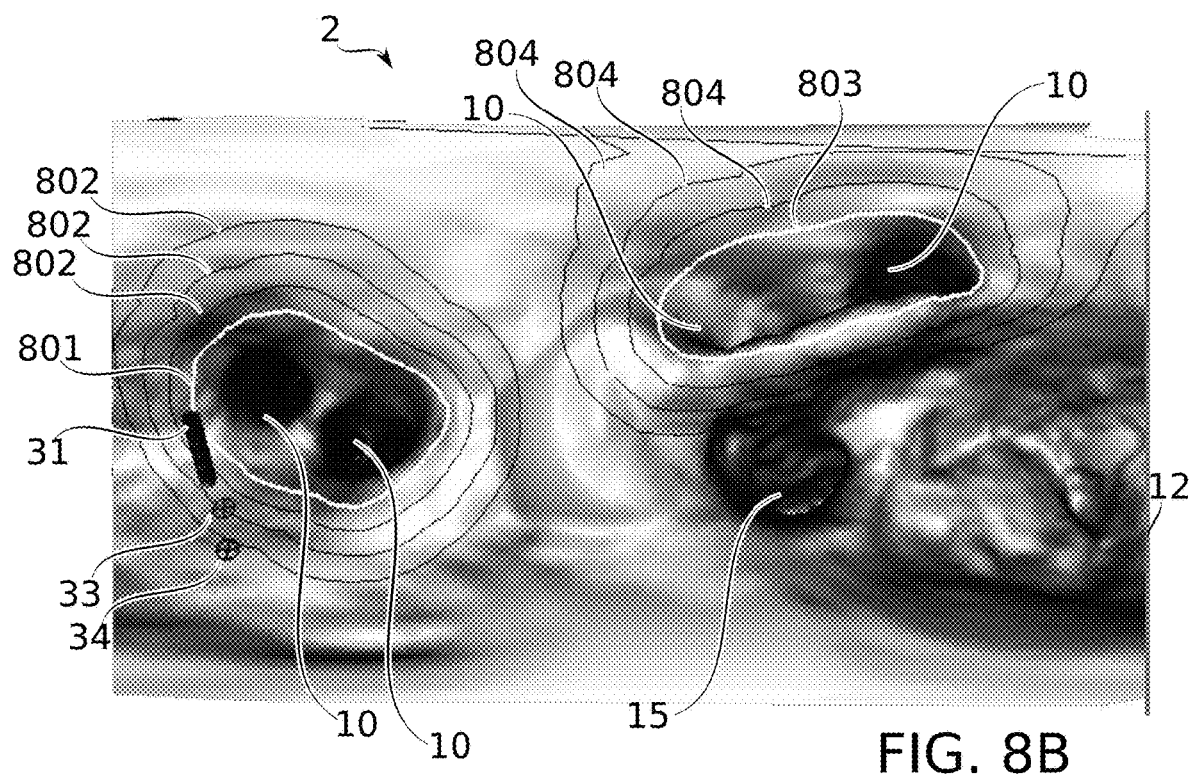

Reference is now made to FIGS. 8A-8B, which illustrate a source (un-flattened) reconstruction and a flattened reconstruction of a left atrium 2 having a contour overlay, according to some embodiments of the present disclosure. Some features previously discussed are also indicated here, for example, pulmonary veins 10, probe 31, proximity markers 33, 34, mitral valve 12, and left atrial appendage 15.

The two different pairs of PVs 10 are each marked with surrounding inner contours 801, 803, and a series of outer contours 802, 804. The contours are optionally spaced from each other at a constant distance along the surface (for example, as shown). This potentially helps in emphasizing 3-D structure, e.g., since contour lines will appear to be closer together where the surface angles away from perpendicular to the viewing angle. Distortions of contours 804 near the top of the image (splaying to horizontally wider intervals) also help to indicate the "stretching" effect of distortions introduced during the flattening transformation.

Flattened Representations with Probe Position Indications

Figure 4:
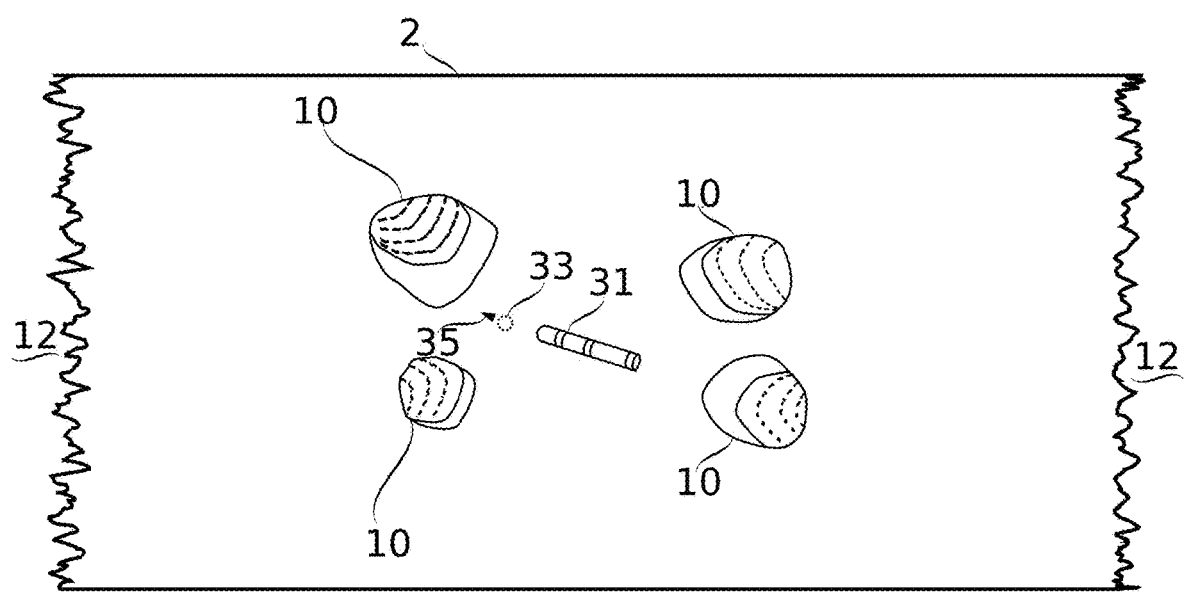
FIG. 4 schematically represents a navigational situation of a catheter probe represented as moving with respect to a flattened representation view of a left atrium, according to some embodiments of the present disclosure.
Figure 5A:
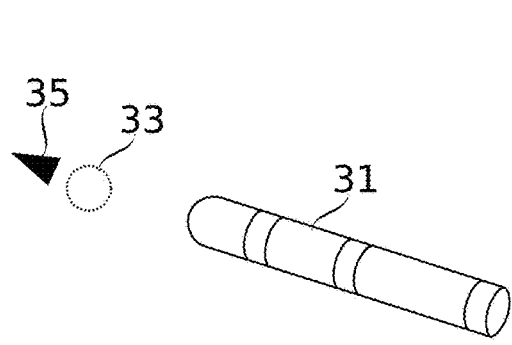
FIGS. 5A-5B schematically represent indications of navigational target, distance from a surface and/or direction of a catheter probe moving with respect to a flattened reconstruction view, according to some embodiments of the present disclosure.
Figure 5B:
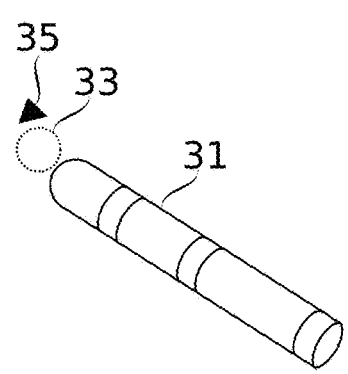

Reference is now made to FIG. 4, which schematically represents a navigational situation of a catheter probe 31 represented as moving with respect to a flattened reconstruction view of a left atrium 2, according to some embodiments of the present disclosure. Reference is also made to FIGS. 5A-5B, which schematically represent indications of navigational target, distance from a surface and/or direction of a catheter probe moving with respect to a flattened reconstruction view, according to some embodiments of the present disclosure.

A full-surface view of a flattened reconstruction in particular, whether variable or static, provides a potential advantage for reducing the mental load on an operator working to move, monitor and/or otherwise operate (e.g., for treatment administration) a probe within an environment modeled by the flattened reconstruction.

In some embodiments, cues are provided which potentially help a user better understand the full 3-D position of a probe as it is shown moving with reference to a flattened reconstruction view of a target tissue. In some embodiments, the cues comprise a mark 33 which is projected onto a flattened reconstruction view of a surface of left atrium 2, depending on the current position of probe 31. Optionally, mark 33 highlights a position of a longitudinal axis extending through probe 31, at the region where it intersects the atrial wall. As the probe gets closer to the atrial wall (e.g., as in the movement between FIGS. 5A and 5B), the flattened reconstruction view shows mark 33 and probe 31 approaching each other more closely. This method potentially gives visual distinctiveness to different positions in depth when the catheter probe 31 is angled significantly away from an axis extending orthogonal to the wall. Optionally, in some embodiments, the mark is also shade- or color-coded to indicate distance (e.g., becoming more intense as the probe approaches the wall).

Optionally, the indicative change is a change in shape.

Another type of mark, in some embodiments, is illustrated by mark 35, which is optionally oriented to indicate a direction of movement and/or a direction of orientation of probe 31. Mark 35 is shown moving to different sides of mark 33 between FIGS. 5A and 5B; it should be noted that it does not necessarily track the orientation of the probe itself.

Moreover, mark 35 is shown shorter in FIG. 5B than in FIG. 5A. The difference in length optionally tracks distance from the surface of the atrium 2, as an example of a shape change used to indicate probe position in depth.

In some embodiments, lighting effects are used to help convey an impression of depth position to a user. For example, one or more simulated lights are positioned to cast shadows from probe 31 onto the surface of atrium 2. Optionally, this lighting is simulated in the flattened space defined by the transformed 3-D surface, as if it was a new space defined in Cartesian coordinates. Optionally or alternatively, the shading is rendered using the spatial configuration of the original 3-D space, and shadows are rendered and transformed like other features of the atrium surface 2.

In some embodiments, there is only one light source, optionally simulated as though emitting from the vantage point. Optionally, the shading of different portions of the surface is determined by the angle between the respective portion, and a line connecting the vantage point to the center of the respective portion, for example as in Gouraud shading.

As a probe 31 is withdrawn further and further from the surface (toward an origin defined in the transformation, for example), it optionally is shown distorted as though being transformed directly from the original 3-D space (i.e., using the same transform as is used to create the flattened reconstruction from the source reconstruction). Probe 31 may appear to enlarge greatly, and/or begin to move more quickly across the image for the same size movement, as if being held close to a "camera". In some embodiments, one or more of these transformation effects is suppressed in some fashion. For example, a probe is optionally always shown at the same size, about the same size, or at least not enlarged proportionally with its occupation of angular space with respect to a camera-like point of view. Potentially, this reduces a sense of disorientation that a dramatically magnifying probe might otherwise cause. For example, the probe is optionally plotted always at the same size, hovering over the flattened reconstruction view surface position which is nearest to it, and optionally with an angle appropriate to indicate its angle in the coordinates of the source reconstruction, in view of the selected rendering position in the flattened reconstruction. In some embodiments, rendering of the probe is simply suppressed for some circumstances (e.g., at positions very near to the coordinate origin), and allowed to re-enter the view at a well-defined position. In some embodiments, it is the view itself that changes; e.g., the coordinate origin is moved to keep it well away from the position of the probe, or the view changes to a view of the source reconstruction from a flattened reconstruction view.

In some embodiments, the position of the probe tip is transformed from the source reconstruction to the flattened reconstruction by the same transformation used for transforming the entire volume of the body portion, but the probe emerging from this position is always displayed straight, and optionally of a fixed shape and/or size. The orientation of the straight probe display may be determined, in some embodiments, by the coordinates in the flattened view of two points, e.g., one at the tip of the probe, and another near the tip of the probe.

A transformation origin and/or other projection parameters may also be adjusted, in some embodiments, even when the probe is moving near the tissue surface. For example, the origin is optionally moved closer to tissue regions near the probe, potentially magnifying their appearance (e.g., allowing more detailed tracking) as they begin to subtend a larger angular size. Alternatively, the origin is optionally moved to a position where it shows the current working region in the least distorted fashion available, which may be a more distant point of view. Either adjustment may produce a kind of lens effect (e.g., like a moving magnifying glass), allowing the whole flattened reconstruction to remain being seen at once (e.g., to maintain a sense of orientation and/or context), while also providing the ability to selectively enhance the view in particular areas. Optionally, any parameter of flattening and/or display is adjusted for a similar purpose, or another purpose assisting procedure operations. For example, a flattened reconstruction view is optionally tilted under manual user control and/or automatically in response to probe navigation events such as approaching apertures and/or contact with tissue.

In some embodiments, there is not just one point of view (as defined, e.g., by a coordinate frame of reference and/or global curvature) defined even for a particular flattened reconstruction view; but rather the point of view is defined differently for the transformation of different positions in space. The selected point of view is optionally varied, for example, as a function of just $\theta$ and $\varphi$, as a function of r, as a function of all three variables, or in any other suitable fashion. The point of view definition is optionally varied continuously, which can help to alleviate jarring transitions, with the selection made for transforming each region targeted to considerations particular to the region; for example, one or more of the considerations described herein. For example, as a function of r from some origin point, the point of view is optionally retreated in depth. This optionally reduces the problem of probe "looming", for example.

Figure 6A:
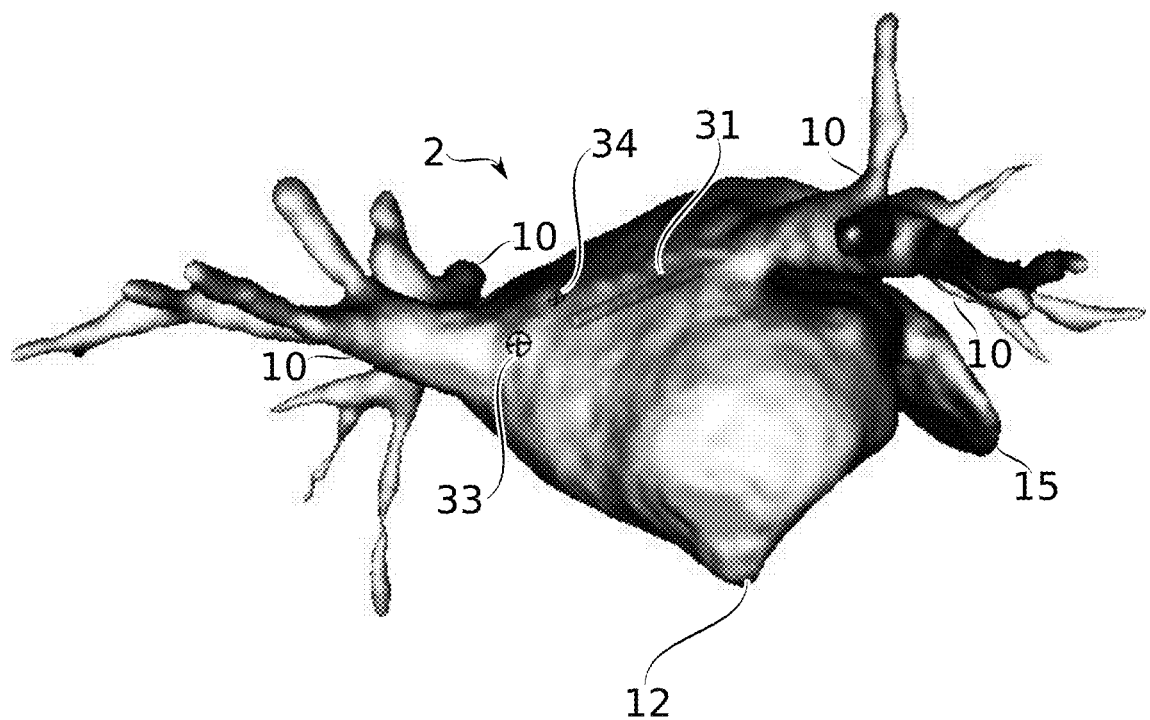
FIGS. 6A-6B show the views of FIGS. 1C-1D, respectively, together within indications of the position of a catheter probe.
Figure 6B:
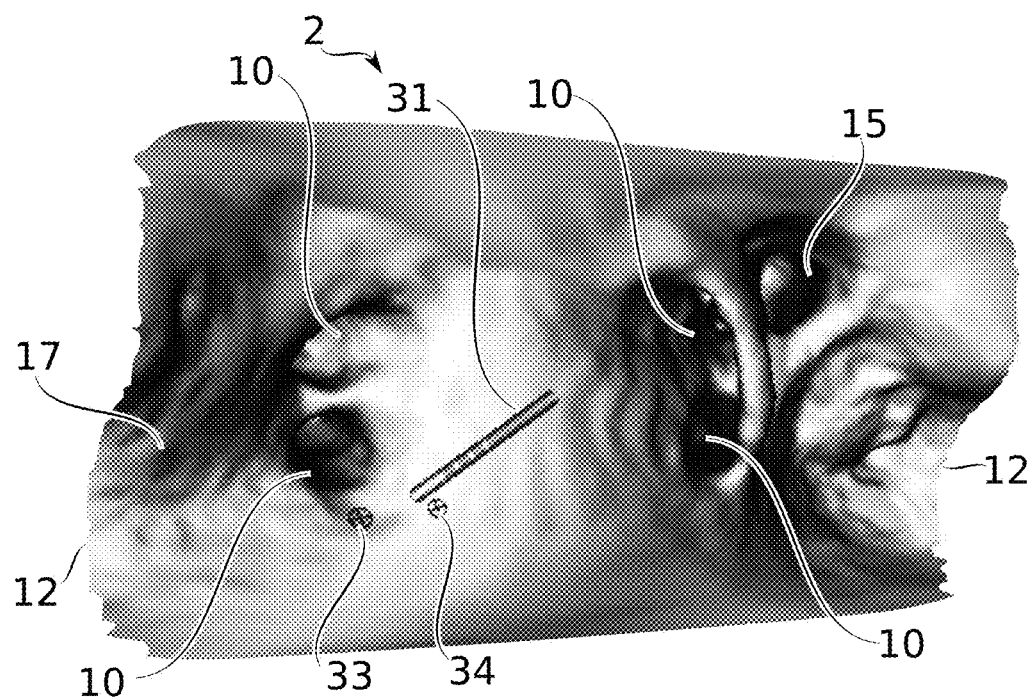

Reference is now made to FIGS. 6A-6B, which show the views of FIGS. 1C-1D, respectively, together with indications of the position of a catheter probe 31. In both figures, probe 31 is indicated at a fixed size. The position of probe 31 is determined, e.g., from a probe tracking method such as electrical field and/or magnetic field based tracking.

Also shown in each of FIGS. 6A-6B are surface proximity markers 33 and 34. Proximity marker 33 is positioned to be centered on a point where a central longitudinal axis of probe 31 intersects the source or flattened reconstruction surfaces. This mark is potentially useful in indicating where a catheter probe will make contact if advanced from its current position without additional steering control. Proximity marker 34 is positioned to be centered on a point of the source or flattened reconstruction surfaces closest to a distal tip of probe 31. If the flattened reconstruction view is oriented perpendicular to a line connecting it to the view's vantage point, this will generally put proximity marker 34 directly "under" the distal tip of probe 31, while at offset view angles, the distance between probe tip and proximity marker 34 becomes an indication of probe-surface distance. Proximity marker 34 is potentially useful, for example, for indicating a potential for oblique surface contact and/or interference with movements of probe 31. When the probe moves towards the wall, the two markers 33 and 34 tend to approach each other, and when the probe is close to touching the wall, the markers may overlap each other.

Flattened Representations at Different Orientations

Reference is now made to FIGS. 7A-7B, which show the same flattened reconstruction shown in FIGS. 1D and 6B, viewed at different tilt angles, according to some embodiments of the present disclosure. Probe 31 and proximity markers 33, 34 are also shown in their visible positions.

In the angles shown, features of the flattened reconstruction can be viewed from the side and back. For example, more blood vessel branches from pulmonary veins 10 are visible than from a substantially front-side (that is, interior-side) view. The surfaces of these vessels ramify as branches exterior to (behind) more interior regions of the flattened representation. This illustrates in particular that in distinction, for example, to a wide-angle projection image, there can be, for any particular (x,y) coordinate pair, a plurality of surface z positions. It should be noted in particular that positions of surfaces defining blood vessels and their branches are mapped, in some embodiments, using position measurements obtained by movement of a catheter probe within a body lumen. This potentially reduces or removes a need for the use of contrast media in depicting blood vessel morphology.

It is also noted that the reconstruction is shown as everywhere closed; for example, blood vessels are shown "sealed off" at the limit of their representation in the flattened reconstruction. This is a feature inherited from the source reconstruction. There is no particular requirement to avoid holes in producing the flattened reconstruction; e.g., holes in the source reconstruction may be considered to represent surfaces "at infinity", or simply treated as missing data during the transformation.

Flattened Representations of the Right Atrium

Reference is now made to FIGS. 11A-11D, which show different flattened reconstruction views of a right atrium 3, according to some embodiments of the present disclosure.

Figure 11A:
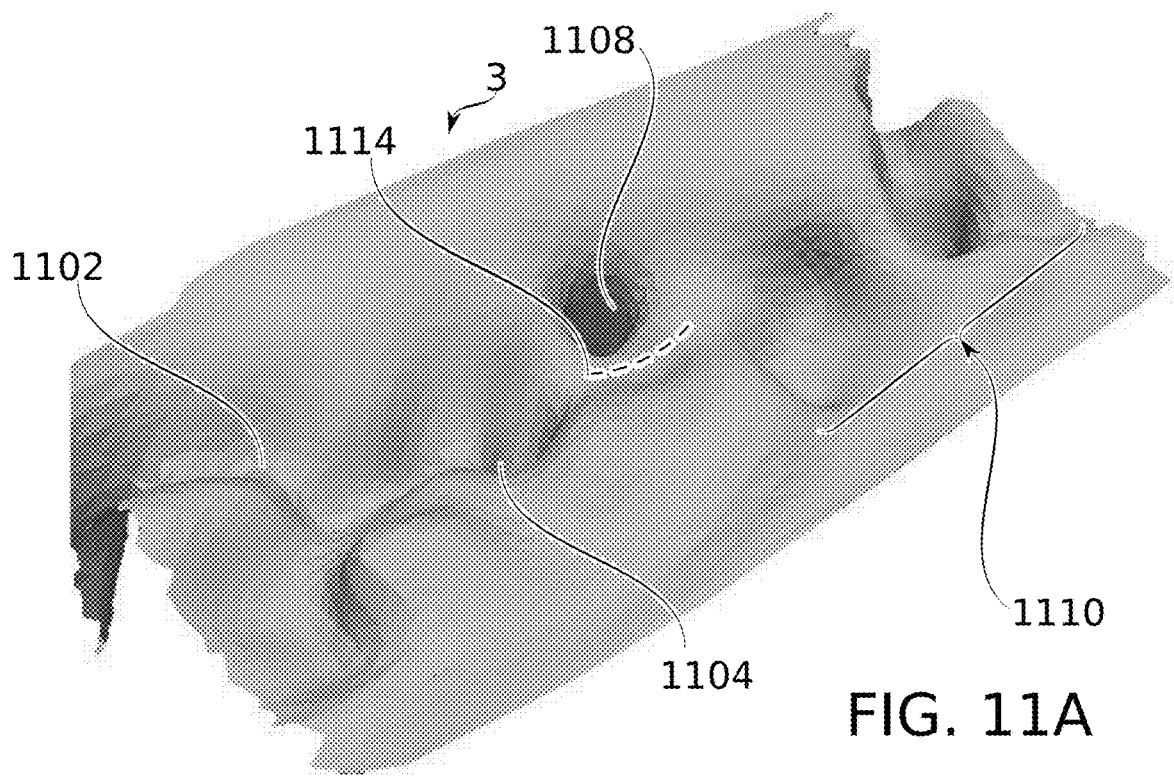
FIGS. 11A-11D show different flattened representations of right atria, according to some embodiments of the present disclosure.
Figure 11B:
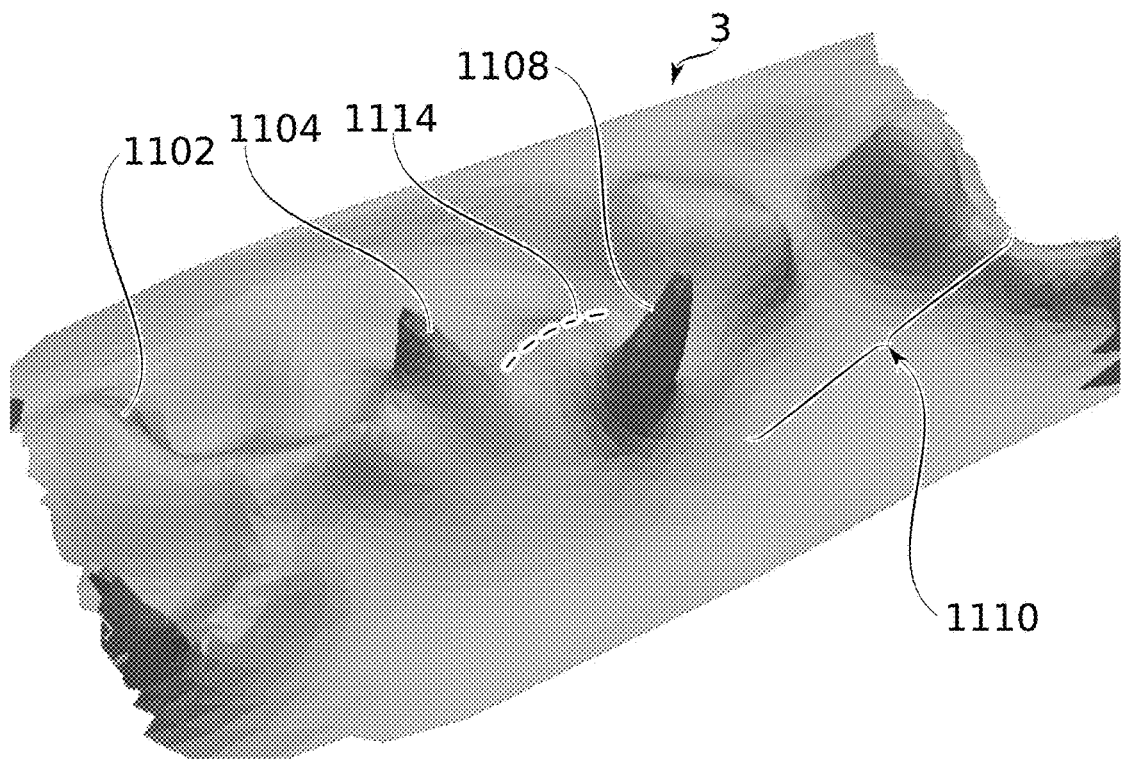
Figure 11C:
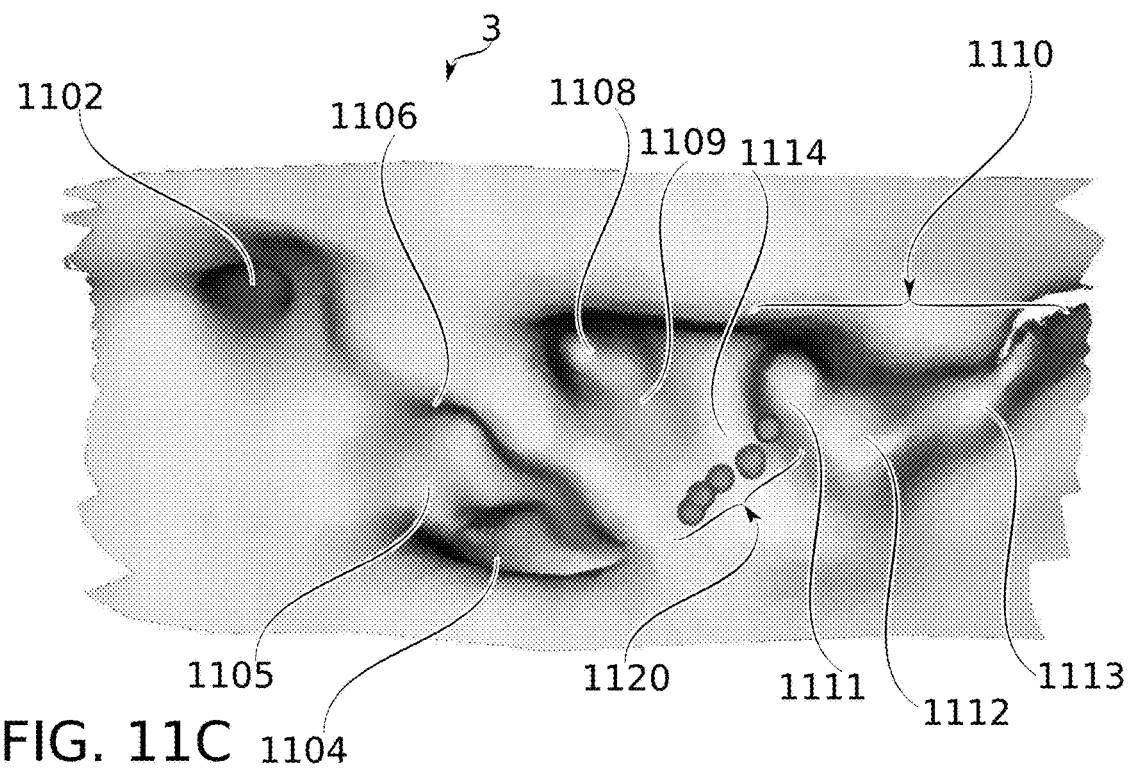

Particular features of a right atrium 3 shown in one or more of FIGS. 11A-11D include apertures leading to superior vena cava 1102, inferior vena cava 1104, and coronary sinus 1108 (CS). Also shown in one or more of FIGS. 11A-11D is tricuspid valve 1110. In FIG. 11C, more details of tricuspid valve 1110 are particularly indicated, including septal, posterior, and anterior leaflets 1111, 1112, and 1113, respectively. FIG. 1C also indicates positions of the fossa ovalis 1106, Eustachian valve 1105, and Thebesian valve 1109.

With particular reference to FIGS. 11A-11B, there are shown front (interior-side, endocardial view FIG. 11A) and back (exterior-side, epicardial view FIG. 11B) views of a flattened reconstruction of a lumenal surface of right atrium 3. It should be understood that there is no particular limitation to these exact orientation. For example, a plurality of images from the flattened 3-D model may be produced from any suitable viewing angle, wherein a first image is a view of the flattened 3-D model from a first direction, a second image is a view of the flattened 3-D model from a second direction, and the first and second images show different sides of a same surface portion.

Particularly noted is the position of the cavotricuspid isthmus 1114 (CTI; located along the indicated dotted line). The CTI 1114 is of interest as a target for certain ablation procedures in the right atrium, for example for the treatment of atrial flutter. In some patients having a condition of atrial flutter, the condition is contributed to by slow conduction along some directions through the CTI 1114. By showing the CTI 1114 laid out in clear relation to nearby features, there is a potential advantage of a flattened reconstruction view for assisting a physician in locating and characterizing this feature for purposes of planning ablation, ablating, and/or verifying ablation along the CTI 1114.

FIG. 11C shows an example of ablations 120 applied over the CTI 1114. It is noted that the particular flattened reconstruction layout of the inner lumenal surface of right atrium 3 places the tricuspid valve 1110 at one border (the right), the superior vena cava 1102 at an opposite border (the left), and generally vertically centering the aggregate of right atrium 3 apertures which extend in between. This arrangement potentially serves to place discontinuities in the display at positions where they make little difference to decisions and operations involved in navigating and/or treating the right atrium.

With respect to coronary sinus 1108: interventional cardiologists and electrophysiology specialists are often challenged by a high degree of variability in the coronary venous anatomy during coronary sinus cannulation, left ventricular epicardial lead placement for cardiac resynchronization therapy (CRT), and/or intra-CS device deployment for mitral valve repair. A precise and fully-automatic segmentation solution for detecting the coronary sinus would provide a potential advantage for such procedures.

Using field gradient-based remote imaging using an intracardial electrode probe system the CS is among the features which may be rapidly distinguished within a right atrium 3. The CS "bud" on the 3-D reconstruction (source reconstruction) and its corresponding 'dimple' on the (interior view) flattened reconstruction view may both be displayed within merely a few seconds after introducing a standard electrophysiology catheter into the right atrium—even before physically touching the endocardial surface. Field gradient-based remote imaging also potentially enables easily identifying and displaying of Thebesian valve 1109, guarding the opening of the CS 1108, that often obstructs cannulation of the CS 1108. The Thebesian valve 1109 anatomy is variable and rarely depicted in full by CT.

Once identified, the full course and anatomy of the CS 1108 can be determined by once or more inserting and pulling back the electrophysiology catheter. This is a straightforward maneuver, requires no contrast media or fluoroscopy, can potentially produce a highly accurate result.

Figure 11D:
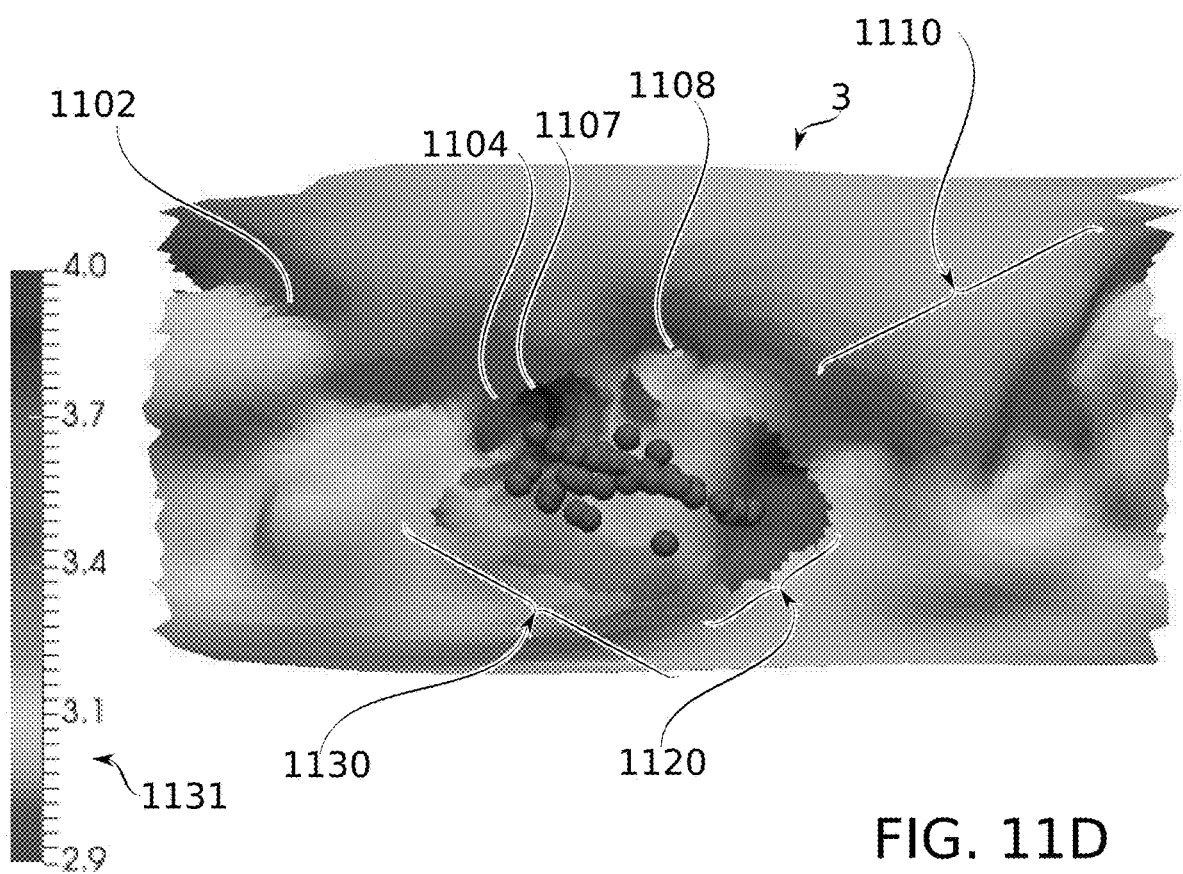

FIG. 11D shows an (optionally color) overlay 1130 which indicates tissue thickness over a portion of the surface of right atrium 3. In particular, a region of maximal thickness 1107 is shown near the inferior vena cava 1104 (bar 1131 indicates how thicknesses map to shading of overlay 1130). In carrying out treatment ablations (the optional positions of which are indicated by spheres 1120), it is a potential advantage to know where tissue is thicker and thinner, for example to allow adjustment of ablation parameters to ensure transmural ablation, and/or to avoid regions which are potentially too thick to effectively ablate or too thin to safely ablate.

Figure 12:
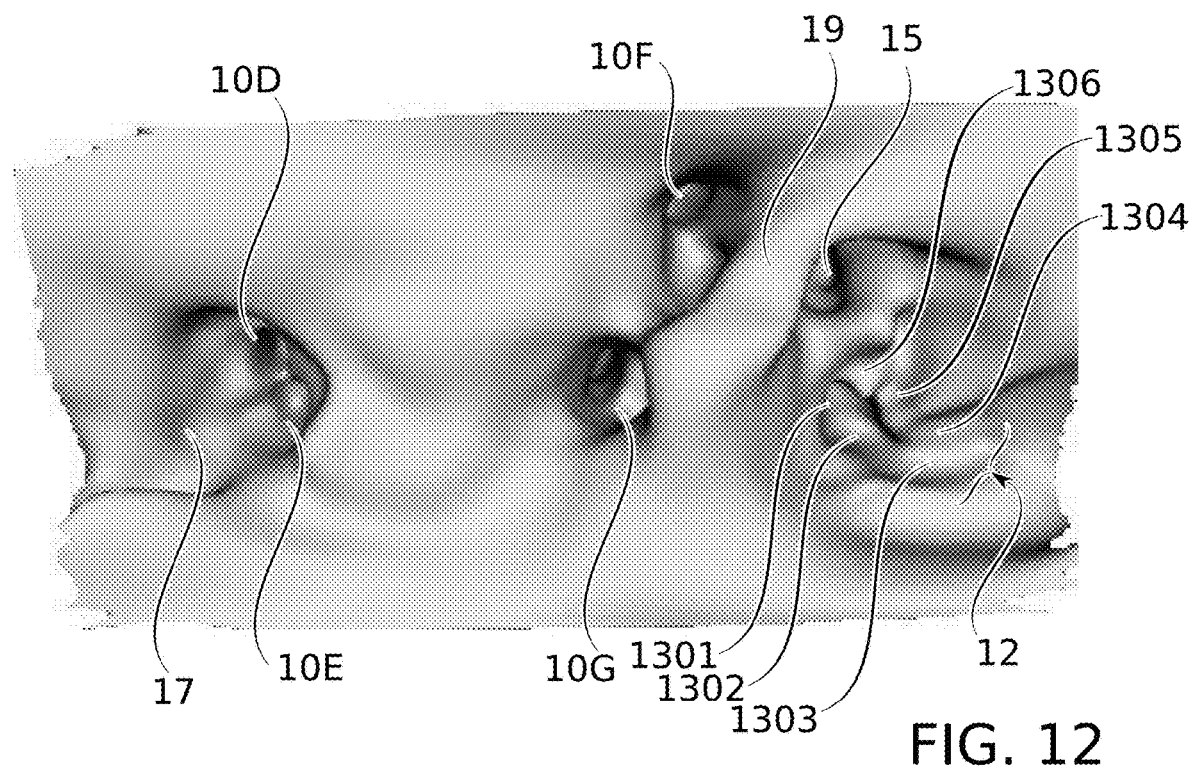
FIG. 12 presents a detailed flattened representation of a left atrium based on data acquired using field gradient-based remote imaging, according to some embodiments of the present disclosure.

Flattened Representations from Field Gradient-Based Remote Imaging of the Left Atrium Reference is now made to FIG. 12, which presents a detailed flattened reconstruction view of a left atrium based on data acquired using field gradient-based remote imaging, according to some embodiments of the present disclosure.

In some embodiments, data representing positions of a lumenal surface of a body cavity are obtained using a remote electrical field imaging method, for example a method described in U.S. Provisional Patent Application No. 62/546,775 entitled FIELD GRADIENT-BASED REMOTE IMAGING, and filed Aug. 17, 2017; the contents of which are incorporated herein in their entirety.

FIG. 12 indicates potential levels of left atrium surface detail which can be obtained using this method, displayed using the flattened reconstruction method.

Features shown already noted with respect to other figures herein include the pulmonary veins, here indicated specifically as the right superior pulmonary vein 10D, right inferior pulmonary vein 10E, left superior pulmonary vein 10F, and left inferior pulmonary vein 10G. Also shown are the left atrial appendage 15, trans-septal 17, and mitral valve 12.

The clarity of the orifice of the left atrial appendage 15 is potentially greater than typically seen in echocardiography, providing a potential advantage for the planning, guidance and/or verification of left atrial appendage occlusion procedures. Optionally, the flattened reconstruction view is used to characterize the LAA orifice shape and/or dimensions.

Certain additional details can also be seen, including the left atrial appendage ridge 19. The clarity of the left atrial appendage ridge 19 is potentially greater than typically seen in CT scans, providing a potential advantage for the planning, guidance and/or verification of ablations for arterial fibrillation, while saving exposure of the patient and doctor to X-ray radiation. The morphology of ridge 19 is variable among different patients (e.g., it can be more or less prominent), and this can have a substantial impact on how ablation should be performed—e.g., by its thickness (potentially requiring stronger ablation parameters, for example) and/or by its effect on ablation line morphology (e.g., there may be a need to ablate on the sides of the ridge in order to get a continuous ablation line capable of blocking electrical impulse transmission). Potentially, clearer visualization of the ridge or other surface irregularities helps a physician to understand the results of a treatment (e.g., understand why blockage is not initially achieved by an ablation treatment), and/or to plan new actions that will adjust the results.

Also shown are certain details of the mitral valve, including the three divisions 1301, 1302, 1303 of the posterior mitral valve leaflet, and the three divisions 1304, 1305, 1306 of the anterior mitral valve leaflet. This level of detail is seldom seen in CT scans, and illustrates a potential advantage of the method of field gradient-based remote imaging, optionally in conjunction with a flattened reconstruction view, for procedures such as mitral valve repair.

Systems for Flattened Representations of Curved Body Tissue Surfaces

Figure 13:
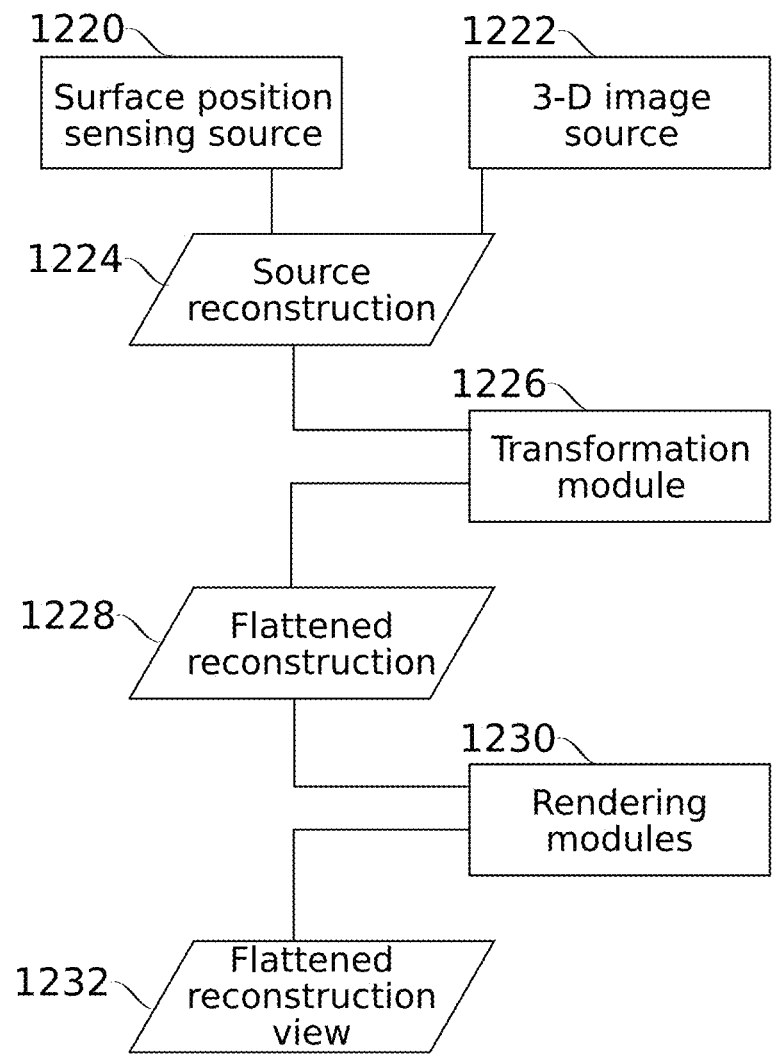
FIG. 13 schematically represents a system for production of a flattened representation, according to some embodiments of the present disclosure.

Reference is now made to FIG. 13, which schematically represents a system for production of a flattened reconstruction 1228 and/or flattened reconstruction view 1232, according to some embodiments of the present disclosure.

Block 1224 represents a source reconstruction, which is optionally provided and/or created based on data from a surface position sensing source 1220 and/or 3-D image source 1222. The surface position sensing source 1220 comprises, for example a catheter probe-based sensing system, using sensing of crossed electrical fields, self-generated electrical fields, local impedance characteristics, and/or another modality to generate data indicating positions of body tissue surfaces; for example by contact and/or proximity sensing together with probe position sensing, by remote field imaging, and/or by another method. The 3-D image source 1222 comprises, for example, an MRI image, CT image, radiography image, or another image type.

Transformation module 1226, in some embodiments, comprises a computer processor, processor instructions, and functionally associated computer memory, which are configured to transform source reconstruction 1224 into flattened reconstruction 1228, for example as described in relation to FIGS. 1A-1G herein.

Rendering module 1226, in some embodiments, comprises a computer processor, processor instructions, and functionally associated computer memory, which are configured to produce a flattened reconstruction view 1232 from flattened reconstruction 1228. For example, rendering module 1226 is configured to render (e.g., using 3-D graphics processing hardware) a 2-D image from 3-D position data described by flattened reconstruction 1228.

Examples of Global Curvatures and Flattening Results

Reference is now made to FIGS. 14A-14E, which schematically illustrate different 2-D examples of pre-flattening and post-flattening global curvatures and relief details, according to some embodiments of the present disclosure. The examples are provided in 2-D (that is, using curvatures of paths in two dimensions) to illustrate concepts described herein in particular relation to curvatures of surfaces in three dimensions.

In FIG. 14A, curve 1401 represents a cross-section of a surface which is to be flattened. Circle 1402 represents a choice of the global curvature (e.g., a cross section of a sphere) which is to be flattened. In the particular example shown, circle 1402 is chosen as a type of "best fit" circle. About as much area (analogous to volume, in the 3-D case) is enclosed by circle 1402 and not curve 1401 as is enclosed by curve 1401 and not circle 1402. FIG. 14B represents a flattened version of FIG. 14A. Line 1402A corresponds to circle 1402, with all the curvature of the circle removed. Cure 1401A represents relief details which remain in curve 1401 after removal of the global curvature. It is noted that any circle concentric with circle 1402 (for example circle 1403) will also be flattened in this transformation (for example, as shown by circle 1403A).

FIG. 14C represents a different flattened version of FIG. 14A, with some of the global curvature represented by circle 1402 remaining in flattened circle 1402B and flattened curve 1401B. Equivalently, a different choice of global curvature such as curve 1404 could be used as the basis of flattening (and then flattened completely, for example line 1404B) to result in a shape like that of 1401B.

The choice of global curvature is not limited to circles (or spheres in 3-D), and a different choice can lead to a different residual result of preserved relief features. For example, ellipse 1404 of FIG. 14D illustrates a different function which could be used to model a global curvature of path 1401. The resulting flattened curve (not shown) would suppress relief features such as the pattern of long peaks 1410 and valleys 1412 which superimposes on the shorter peaks 1412 and valleys 1413 of FIG. 14B.

FIG. 14E shows another example in which a global curvature of an open-sided curve 1405 is modeled by a parabola 1406 (in 3-D, the global curvature model could be a paraboloid, for example).

Considering circle 1402 (for example) as a reference shape, it may be said that curve 1401 represents a shape isomorphic with relief details (like 1401A, 1402A, 1410, 1411, and 1412 of FIG. 14B, for example) superimposed upon the reference shape 1402 curving around a point interior to curve 1401 (which may be the center point or any other interior point). The relief details superimpose relative differences in radial offset from the interior point. The same language applies, changed as necessary for surfaces (rather than 2-D curves) represented in three dimensions by source 3-D models (which are the 3-D equivalent of a 2-D curve like curve 1401).

The word "isomorphic" in the foregoing paragraph should be understood to mean that the curve 1401 has the same shape as the reference curve added together with the relief details (e.g., by offsetting). The terminology defines a way of referring to the relief details represented in a flattened 3-D model, and of explaining their relationship to relief details in a source 3-D model, without necessarily requiring that an explicit decomposition into relief details and reference shape is actually performed.

Examples of Features Distinguishable on Flattening Results

Reference is now made to FIGS. 15A-15D, which schematically illustrate features visible on a flattened representation view of a right atrium (FIGS. 15A-15B) and left atrium (FIGS. 15C-15D), according to some embodiments of the present disclosure.

Figure 15A:
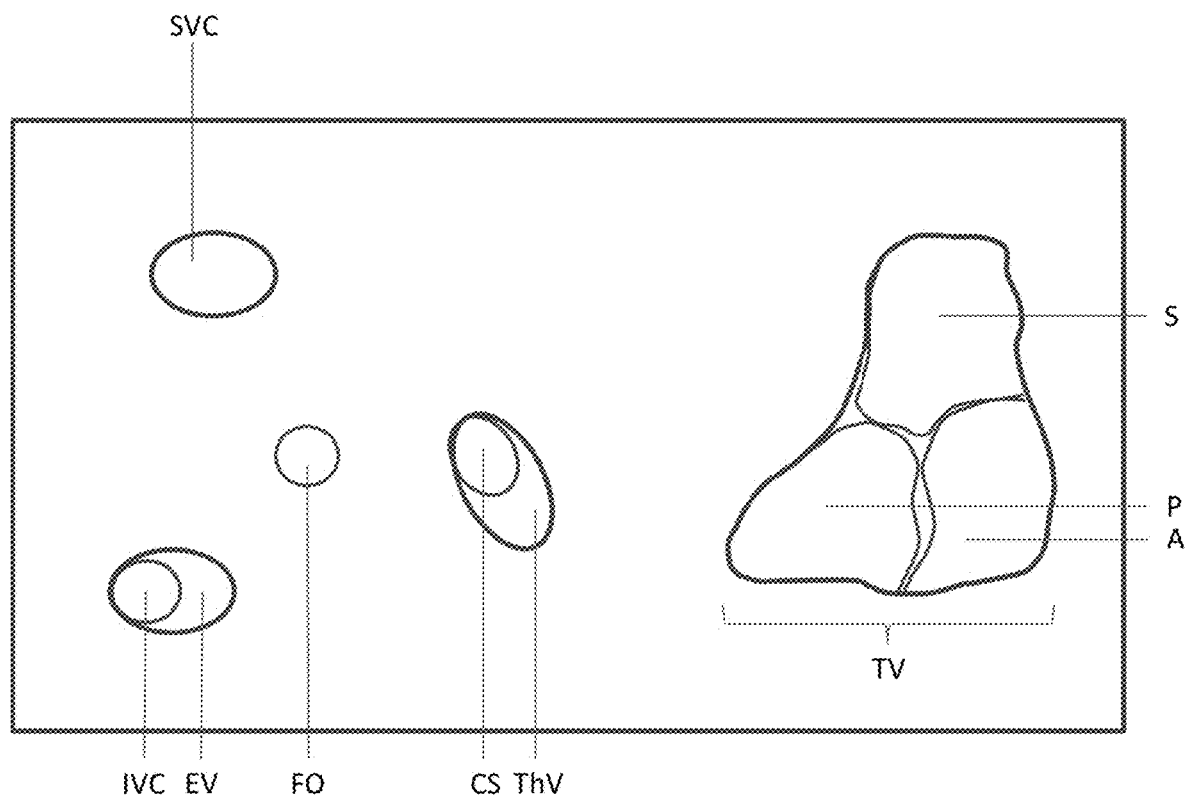
FIGS. 15A-15D schematically illustrate features visible on a flattened representation view of a right atrium (FIGS. 15A-15B) and left atrium (FIGS. 15C-15D), according to some embodiments of the present disclosure.
Figure 15B:
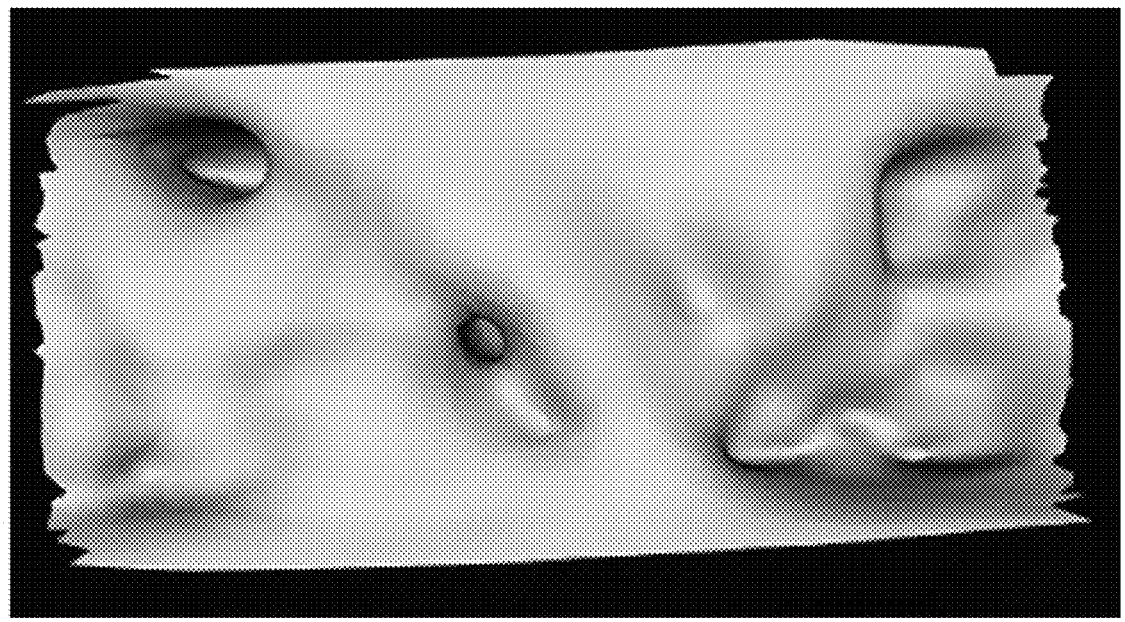
Figure 15C:
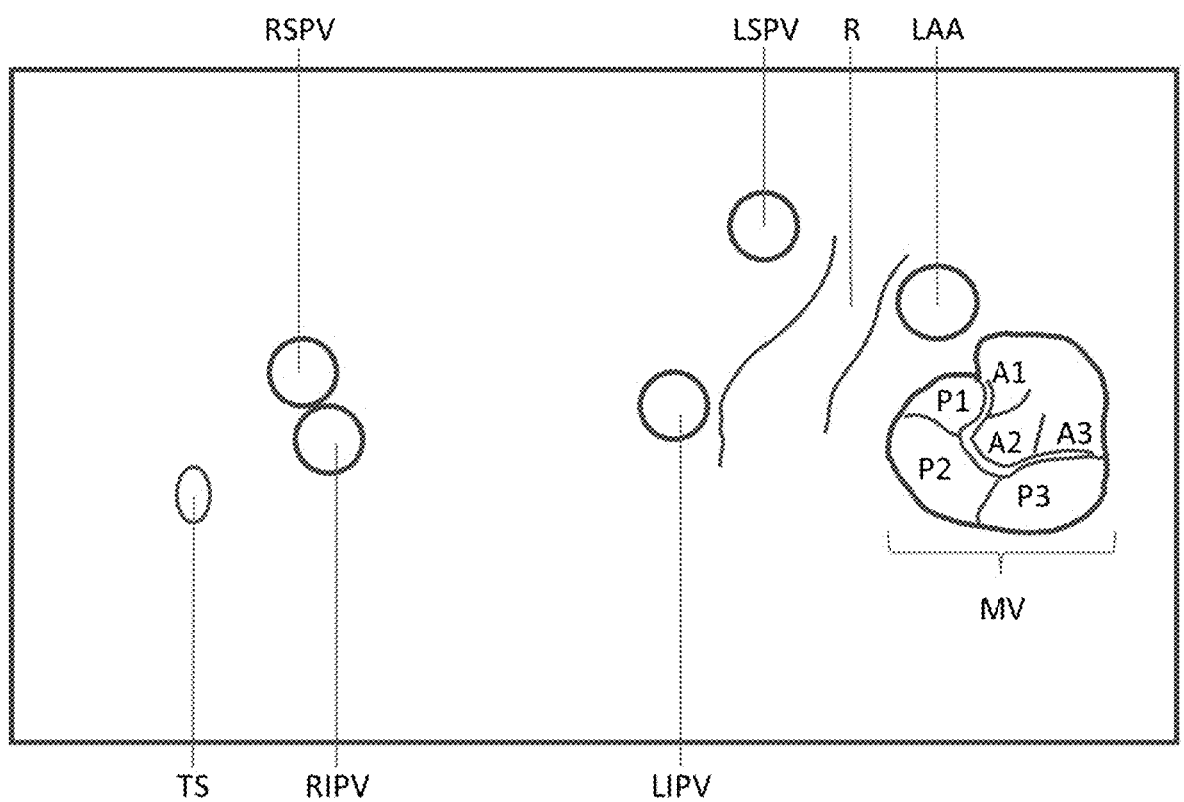
Figure 15D:
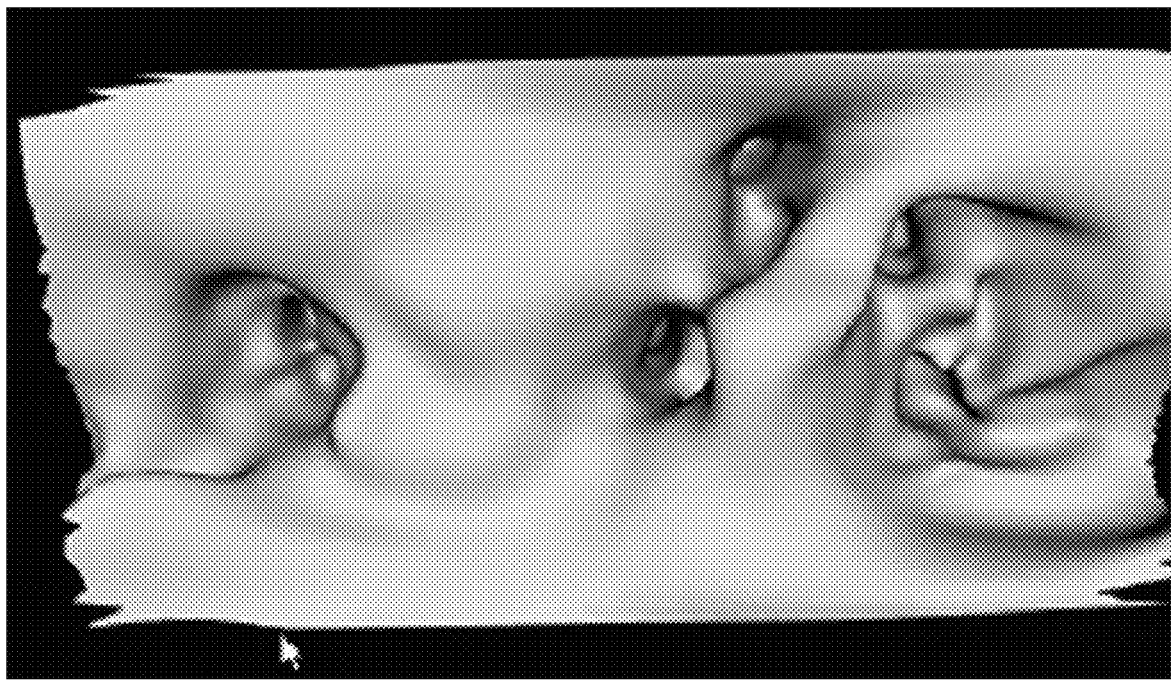

FIGS. 15A and 15C identify in outline features visible in corresponding positions in the flattened representation views of FIGS. 15B and 15D, respectively.

Features identified in FIG. 15A include:

| | |
|---|---|
| SVC | superior vena cava |
| IVC | inferior vena cava |
| EV | Eustachian valve |
| FO | Foramen ovalis |
| CS | Coronary sinus |
| ThV | Thebesian valve |
| TV | Tricuspid valve |
| S, P, A | Septal, posterior, and anterior leaflets of the tricuspid valve |

Features identified in FIG. 15C include:

| | |
|---|---|
| TS | Trans-septal puncture |
| RSPV | Right superior pulmonary vein |
| RIPV | Right inferior pulmonary vein |
| LSPV | Left superior pulmonary vein |
| LIPV | Left inferior pulmonary vein |
| R | Ridge of the left atrial appendage |
| LAA | Left atrial appendage |
| MV | Mitral valve |
| P1, P2, P3 | First, second, and third posterior leaflet regions |
| A1, A2, A3 | First, second, and third anterior leaflet regions |

Examples of Features Distinguishable on Flattening Results

Reference is now made to FIG. 16A, which illustrates a triangular meshing of the shape of a left atrium, according to some embodiments of the present disclosure. Reference is also made to FIGS. 16B-16E, which illustrated different flattenings of the triangular meshing of FIG. 16A, according to some embodiments of the present disclosure.

The meshing of FIG. 16A comprises substantially equilateral and equal-sized triangles.

FIGS. 16B and 16D show internal (endocardial) and external (epicardial) views of the same flattened 3-D representation of the mesh of FIG. 16A. The flattening has been performed according to a rectangular transformation, as described, for example, in relation to FIGS. 1C-1D. Triangles of the mesh are more nearly equilateral and uniform in size near the equatorial (central left-to-right) regions of the mesh. Nearer to the poles, (top and bottom), the triangles are stretched out, which is indicative of the increasingly smaller circumference (and so, smaller number of triangles) represented at each near-polar level. It may be noted in particular that horizontal lines extending from one edge of the flattened 3-D model to another edge of the flattened 3-D model distort distances relative to the source 3-D model by substantially the same amount through the linear region they extend across. The distribution of distortions may be changed in this as in other projection types by changing the parameters of how the flattening is performed, e.g., where discontinuities are introduced, and what region is to be centered in the resulting flattened 3-D model.

FIGS. 16C and 16E also show internal (endocardial) and external (epicardial) views of the same flattened 3-D representation of the mesh of FIG. 16A. The flattening has been performed according to an elliptical (Mollweide) transformation. The Mollweide projection corresponds to an equal-area, pseudocylindrical map projection which trades accuracy of angle and shape for accuracy of proportions in area. The triangles in these two images remain more nearly equal in area and shape over the extent of the image, though the angular distortion results in the "up" and "down" directions (for example) tilting toward the sides near the left and right edges of the reconstructions.

In either type of projection, there is also some change in triangle size due to the way that differences in depth cause differences in stretching during the "unwrapping".

It should be understood that the types of flattening are not limited to those shown, and may include, for example, the depth-preserving equivalent of any globe map projection method.

Examples of Continuous Updating of Images Using Flattening Results

Figure 17A:
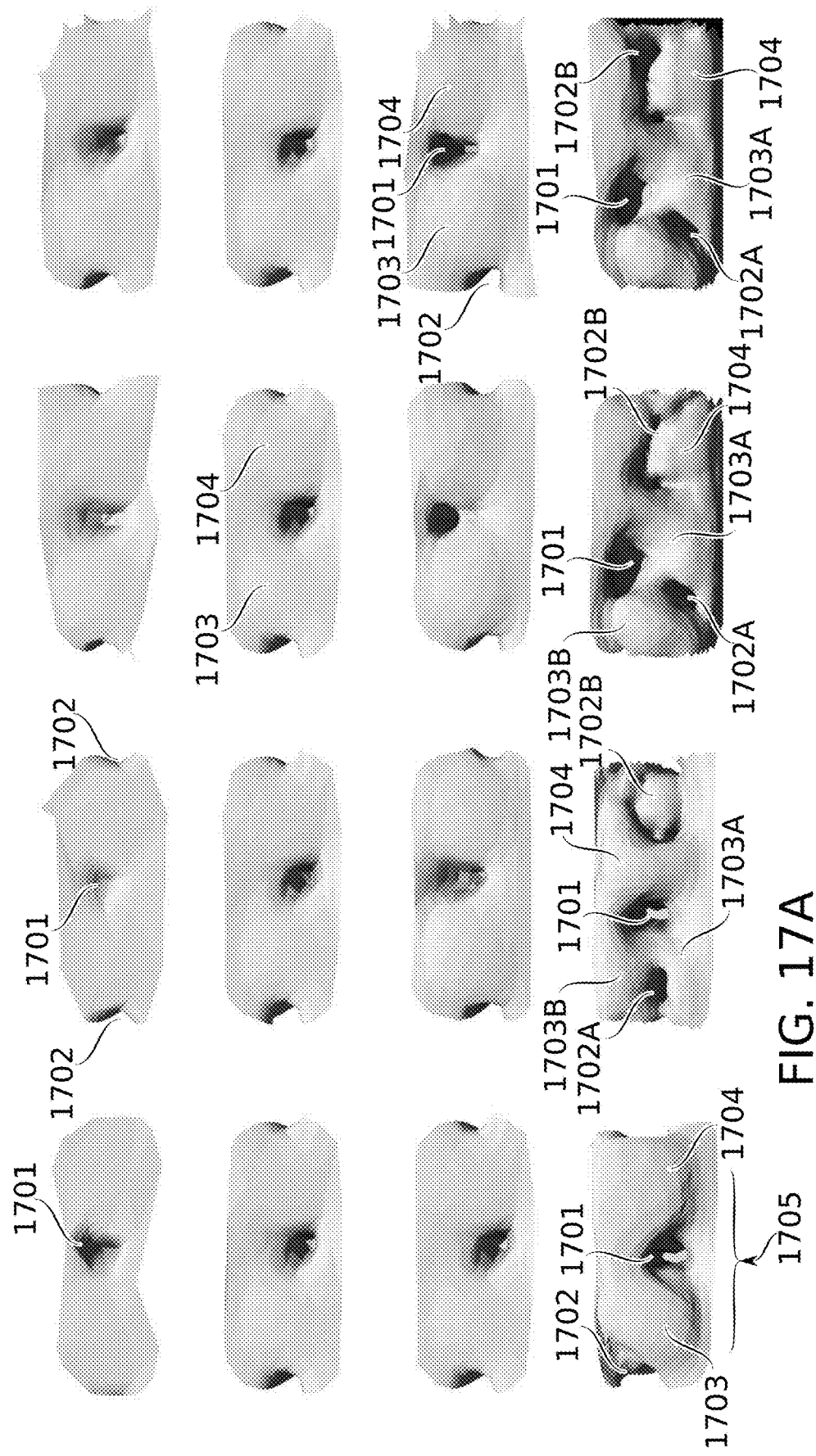
FIGS. 17A-17B each show a sequence of flattened 3-D images produced from earlier-measurement phase maps, and later-measurement phase, more refined maps of body lumen wall structure, based on a cumulative set of intralumenal voltage measurements, according to some embodiments of the present disclosure.
Figure 17B:
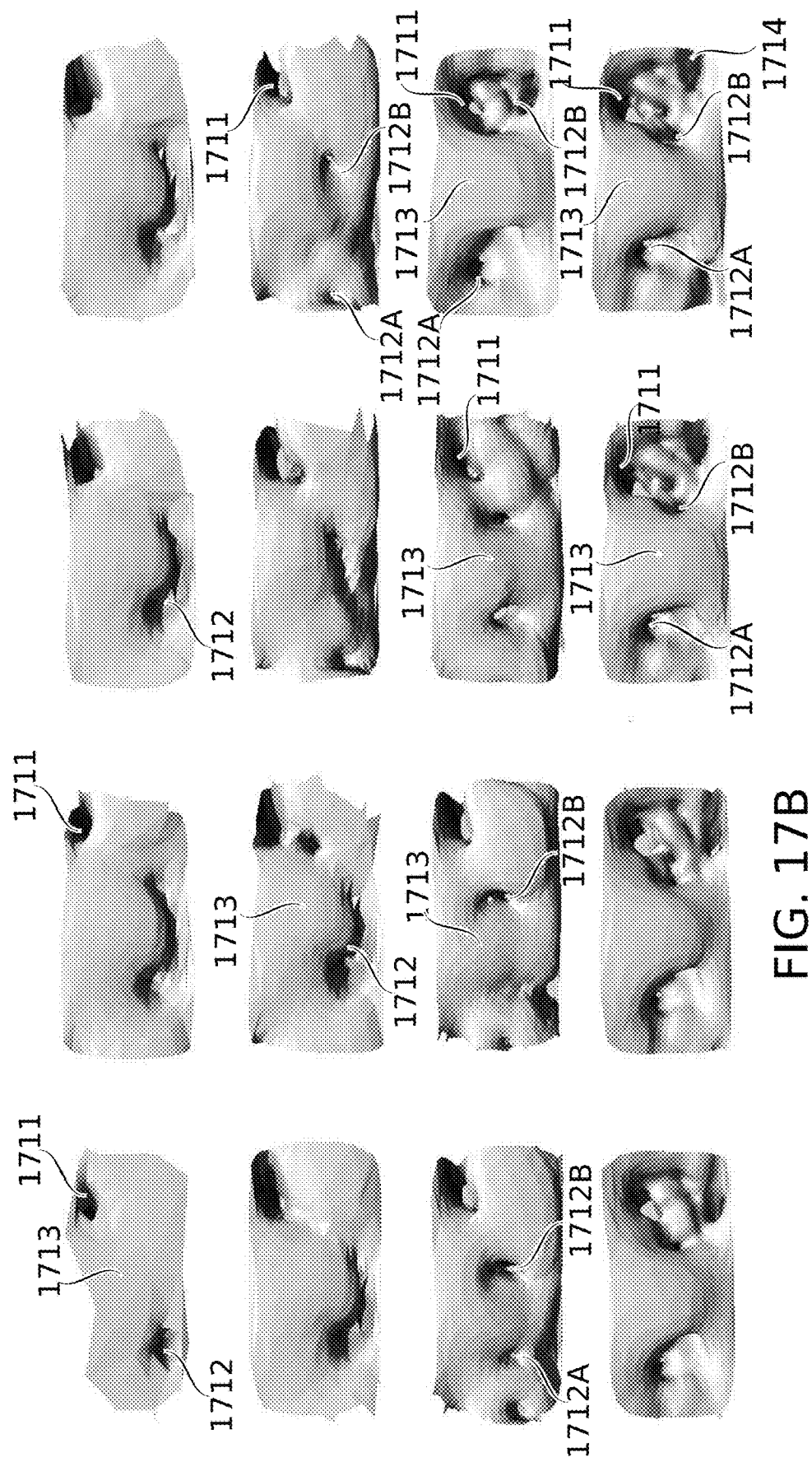

Reference is now made to FIGS. 17A-17B, which each show a sequence of images produced from maps of various measurement phases (earlier to later). The maps of later measurement phases are more refined, and show more body lumen wall structure; based on a cumulative set of intraluminal voltage measurements. In the images shown, measurements were made using a method of electrical field measurement from measurement probe positions within the body lumen and remote from the body lumen wall, for example as described in U.S. Provisional Patent Application No. 62/546,775 entitled FIELD GRADIENT-BASED REMOTE IMAGING and filed: Aug. 17, 2017; the contents of which are included herein by reference in their entirety. However, the general principle of updating the flattened images in response to new probe-measured data during a procedure as it becomes available applies also to other forms of probe mapping methods and/or measurements, for example methods described in U.S. Provisional Patent Application No. 62/445,433 entitled SYSTEMS AND METHODS FOR RECONSTRUCTION OF INTRA-BODY ELECTRICAL READINGS TO ANATOMICAL STRUCTURE and filed Jan. 12, 2017, and also an International Patent Application filed on the same date as this application PCT/IB2018/050192, the contents of which are included herein by reference in their entirety.

Measurements used in FIGS. 17A-17B are from a patient. Each of the two image sequences will be described with reference to certain selected features shown, and their evolution throughout the sequence. The sequences each proceed in time from left to right and from top to bottom (i.e., the upper-left image is the first image in the sequence, the image below it is the fifth image in the sequence, and the image in the lower right is the sixteenth and last image in the sequence). Images are displayed as endocardial (that is, internal views of the internal surface of the body lumen) panorama views, for example as described in relation to FIGS. 1C-1D, herein. The imaged regions shown comprise interior surfaces and connecting lumens, apertures, and/or cavities of a left atrium.

In FIG. 17A, the initial image produced (e.g., using data obtained by an electrode probe just after passage of the fossa ovalis from the right atrium into the left atrium) is very low in overall detail resolution, and shows essentially just one putative lumen 1701. Lumen 1701 has been automatically assigned to the central position in the unwrapped panoramic image, based on a weighting algorithm that seeks to put the "center of mass" of features distributed over the surface of the map at the center of a panoramic image produced from the map.

As the number of available measurements increases, an apparent second aperture 1702 appears in the images, offset from the first by about 180° (feature 1702 appears split, because it straddles the division made to splay the atrium surface into a panoramic view). Later in the crossing (in the second row of four images), two relatively raised regions 1703, 1704 also make an appearance. The raised regions, however, are potentially better characterized as (initially) "feature free" regions, relative to the relative receded regions corresponding to directions which have been better measured so as to reveal features of the surface. All of these features move around slightly as the addition of new measurements results in a change in the center of mass (and thus a change in automatic flattening parameters used) of the features represented by the images of FIG. 17A. By the end of the third row, the recessed features identified are represented with relatively high resolution (sharper edges generally, for example, and resolution of two holes within region 1701). However the detail available remains limited by the restricted initial sampling region and probe orientations used.

Beginning in the fourth row, aperture feature 1702 now splits into two sub-features 1702A, 1702B. Region 1703 splits into two subregions 1703A, 1703B. After revealing some new detail in area 1702B, the probe orients toward the region of features 1701 and 1702A, making measurements that finally appear to resolve them as the left PVs and the right PVs, respectively. These veins are optionally treatment targets, e.g., targets of a line ablation procedure intended to electrically isolate the pulmonary veins so that they can no longer transmit impulses to the atrium which can result in uncoordinated contractions and/or atrial fibrillation. In the final image of the sequence, the measurement probe has returned to a position where it can measure the region of feature 1702B, which now resolves as the apparent aperture leading to the mitral valve (at far right of the darkened region indicated as feature 1702B), and another region (the left lobe of the darkened region 1702B) which apparently indicates the LAA. Optionally, a user is presented with an interface allowing manual tagging of features as their identities become apparent. Optionally, features are identified automatically based on their characteristics; individually and/or in comparison with other resolved features.

Turning to FIG. 17B, two aperture-like features 1711, 1712, and one raised area 1713 (really a "featureless" region) are initially visible. Further measurements result in refinement of this picture up to about the second image of the second row. The region of feature 1712 (near the lower middle of the image) is selected as a first target for refinement by collection of additional data. This allows feature 1712 to become resolved into two distinct apertures 1712A, 1712B, with raised area 1713 acquiring some feature texture and protruding in-between. By the last image of the third row, the measurement probe has also explored feature 1711, which is revealed as partially merging with feature 1712B. The final image (at lower right) reveals the right pulmonary veins within region 1712A (the two lobes of the darkening there apparently corresponding to the ostia of the superior and inferior right pulmonary veins). The ostia of the left pulmonary veins are joined adjacent to one another (comprising feature 1712B) in a depression in common with the left atrial appendage (corresponding to feature 1711), with a recessed ridge in between. Raised region 1713 remains featureless extent extending between the left and right pulmonary vein ostia. Another depression 1714 has also become apparent, apparently associated with features of the mitral valve.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of producing an image of a heart chamber inner surface, the method comprising:
   transforming a source 3-D model of the heart chamber inner surface into a flattened 3-D model comprising relief details of the heart chamber inner surface represented as relative differences in depth over an unwrapped and flattened surface extent; and
   producing an image from the flattened 3-D model,
   wherein the transforming produces a flattened 3-D model having width, length, and depth; and
   wherein the relief details are represented in depth, and the width and length of the flattened 3-D model correspond to spherical angle positions in the source 3-D model and
   wherein the flattened 3-D model is not presented with a fisheye lens perspective.

2. The method of claim 1, wherein the flattened 3-D model also represents transformed positions from the volume of the source 3-D model away from the inner surface of the body chamber.

3. The method of claim 1, wherein the source 3-D model represents the inner surface of the heart chamber through a solid angle of at least $3\pi$ steradians.

4. The method of claim 1, wherein the produced image represents at least 80% of the inner surface of the heart chamber.

5. The method of claim 1, wherein the heart chamber comprises a heart left atrium.

6. The method of claim 5, wherein at least one feature from among a group of features consisting of: a heart left atrial appendage ridge, trans-septal, and mitral valve leaflet is distinguishably and identifiably represented in the flattened 3-D model.

7. The method of claim 1, wherein the heart chamber comprises a heart right atrium.

8. The method of claim 7, wherein at least one feature from among a group of features consisting of: a Thebesian valve, Eustachian valve, tricuspid valve leaflet, and a coronary sinus is distinguishably and identifiably represented in the flattened 3-D model.

9. The method of claim 1, wherein the transforming introduces a discontinuity between two portions of the flattened 3-D model which correspond to two different and adjacent portions of the inner surface of the heart chamber.

10. The method of claim 1, wherein the transforming comprises converting a representation of the source 3-D model in spherical coordinates into 3-D Cartesian coordinates to produce the flattened 3-D model.

11. The method of claim 1, comprising repeating a plurality of performances of the transforming and producing, wherein the source 3-D model is updated during the repeating by new data indicating positions of the surface.

12. The method of claim 11, wherein the source 3-D model is iteratively updated with position measurements of the surface measured from an intrabody probe, as the intrabody probe is moved within the heart chamber.

13. The method of claim 12, wherein the position measurements measured from the intrabody probe are measured using measurements of one or more electrical fields established within the heart chamber.

14. The method of claim 12, wherein the position measurements measured from the intrabody probe are measured using remote electrical field imaging.

15. The method of claim 1, further comprising:
   receiving an indication of a position inside the heart chamber and located away from the heart chamber surface; and
   transforming the position into 3-D coordinates of the flattened 3-D model;
   wherein the image produced includes an indication located at the transformed position.

16. The method of claim 1, comprising producing a plurality of images from the flattened 3-D model, wherein a first image is a view of the flattened 3-D model from a first direction, a second image is a view of the flattened 3-D model from a second direction, and the first and second images show different sides of a same surface portion.

17. The method of claim 1, comprising producing an image from the flattened 3-D model showing both a portion of an internal side and a portion of an external side of a surface represented in the flattened 3-D model.

18. The method of claim 1, wherein a straight linear region extending from one edge of the flattened 3-D model to another edge of the flattened 3-D model distorts distances relative to the source 3-D model by substantially the same amount through the linear region.

19. The method of claim 18, wherein the amount of distortion along the linear region is adjustable by user selection.

20. The method of claim 1, comprising collecting data for said source 3D model using an intrabody probe, wherein said producing an image includes displaying a representation of said probe on said image at a position also transformed using said transforming and overlying a part of said image.

21. The method of claim 1, wherein the transformation is not a projection onto a 2D surface that collapses representation through a range of positions in depth to a single pixel or other 2-D image region.

22. The method of claim 1, wherein the transformation is 1:1, so that positions in the flattened 3-D model uniquely correspond to positions in the source 3-D model.

23. The method of claim 1, wherein said transforming comprises transforming from 3D coordinate positions to 3D coordinate positions using a 3D transformation function which maps at least part of said 3D model to at least part of said flattened 3D model.

* * * * *